(12) United States Patent
Yi et al.

(10) Patent No.: US 9,962,075 B2
(45) Date of Patent: *May 8, 2018

(54) DEVICES, METHODS, AND SYSTEMS OF FUNCTIONAL OPTICAL COHERENCE TOMOGRAPHY

(71) Applicant: Northwestern University, Evanston, IL (US)

(72) Inventors: Ji Yi, Evanston, IL (US); Wenzhong Liu, Evanston, IL (US); Vadim Backman, Chicago, IL (US); Hao F. Zhang, Deerfield, IL (US); Kieren J. Patel, Evanston, IL (US)

(73) Assignees: Northwestern University, Evanston, IL (US); Opticent INC, Deerfield, IL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/465,285

(22) Filed: Mar. 21, 2017

(65) Prior Publication Data

US 2017/0188818 A1 Jul. 6, 2017

Related U.S. Application Data

(62) Division of application No. 14/698,641, filed on Apr. 28, 2015, now Pat. No. 9,619,903.

(Continued)

(51) Int. Cl.
*G06K 9/00* (2006.01)
*A61B 3/10* (2006.01)
(Continued)

(52) U.S. Cl.
CPC ............. *A61B 3/102* (2013.01); *A61B 1/04* (2013.01); *A61B 3/1233* (2013.01);
(Continued)

(58) Field of Classification Search
None
See application file for complete search history.

(56) References Cited

U.S. PATENT DOCUMENTS 7,570,367 B2 * 8/2009 Ohashi ................ A61B 5/0059
250/339.08
8,244,334 B2 8/2012 Huang et al.
(Continued)

FOREIGN PATENT DOCUMENTS

CN 101720205 6/2010
CN 103443579 12/2013
(Continued)

OTHER PUBLICATIONS

International Searching Authority, "Search Report", issued in connection with PCT patent application No. PCT/US2015/028053, dated Jul. 23, 2015, 4 pages.
(Continued)

*Primary Examiner* — Avinash Yentrapati
(74) *Attorney, Agent, or Firm* — Hanley, Flight and Zimmerman, LLC

(57) ABSTRACT

The present disclosure provides systems and methods for the determining a rate of change of one or more analyte concentrations in a target using non invasive non contact imaging techniques such as OCT. Generally, OCT data is acquired and optical information is extracted from OCT scans to quantitatively determine both a flow rate of fluid in the target and a concentration of one or more analytes. Both calculations can provide a means to determine a change in rate of an analyte over time. Example methods and systems of the disclosure may be used in assessing metabolism of a tissue, where oxygen is the analyte detected, or other functional states, and be generally used for the diagnosis, monitoring and treatment of disease.

20 Claims, 42 Drawing Sheets

Related U.S. Application Data

(60) Provisional application No. 61/985,278, filed on Apr. 28, 2014.

(51) Int. Cl.

| | |
|---|---|
| *G06T 7/00* | (2017.01) |
| *G01B 9/02* | (2006.01) |
| *A61B 5/1455* | (2006.01) |
| *A61B 3/12* | (2006.01) |
| *A61B 5/145* | (2006.01) |
| *A61B 5/0205* | (2006.01) |
| *A61B 1/04* | (2006.01) |
| *G06F 17/13* | (2006.01) |
| *A61B 5/00* | (2006.01) |
| *A61B 5/026* | (2006.01) |

(52) U.S. Cl.
CPC ........ *A61B 5/0205* (2013.01); *A61B 5/14507* (2013.01); *A61B 5/14517* (2013.01); *A61B 5/14532* (2013.01); *A61B 5/14535* (2013.01); *A61B 5/14542* (2013.01); *A61B 5/14551* (2013.01); *G01B 9/02091* (2013.01); *G06F 17/13* (2013.01); *G06T 7/0014* (2013.01); *A61B 5/0066* (2013.01); *A61B 5/0261* (2013.01); *G06T 2207/10028* (2013.01); *G06T 2207/10101* (2013.01)

(56) References Cited

U.S. PATENT DOCUMENTS

| | | | | |
|---|---|---|---|---|
| 2007/0014464 | A1* | 1/2007 | Ohashi | A61B 3/102 382/131 |
| 2007/0179368 | A1* | 8/2007 | Backman | A61B 5/0084 600/315 |
| 2008/0097194 | A1* | 4/2008 | Milner | A61B 5/0066 600/425 |
| 2009/0275812 | A1* | 11/2009 | Reichgott | A61B 5/0066 600/310 |
| 2010/0262116 | A1* | 10/2010 | Sowb | A61B 5/00 604/500 |
| 2014/0204391 | A1 | 7/2014 | Nebosis et al. | |
| 2014/0268163 | A1* | 9/2014 | Milner | A61B 3/102 356/451 |
| 2015/0348287 | A1 | 12/2015 | Yi et al. | |

FOREIGN PATENT DOCUMENTS

| | | | |
|---|---|---|---|
| KR | 20110048159 | | 5/2011 |
| WO | 2012075126 | | 6/2012 |
| WO | WO2012/075126 | * | 7/2012 |

OTHER PUBLICATIONS

International Searching Authority, "Written Opinion", issued in connection with PCT patent application No. PCT/US2015/028053, dated Jul. 23, 2015, 5 pages.

Internationa Bureau, "International Preliminary Report on Patentability", issued in connection with PCT/US2015/028053, dated Nov. 10, 2016, 7 pages.

European Patent Office, "Communication Pursuant to Rules 161(1) and 162 EPC", issued in connection with European patent application No. 15723787.6, Dec. 22, 2016, 2 pages.

United States Patent and Trademark Office, "Notice of Allowance and Fee(s) Due", issued in connection with U.S. Appl. No. 14/698,641, dated Nov. 23, 2016, 20 pages.

United States Patent and Trademark Office, "Notice of Allowability", issued in connection with U.S. Appl. No. 14/698,641, dated Dec. 14, 2016, 12 pages.

United States Patent and Trademark Office, "Non-Final Office action", issued in connection with U.S. Appl. No. 14/698,641, dated Apr. 8, 2016, 16 pages.

The State Intellectual Property Office of China, "Office action", issued in connection with Chinese application No. 201580035053.x, dated Nov. 3, 2017, 11 pages.

Canadian Patent Office, "Office action", issued in connection with Canadian Patent application No. 2,950,102, dated Nov. 14, 2017, 5 pages.

* cited by examiner

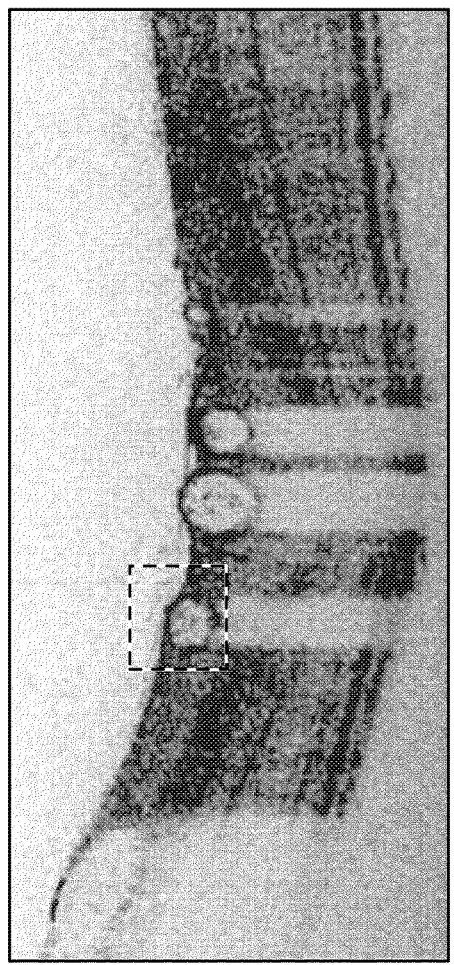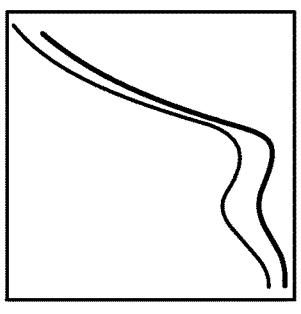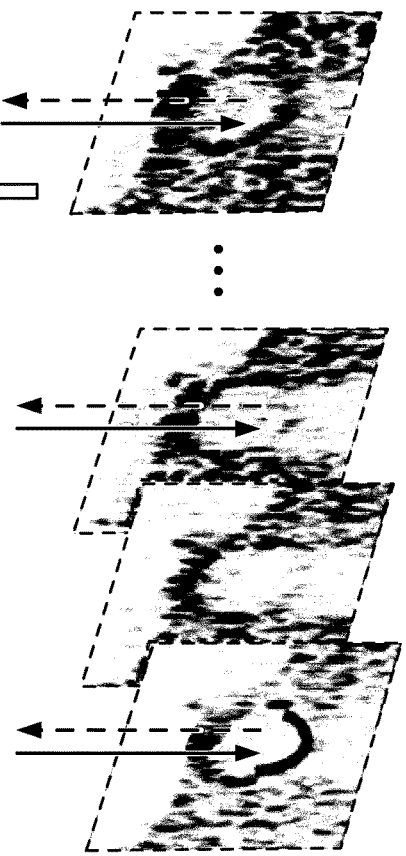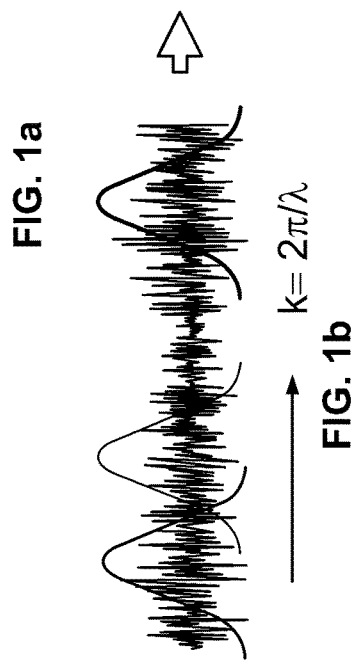
FIG. 1a
FIG. 1b
FIG. 1c
FIG. 1d

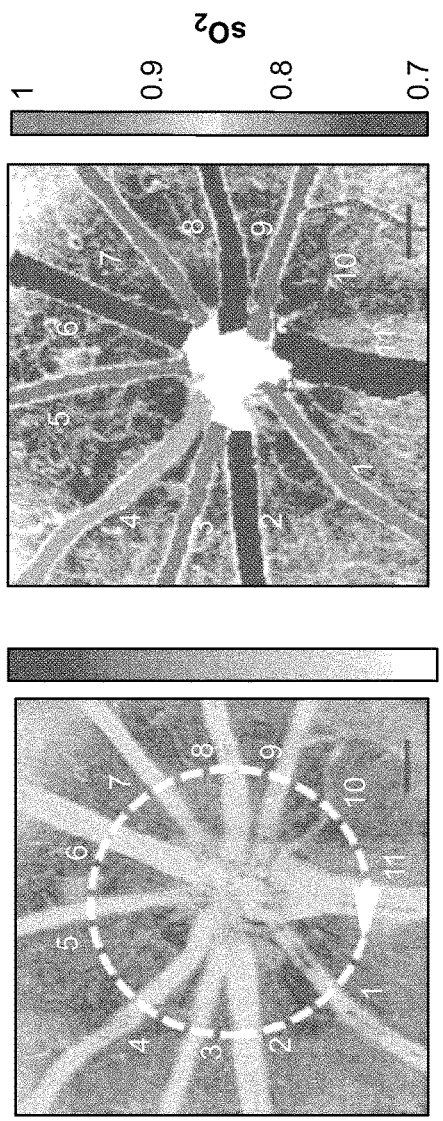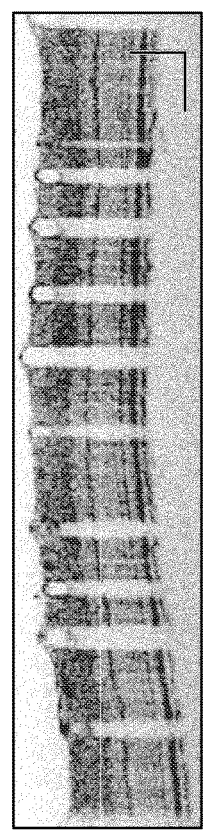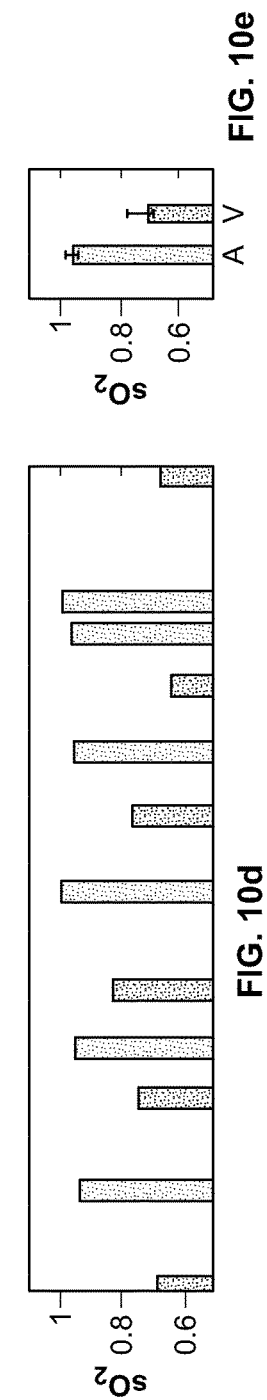
FIG. 10a
FIG. 10b
FIG. 10c
FIG. 10d
FIG. 10e

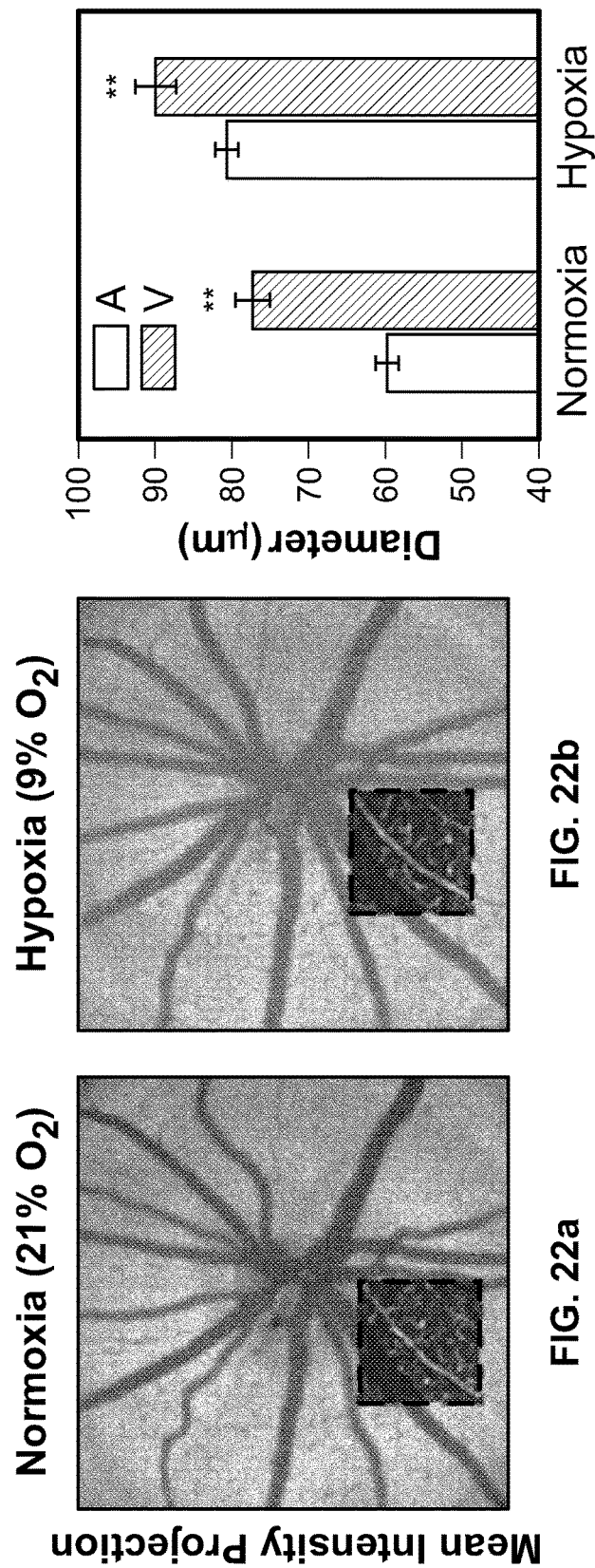

Microangiograph

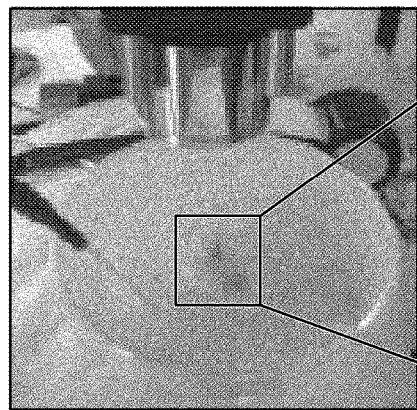
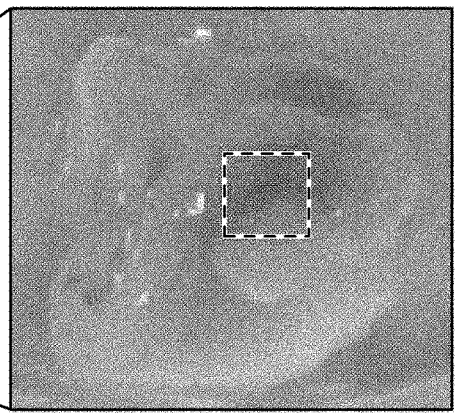
FIG. 26c  　　　　　　　　FIG. 26d
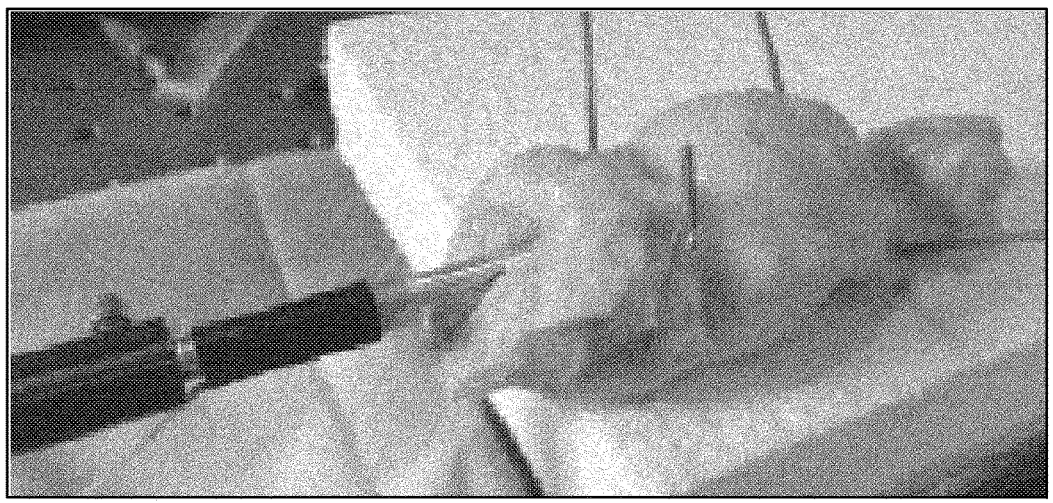
FIG. 26e

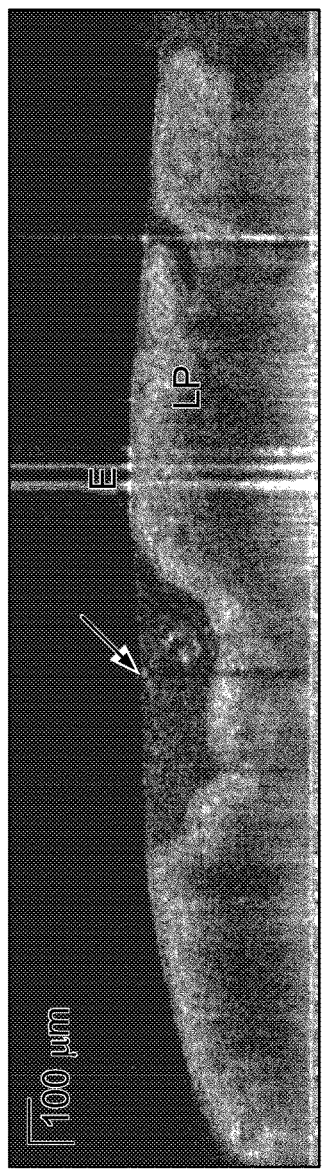
FIG. 27a
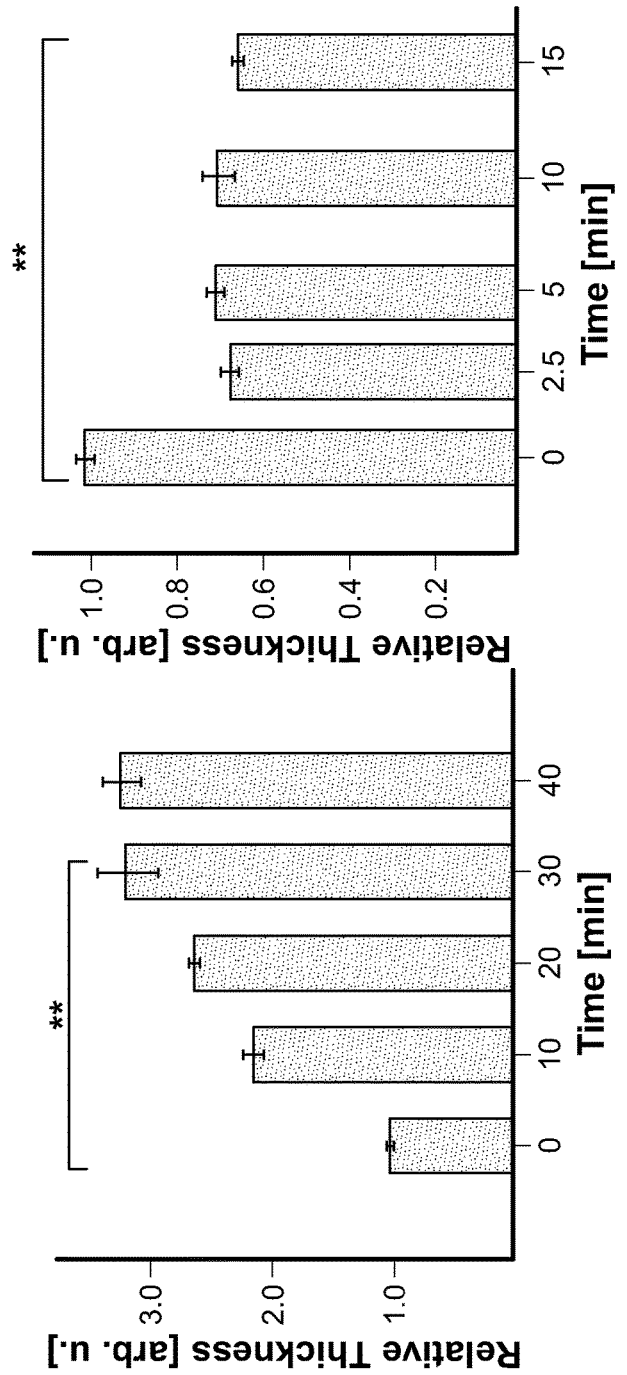
FIG. 27b
FIG. 27c

DEVICES, METHODS, AND SYSTEMS OF FUNCTIONAL OPTICAL COHERENCE TOMOGRAPHY

CROSS-REFERENCE

This application arises from a divisional of U.S. patent application Ser. No. 14/698,641 filed on Apr. 28, 2015, entitled "DEVICES, METHODS, AND SYSTEMS OF FUNCTIONAL OPTICAL COHERENCE TOMOGRAPHY", which claims the benefit of U.S. Patent Application Ser. No. 61/985,278, filed on Apr. 28, 2014, both of which are incorporated herein by reference in their entireties.

STATEMENT REGARDING FEDERALLY SPONSORED RESEARCH FOR DEVELOPMENT

This invention was made with government support under grant numbers 1 RC4EY021357 and 1 R01EY019951 awarded by the National Institutes of Health; and grant numbers CBET-1055379 and CBET-1240416 awarded by the National Science Foundation. The government has certain rights in the invention.

BACKGROUND OF THE DISCLOSURE

Optical Coherence Tomography (OCT) is a non-invasive optical imaging technique which produces depth-resolved reflectance imaging of samples through the use of a low coherence interferometer system. OCT imaging allows for three-dimensional (3D) visualization of structures in a variety of biological systems and non-biological systems not easily accessible through other imaging techniques. In some instances OCT may provide a non-invasive, non-contact means of assessing information without disturbing or injuring a target or sample. In medicine for example, OCT applications have included but are not limited to non-invasive means of diagnosis of diseases in the retina of the eye, interventional cardiology treatment and assessment, and diagnostics of skins lesion for dermatology.

Generally, OCT is used to generate 3D images of various structures, including vessels such as blood vasculature. Previously described methods of OCT provide methods for obtaining structural information directed at acquiring information about the size, shape, topology and physical attributes of the outside structures of vessels. However, information regarding physical and chemical attributes inside vessels and structures can also be useful, yielding more functional and potentially useful information about a system.

In medical diagnostics for example, vascular visualization and quantitative information about attributes of blood can be important for the diagnosis and treatment of many diseases. For example, approximately 50% of Americans will get cancer and approximately 50% of those will die from cancer. In the example of ocular disease, such as diabetic retinopathy, age related macular degeneration (AMD), glaucoma, nearly 10 million people in the U.S. and over 200 million people worldwide may be at risk for vision loss or blindness. It is suspected that vasculature remodeling and biochemical pathways that affect abnormal morphology of blood supplies in the eye and around tumors may be correlated with the onset and prognosis of these diseases, respectively. In some examples, an abnormal increase or decrease in metabolism, illustrated through abnormal blood vessel proliferation may also correlate with disease.

Non-invasive methods that allow acquisition of information about tissue attributes related to the etiologies of diseases, may lead to prevention of such diseases. The ability to measure blood flow, and other various biochemical analytes within a blood flow, such as oxygen ($pO_2$), glucose or other biomarkers can help indicate a functional state of target tissue, such as metabolic activity. In some examples, the ability to understand a functional state of a target tissue, can be useful for treatment, monitoring or prevention of disease. This especially true when attributes such both as blood flow and oxygen can both be measured. Currently, there are no non-invasive three dimensional (3D) imaging techniques to measure oxygen metabolism in vivo in tissues. There is need in the art for improved methods and devices for non-invasive 3D quantitative imaging of metabolism and other target functions for a variety of applications including but not limited to the treatment and diagnosis of disease.

SUMMARY OF THE DISCLOSURE

In a first aspect, the present disclosure provides for a method for imaging a target, the method comprising performing optical coherence tomography (OCT) scanning on a target with one or more beams of low coherence light, wherein the one or more beams of light comprise one or more wavelengths, acquiring optical information from reflected signals generated by the OCT scanning, quantitatively 3D-imaging in the target, determining a flow rate of a fluid and a concentration of one or more analytes from the optical information acquired, and determining a rate of change of the one or more analyte concentrations in the target.

Another aspect of the present disclosure provides a method for the diagnosis or treatment of a disease in a subject, the method comprising obtaining 3D OCT scans of a target; determining a status of one or more molecular markers in a bodily fluid in the target, while simultaneously quantifying flow of the bodily fluid from the 3D scans generated; and providing a medical decision. In some examples, OCT scans includes invisible light, visible light or near-infrared (NIR) light.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of a device of this disclosure are set forth with particularity in the appended claims. A better understanding of the features and advantages of this disclosure will be obtained by reference to the following detailed description that sets forth illustrative examples, in which the principles of a device of this disclosure are utilized, and the accompanying drawings of which:

FIG. 1a is an example in vivo B-scan image of a pigmented rat eye using inversed contrast.

FIG. 1b is an example short time Fourier transform (STFT) OCT spectra.

FIG. 1c is an example STFT OCT extracted spectra, from the bottom of the vessel wall.

FIG. 1d is an example of reflection spectra from the bottom of the vessel.

FIG. 10a is an example vis-OCT fundus image. The white circular line represents the B-scan trajectory.

FIG. 10b is an example fused vascular image and oxygen map of major vessels.

FIG. 10c is an example of a retinal B-scan.

FIG. 10d is a graph showing an example quantification of $sO_2$ for each individual vessel.

FIG. 10e is an example of average arterial and venous $sO_2$ values.

FIG. 22a illustrates example retinal vasculature changes under hypoxia. Mean intensity projection image around optic disk under normoxia.

FIG. 22b illustrates an example mean intensity projection image around optic disk under normoxia.

FIG. 22c illustrates an example of average diameter of the major arterioles (A) and veins (V) in normoxia and hypoxia.

FIG. 22d illustrates an example magnified view of the insert in FIG. 22a.

FIG. 23a provides an example schematic representation of the hypoxia protocol. The inhaled oxygen content was reduced gradually in six stages from 21% to 9%. Arterial and venous $sO_2$, blood flow, and blood vessel diameter were measured at each step.

FIG. 26a shows an example schematic diagram of a table-top vis-OCT system.

FIG. 26c shows an example endocervical tissue sample/target imaged with an endoscopic NIR-OCT probe.

FIG. 26d shows an example endocervical tissue sample/target placed under an OCT objective lens.

FIG. 26e indicates an example process of performing 3-dimensional endoscopic OCT scan. BS, beam splitter; DC, dispersion compensation; GM, galvanometer mirror; L, objective lens; M1, M2, reflective mirror; F, pigtailed fiber; FC, fiber coupler; GL, grin lens; P, prism; NIR, near infrared; OCT, optical coherence tomography; vis-OCT, visible-light optical coherence tomography.

FIG. 27a illustrates example dynamic monitoring of mucus layer thickness change during secretion and enzymatic hydrolysis. FIG. 27a includes a single vis-OCT B-scan showing anatomical features of endocervical tissue.

FIG. 27b shows an example graph of measured maximum mucus thickness when incubated in PBS solution at 37 during a period of 40 minutes.

FIG. 27c shows an example graph of measured maximum mucus thickness after adding neuraminidase. The example of FIG. 27c was observed over a period of 15 minutes. **, $P<0.01$ comparing to Time=0. Arrow, surface of mucus; E, epithelium; LP, lamina propria; vis-OCT, visible-light optical coherence tomography.

Figure 2B:
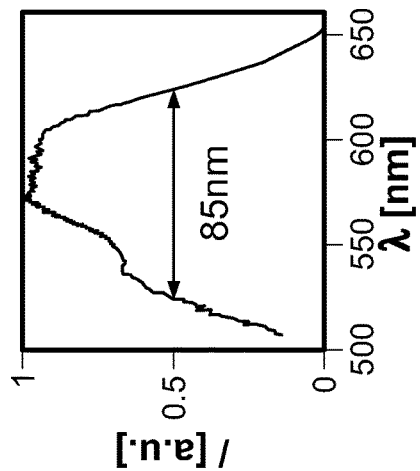
FIG. 2b is an example illumination spectrum of a free space vis-OCT device.

The following detailed description of certain examples of the present invention will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION OF THE DISCLOSURE

I. General Overview

The methods, devices and systems of the present disclosure provide for functional optical coherence tomography (fOCT). Generally, fOCT may comprise a non-invasive, non-contact method for determining a functional state of target, such as the health of bodily tissue. In some examples, fOCT may be used for determining the change in metabolism of a tissue, therefore indicating something about disease state or health.

Generally, fOCT employs any method of OCT, as known in the art. fOCT provides a method of extracting a full set of optical properties from OCT spectra and simultaneously or substantially simultaneously extracting optical information to calculate flow rate of a fluid in a target and a concentration of a particular analyte in the target. In some examples, the same or single A-scan generated from OCT scans may be used for calculations of flow and analyte concentrations. For example, the target may be a human retina, where blood flow and oxygen may be determined or quantified using fOCT. In some examples, the target could be skin and the flow rate of sweat is calculated with a quantification of glucose.

Figure 13:
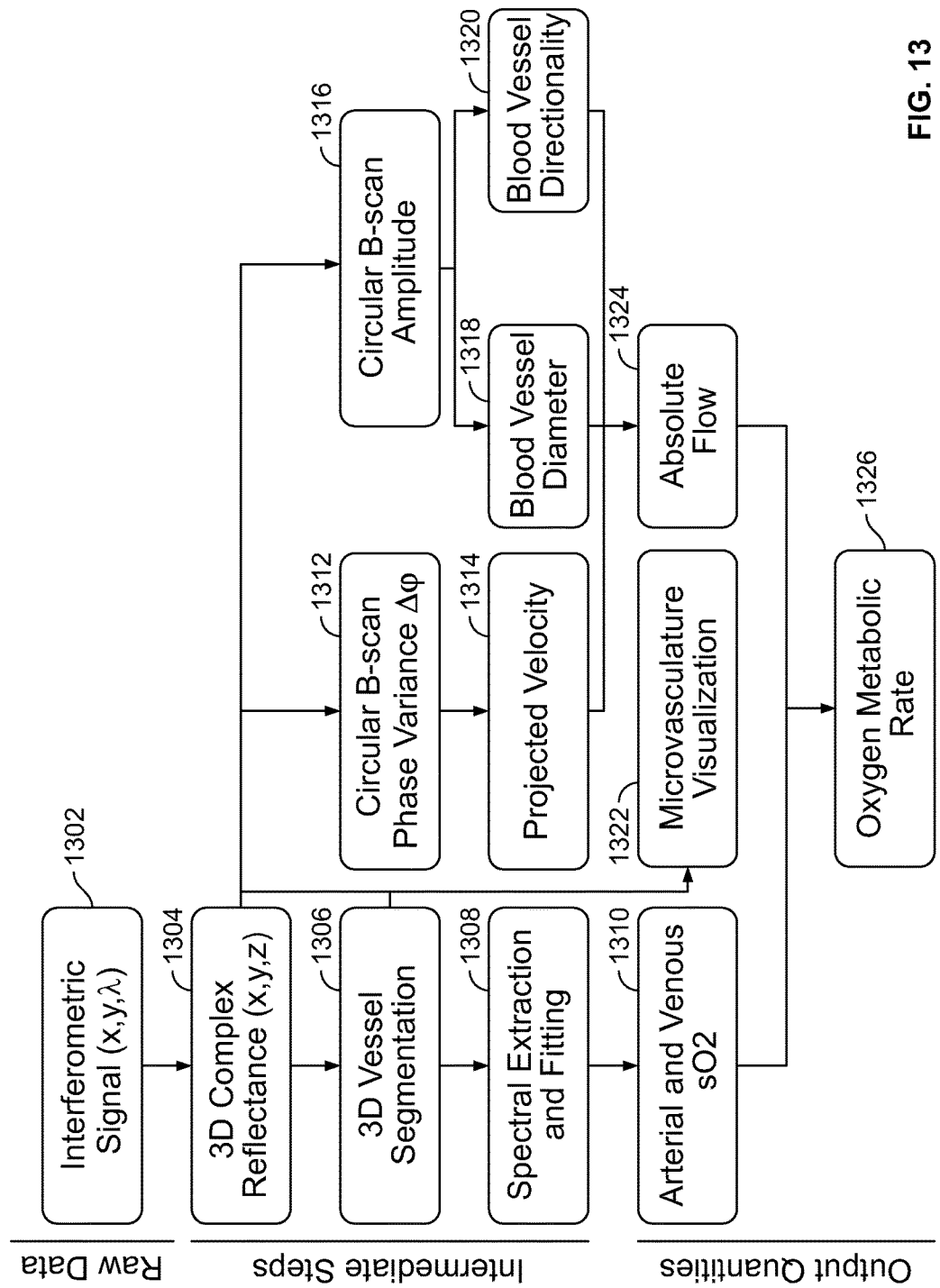
FIG. 13 is a flow schematic for an example process of quantitatively 3D-imaging in the target, a flow rate of a fluid and a concentration of oxygen, from optical information acquired and determining a rate of change of metabolism based on oxygen consumption.

Generally, a schematic for determining metabolic rate is provided in FIG. 13 and provided for example. In some examples, interferometric data, 1302, is acquired from OCT scans and converted to 3D complex reflectance data, 1304. This same A-scan data is then used to perform simultaneous, or substantially simultaneous calculations or determinations of flow and analyte concentrations. In some examples, 3D vessel segmentation, 1306, spectral extraction, 1308 are performed to quantify oxygen saturation ($sO_2$), 1310. In some examples, this can be expressed as partial pressure of oxygen, $pO_2$. Simultaneously, circular brightness scan (B-scan) variance, 1312, and projected velocity, 1314, and microvasculature visualization, 1322, are used determined flow rate of blood. Simultaneously, circular B-scan amplitude, 1316, blood vessel diameter, 1318 and blood vessel directionality, 1320 may be used to determine absolute flow, 1324. Taken together, these calculations can help determine an accurate change in oxygen consumption in a tissue, or overall oxygen metabolic rate, 1326.

In some examples, the accurate quantification of a flow parameter and an analyte concentration can be used to determine a change in state of target function. For example, a change in metabolism or oxygen consumption of the human retina may indicate retinal disease. In the example of skin monitoring and glucose in sweat, blood glucose levels for diabetic monitoring may be performed using the methods, devices and systems of the disclosure.

Given the label-free, non-invasive, non-contact methods of the disclosure, a variety of medical applications may be employed including the disease monitoring and diagnosis of cancer and variety of other ocular diseases.

In some examples, the quantitatively 3D-imaging in the target is performed without contacting at least one analyte with an exogenous reagent or label. In some examples, the one or more beams of light comprise, invisible light, visible light or near-infrared (NIR) light. In some examples OCT scanning generates one or more A-scans (amplitude modulation scans).

In another aspect of the present disclosure, quantitatively imaging a flow rate of a fluid in the target and a concentration of one or more analytes in the fluid in the target, and the determining rate of change of one more analyte concentrations use spectral analysis of the same A-scan. In some examples, amplitude, intensity or phase, of the same OCT A-scan, are used for determining a rate of change of the one or more analyte concentrations. In some examples, the flow rate, the concentration of one or more analytes, and the determining the rate of change or one or more analyte concentrations uses a plurality of OCT A-scans of the target.

In another aspect of the present disclosure, OCT is performed on a plurality of areas in the target. In some examples, one or more beams of light are used to perform multi-beam or multi-band scanning OCT. In some examples, a light source used for the illuminating is configured to have a power of at most 1.0 mW. In some examples, one or more beams of light illuminate the target concurrently or sequentially. In some examples, quantitatively imaging a flow rate of a fluid in the target and a concentration of one or more analytes in the fluid in the target occur substantially simultaneously. In some examples, one or more beams of light illuminate the target in a circular pattern or two or more concentric circular patterns.

In another aspect of the disclosure, the target is selected from the group consisting of tissue, healthy tissue, diseased tissue, retina, tumor, cancer, growth, fibroid, lesion, skin, mucosal lining, organ, graft, blood supply and one or more blood vessels. In some examples, quantitatively imaging a flow rate of a fluid in the target is performed using near-infrared (NIR) light. In some examples, quantitatively imaging a concentration of one or more analytes in the fluid in the target is performed using visible light.

In another aspect of the disclosure, the fluid may include but is not limited to whole blood, blood plasma, blood serum, urine, semen, tears, sweat, saliva, lymph fluid, pleural effusion, peritoneal fluid, meningal fluid, amniotic fluid, glandular fluid, spinal fluid, conjunctival fluid, vitreous, aqueous, vaginal fluid, bile, mucus, sputum and cerebrospinal fluid. In another aspect of the disclosure, the analyte is selected from the group consisting of oxygen, hemoglobin, oxygenated hemoglobin, deoxygenated hemoglobin, glucose, sugar, blood area nitrogen, lactate, hematocrit, biomarker and nucleic acid.

In another aspect of the disclosure, determining the rate of change of one or more analytes is performed by comparing or using a reference. In some examples, the reference is healthy tissue. In some examples, the reference is the target in which the flow rate of a fluid and the concentration of one or more analytes have been previously been quantified. In some examples, one or more images of the target are generated. In some examples, the one or more images and the change in rate of analyte concentration are used to calculate a function of the target or a change in the function of the target. In some examples, the function of the target is a pathological alteration in a tissue. In some examples, the function of the target is metabolic function. In some examples, arteries and veins are determined in the one or more images. In some examples, the metabolic function is calculated in one or more areas of the target. In another aspect of the disclosure, an exogenous agent is contacted with the target. In some examples, the exogenous agent is a contrast reagent. In some examples, the quantifying a flow rate of a fluid in the target comprises determining the cross sectional area of one or more vessels containing the fluid.

In another aspect of the disclosure, a medical decision is made by determining the rate of change of the one or more analyte concentrations in the target.

In another aspect of the disclosure, spectral analysis is performed to extract a full set of optical properties of the target.

In another aspect of the disclosure, the method is configured for a device selected from the group consisting of probe, handheld device, wearable device, endoscope, catheter probe, laparoscopic tool, surgical tool, and needle.

Another aspect of the disclosure provides determining a status of one or more molecular markers comprises calculating metabolic activity or a change in metabolic activity in the target. In some examples, determining a status of one or more molecular markers in a bodily fluid in the target is performed by measuring an intensity, amplitude or phase of visible light reflected at a plurality of depths for each of a plurality of areas generated. In some examples, quantifying flow of the bodily fluid includes measuring an intensity, amplitude or phase of NIR light reflected at a plurality of depths for each of a plurality of areas generated.

In another aspect of the disclosure, one or more A-scans are obtained. In some examples, flow rate and the status of one or more molecular markers are determined using spectral analysis of the same A-scan. In some examples, the providing a medical decision includes stratifying one or more treatment decision options in a report based on the status of the one or more molecular markers. In some examples, the medical decision is administration of a drug. In some examples, the target is selected from the following group: diseased tissue, suspected diseased tissue and healthy tissue. In some examples, the medical decision is changing the dosage of a drug, selecting a frequency of drug administration, or making a drug selection. In some examples, the determining a status of one or more molecular markers in a bodily fluid in the target, while simultaneously quantifying flow of the bodily fluid indicates the presence or absence of disease. In some examples, the target is selected from the group consisting of tissue, healthy tissue, diseased tissue, retina, tumor, cancer, growth, fibroid, lesion, skin, mucosal lining, organ, graft, blood supply and one or more blood vessels. In some examples, determining the status of one or more molecular markers includes imaging a blood flow or a blood supply. In some examples, the imaging includes comparing the image of the blood flow or the blood supply of a disease or suspected diseased tissue to an image of a blood flow or a blood supply from a normal tissue or a previous image of a blood flow or a blood supply from the same tissue; and diagnosing the diseased tissue if the image of the blood flow or the blood supply of the suspected diseased tissue includes an increased or an abnormal levels of one or more molecular markers when compared to the levels of molecular markers in an image of the blood flow or the blood supply from the normal tissue or a previous image of a blood flow or a blood supply from the same tissue.

In another aspect of the disclosure, the target is tissue suspected to include cancer. In some examples, cancer is selected from the group consisting of skin cancer, lung cancer, colon cancer, esophageal cancer, stomach cancer, ovarian cancer, thyroid cancer heart cancer, squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, liver cancer, brain cancer, prostate cancer, leukemia, melanoma, or lymphoma.

Another aspect of the disclosure provides determining a status of one or more molecular markers is used to diagnose, monitor or treat ocular diseases selected from the group consisting of: age related macular degeneration (AMD), wet AMD, dry AMD, glaucoma, retinal vein occlusion, branched retinal vein occlusion and diabetic retinopathy. In some examples, determining a status of one or more molecular markers is performed without contacting at least one analyte with an exogenous reagent or label.

Another aspect of the disclosure provides a metabolic optical coherence tomography system comprising visible light illumination and near infra-red illumination of a target to determine both a blood flow rate and a change in a rate of oxygen saturation.

II. General Methods for Functional OCT (fOCT)

A. Terminology and OCT Methods

The terms "optical coherence tomography" and "OCT," described herein, generally refer to an interferometric technique for imaging samples, in some examples, with micrometer lateral resolution. This non-invasive optical tomographic imaging technique is used in variety of medical and industrial applications to provide cross-sectional or 3D images of a target.

The terms "functional OCT" and "fOCT," described herein, generally refer to a method of OCT imaging that provides for the acquisition of both structural (3D, tomographic and cross-sectional information) and functional information about a target, as described herein. In some examples, fOCT may be referred to as "visible-OCT" or "vis-OCT." Vis-OCT generally refers to a type of fOCT that comprises visible light.

fOCT may utilize any method of OCT. Generally, fOCT may be configured with an interferometer, as is the example for many other OCT methods. Light from a light source (for example, a broadband light source) is split (for example, by a beam-splitter) and travels along a sample arm (generally comprising the sample) and a reference arm (generally comprising a mirror). A portion of the light from the sample arm illuminates a target is reflected by the target. Light is also reflected from a mirror in the reference arm. (Light from the test arm and the reference arm is recombined, for example by the beam-splitter.) When the distance traveled by light in the sample arm is within a coherence length of the distance traveled by light in the reference arm, optical interference occurs, which affects the intensity of the recombined light. The intensity of the combined reflected light varies depending on the target properties. Thus, variations for the intensity of the reflectance measured are indications of the physical features or attributes of the target being imaged.

In some examples, the devices, methods and systems of the disclosure may utilize time-domain OCT, where the length of the reference arm can be varied (for example, by moving one or more reference mirrors). The reflectance observed as the reference arm distance changes indicates sample properties at different depths of the sample. In some examples, the length of the sample arm is varied instead of or in addition to the variation of the reference arm length. In some examples, the devices, methods and systems may utilize frequency-domain OCT, where the distance of the reference arm can be fixed, and the reflectance can then be measured at different frequencies. For example, the frequency of light emitted from a light source can be scanned across a range of frequencies or a dispersive element, such as a grating, and a detector array may be used to separate and detect different wavelengths. Fourier analysis can convert the frequency-dependent reflectance properties to distance-dependent reflectance properties, thereby indicating sample properties at different sample depths. In certain examples, OCT can show additional information or data not obtainable from other forms of imaging.

In some examples, the devices, methods and systems of the disclosure may utilize frequency-domain optical coherence tomography, where the reference and sample arms are fixed. Light from a broadband light source including a plurality of wavelengths is reflected from the sample and interfered with light reflected by the reference mirror/s. The optical spectrum of the reflected signal can be obtained. For example, the light may be input to a spectrometer or a spectrograph, comprising, for example, a grating and a detector array that detects the intensity of light at different frequencies.

Fourier analysis may be performed, for example, by a processor, and may convert data corresponding to a plurality of frequencies to that corresponding to a plurality of positions within the sample. Thus, data from a plurality of sample depths can be simultaneously collected without the need for scanning of the reference arm (or sample) arms. Additional details related to frequency domain optical coherence tomography are described in Vakhtin et al., (Vakhtin A B, Kane D J, Wood W R and Peterson K A. "Common-path interferometer for frequency-domain optical coherence tomography," Applied Optics. 42(34), 6953-6958 (2003)) and incorporated by reference herein.

Other methods of performing optical coherence tomography are possible. For example, in some examples of frequency domain optical coherence tomography, the frequency of light emitted from a light source varies in time. Thus, differences in light intensity as a function of time relate to different light frequencies. When a spectrally time-varying light source is used, a detector may detect light intensity as a function of time to obtain optical spectrum of the interference signal. The Fourier transform of the optical spectrum may be employed as described herein. The devices, methods and systems of the disclosure may utilize any method of OCT, including but not limited to spectral domain OCT, Fourier domain OCT, time encoded frequency domain OCT, or swept source OCT, single point OCT, confocal OCT, parallel OCT, or full field OCT as known in the art.

Generally, the term "A-scan" OR "A-line" describes the light reflectivity associated with different sample depths. The term "B-scan" or "B-line" as used herein refers to the use of cross-sectional views of tissues formed by assembly of a plurality of A-scans. In the example of fOCT methods of cancer detection, light reflected by cancerous tissue target is converted into electrical signals and can be used to generate both cross-sectional or 3D structural images and metabolic functional information about the target tissue (such as cancerous growth, lesion, or tumor). In the example of ophthalmology, light reflected by eye tissues is converted into electrical signals and can be used to provide data regarding the 3D structure of tissue in the eye and metabolic activity in the retina. In many examples, including but not limited to cancer detection and ophthalmology, A-scans and B-scans can be used, for example, for differentiating normal and abnormal tissue.

For general methods, an A-scan can generally include data at plurality of depths in a z-axis direction, and a B-scan may include cross-sectional data from a medial border to a lateral border, or (x,y) axis direction. In the example of fOCT of a skin cancer lesion, for example, an A-scan can generally include data from the outer regions of the epidermis of the lesion to the inner regions comprising vasculature, while B-scans can include cross sectional data from one lesion border to another in the (x,y) plane. In ophthalmic instances, an A-scan can generally include data from the cornea to the retina, and a B-scan can include cross-sectional data from a medial border to a lateral border of the eye and from the cornea to the retina. 3D C-scans may be used to generate one or more 3D images by combining a plurality of B-scans in variety of examples.

In the present disclosure, a "target" may indicate any sample, object, or subject suitable for imaging. In some examples, a target may include but is not limited to inanimate material such as metals, alloys, polymers, and minerals as found for industrial applications for fOCT and as described herein. In some examples, a target may be animate material, such any suitable living material including but not limited to embryos, seeds, cells, tissues, grafts, blood vessels, organs, or organisms as would be suitable for medical and agricultural applications for fOCT as described herein.

B. fOCT System Configuration

A fOCT system for data collection may be configured in a variety of ways, generally suitable with any type of OCT. FIG. 1 and FIG. 2(a) illustrate an example of data generated by an example system 200 configured for metabolic imaging. The example free-space vis-OCT system 200 includes lens L1 202, lens L2 204, an x-y axis linear scanning mirror unit 206 (e.g., a pair of rotatable mirrors to steer the laser beam such as piezo-driven galvo mirrors (GM) or other rotation mechanisms such as resonance scanning mirrors, etc.), beam-splitter 208, dispersion control (DC) 210, reference mirror (REF) 212, laser 214 (e.g., generated by a supercontinuum source such as a continuous wave (CW) argon-ion laser, etc.), charge-coupled device (CCD) camera 216 (e.g., a two-dimensional CCD or other detector such as a CMOS camera, etc.), and computer or other processor 218.

Lenses L1 202 and L2 204 relay a beam generated by the laser 214 onto a target pupil 220. The beam-splitter 208 works with a reference arm including reference mirror 212 with dispersion control 210 to adjust the beam from the laser 214. The beam is directed by the mirrors 206 through the lenses 202, 204 to impact the pupil 220. Resulting image information is captured by the CCD 216 and relayed to the computer 218. The computer 218 can be used to control the CCD 216 and/or other components of the system 200, for example.

Figure 2C:
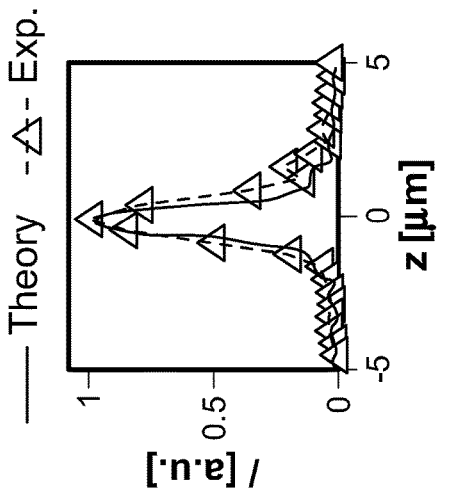
FIG. 2c is an example of theoretical and axial resolutions of a free space vis-OCT device.
Figure 2A:
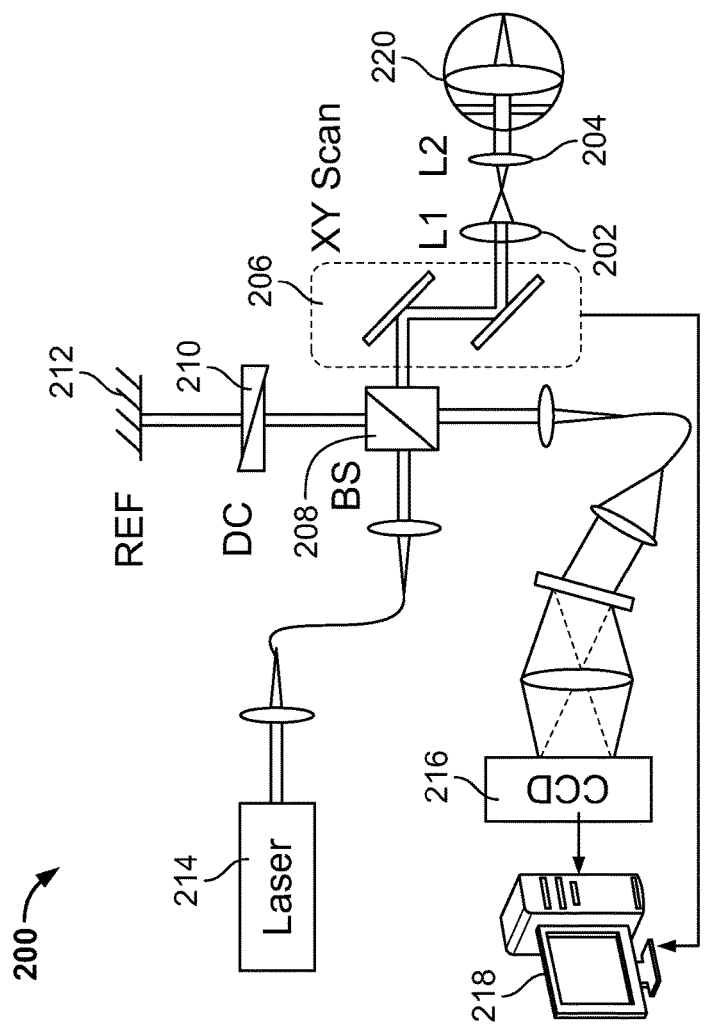
FIG. 2a is an example schematic of a free space vis-OCT device.

FIG. 2(b) illustrates an example illumination spectrum obtained using the system 200. FIG. 2(c) shows a comparison of theoretical and experimental axial resolutions obtained using the example system 200.

Figure 20:
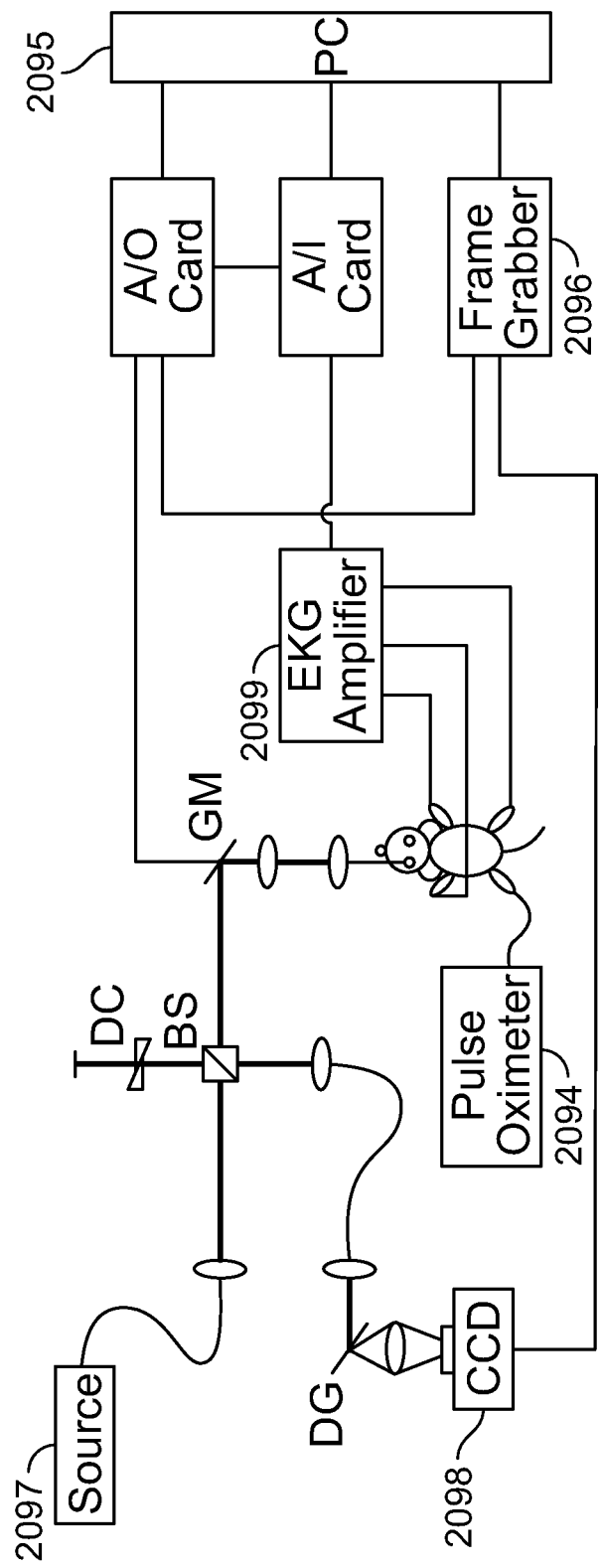
FIG. 20 is a schematic of an example vis-OCT device.
Figure 21A:
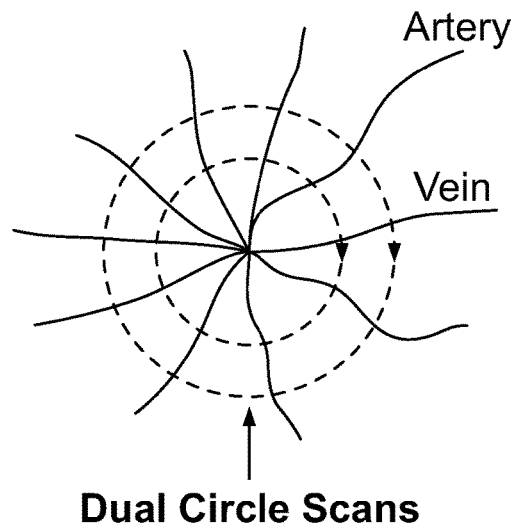
FIG. 21a is a representation of an example scanning pattern schematic for flow measurement. Two concentric circular scans crossed all blood vessels originating from the optic disk.
Figure 21B:
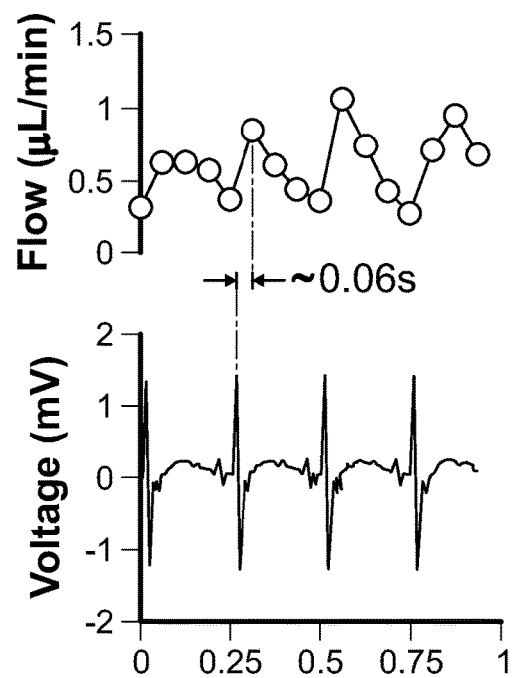
FIG. 21b is a graph of example pulsatile flow patterns with the simultaneous EKG pattern.
Figure 21C:
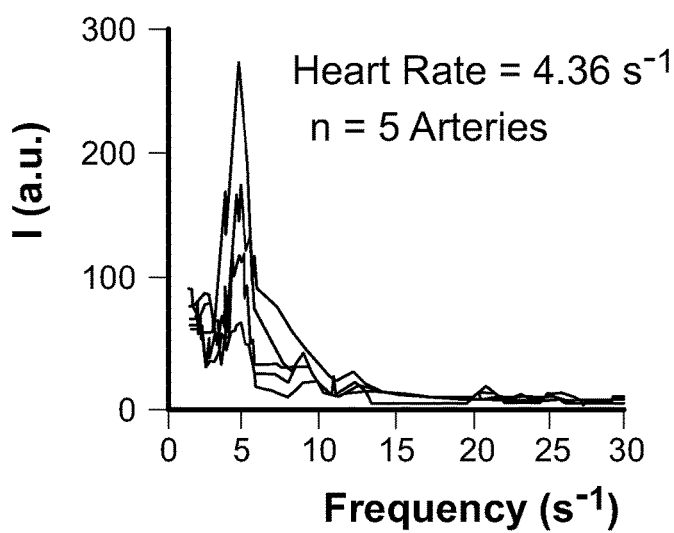
FIG. 21c is a graph of an example Fourier transform of the pulsatile flow pattern.
Figure 21D:
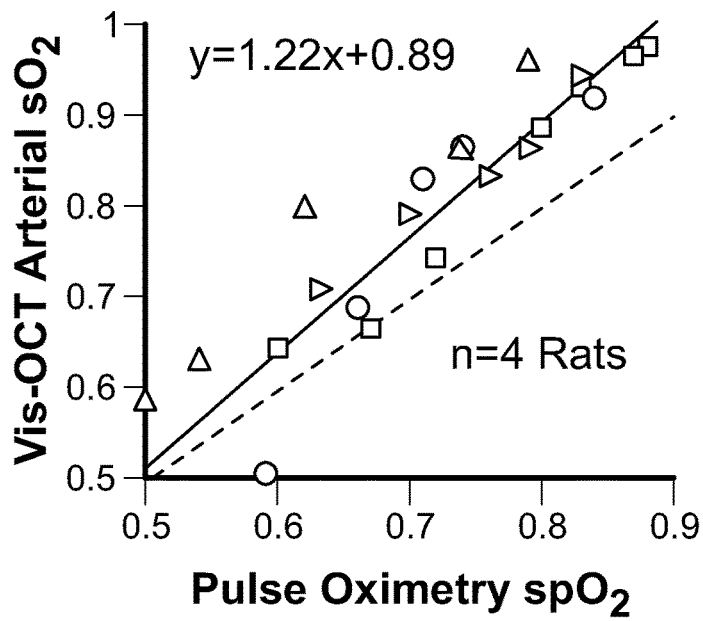
FIG. 21d is a graph showing example correlation of arterial $sO_2$ measurement by vis-OCT and $spO_2$ (pulse oximetry).
Figure 21E:
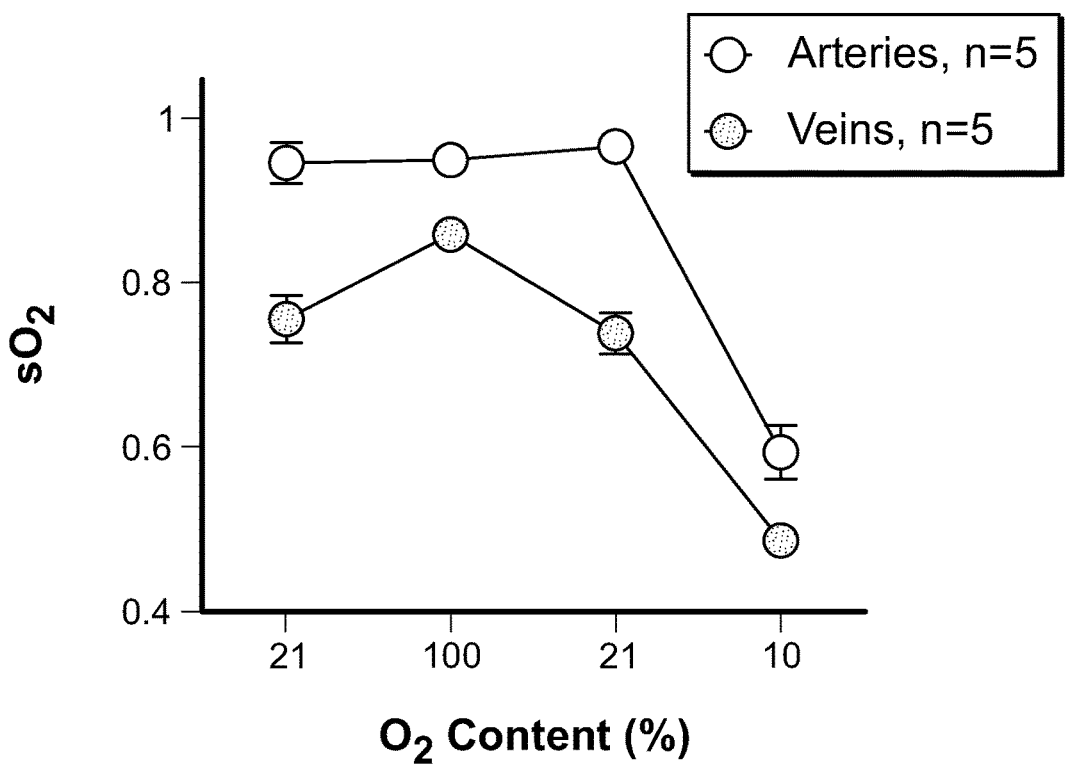
FIG. 21e is a graph of example arterial and venous $sO_2$ response to the changing oxygen content of the inhaled air.

FIG. 20 provides another example of a fOCT or vis-OCT configuration. In some examples, a supercontinuum source, 2097 is used for illumination of a target. In some examples an open-space Michelson interferometry configuration may be adopted due to the minimum dispersion. The beam may also be collimated and split by a cube beam splitter into the reference and sample arms. The sample arm may contain a two-dimensional galvo mirror to steer the beam, and, optionally, a 0.2 magnification Keplerian telescope to relay the beam from the galvo mirror to the target. The reference arm may include a dispersion control glass plate, and a mirror to illustrate the beam. The two beams from the reference and sample arms recombined at the beam splitter and may be collected by an optical fiber. The fiber may deliver the light to a spectrometer, which may consist of a collimating lens, a diffraction grating, an objective lens, and a line scan CCD camera, 2098 (e.g. Balser, sprint slp2k). The camera exposure and the scanning galvo mirror may be synchronized by an analog output card.

The devices, methods, compositions, systems, and kits of the present disclosure may use any light source suitable for OCT, including but not limited to supercontinuum lasers, superluminescent diodes, continuous wave lasers or ultra-short pulsed lasers. The light source may be used to generate one or more low coherence beams of light to illuminate the target. In some examples, the light source may be used to generate a range of beams of light. In some examples, the light source may generate between 1 and 10 beams. In other examples, the light source may generate between 2 and 5 beams. In other examples, the light source may generate between 5 and 20 beams. In other examples, the light source may generate between 10-15 beams. In other examples, the light source may generate between 1 and 1000 beams of light. In other examples, the light source may generate between 10 and 1000 beams of light. In other examples, the light source may generate between 20 and 100 beams of light. In other examples, the light source may generate between 30 and 100 beams of light. In other examples, the light source may generate between 40 and 100 beams of light. In other examples, the light source may generate between 50 and 100 beams of light. In other examples, the light source may generate between 60 and 1000 beams of light. In other examples, the light source may generate between 70 and 100 beams of light. In other examples, the light source may generate between 1 and 80 beams of light. In other examples, the light source may generate between 90 and 100 beams of light. Those of skill in the art will appreciate that the number of beams of light may fall within any range bounded by any of these values (e.g. from about 1 beam to about 1000 beams).

Generally, the wavelength range of the one or more beams of light may range from about 500 nm to about 620 nm. In some examples, the wavelength may range between 200 nm to 600 nm. In some examples, the wavelength may range between 300 to 900 nm. In some examples, the wavelength may range between 500 nm to 1200 nm. In some examples, the wavelength may range between 500 nm to 800 nm. In some examples, the wavelength range of the one or more beams of light may have wavelengths at or around 500 nm, 510 nm, 520 nm, 530 nm, 540 nm, 550 nm, 560 nm, 570 nm, 580 nm, 590 nm, 600 nm, 610 nm, and 620 nm. Generally, the wavelength range of the one or more beams of light may range from 200 nm to 1500 nm. In some examples, the wavelength range of the one or more beams of light may range from 200 nm to 1500 nm. The wavelength range of the one or more beams of light may range from 300 nm to 1500 nm. The wavelength range of the one or more beams of light may range from 400 nm to 1500 nm. The wavelength range of the one or more beams of light may range from 500 nm to 1500 nm. The wavelength range of the one or more beams of light may range from 600 nm to 1500 nm. The wavelength range of the one or more beams of light may range from 700 nm to 1500 nm. The wavelength range of the one or more beams of light may range from 800 nm to 1500 nm. The wavelength range of the one or more beams of light may range from 900 nm to 1500 nm. The wavelength range of the one or more beams of light may range from 1000 nm to 1500 nm. The wavelength range of the one or more beams of light may range from 1100 nm to 1500 nm. The wavelength range of the one or more beams of light may range from 1200 nm to 1500 nm. The wavelength range of the one or more beams of light may range from 1300 nm to 1500 nm. The wavelength range of the one or more beams of light may range from 1300 nm to 1500 nm. In some examples, fOCT and devices, methods, and systems of the present disclosure include two or more beams of light with wavelengths in the visible light spectrum or the near infrared (NIR) light spectrum. In some examples, fOCT includes beams of light with wavelengths in the visible light spectrum and the NIR spectrum. Those of skill in the art will appreciate that the wavelength of light may fall within any range bounded by any of these values (e.g. from about 200 nm beam to about 1500 nm).

In some examples, fOCT may include multi-band scanning. In some examples a band may include one or more wavelength ranges containing continuous wavelengths of light within a bounded range. In some examples a band may include one or more wavelength ranges containing continuous group of wavelengths of light with an upper limit of wavelengths and a lower limit of wavelengths. In some examples, the bounded ranges within a band may include the wavelength ranges described herein. In some examples fOCT may include bands that overlap. In some examples, fOCT may include bands are substantially separated. In some examples, bands may partially overlap. In some examples, fOCT may include one or more bands ranging from 1 band to 100 bands. In some the number of bands may include 1-5 bands. In some the number of bands may include 5-10 bands. In some the number of bands may include 10-50 bands. In some the number of bands may include 25-75 bands. In some the number of bands may include 25-100 bands.

Generally, one or more beams of light used to illuminate a target may be configured in any suitable pattern. In some examples, the beams of light may be one or more polygon patterns. In some examples the illumination pattern 600, (FIG. 6) may be rectangle of one or more beams, 610, 620. In some examples, the beams of light may illuminate the target as one or more circles, (FIG. 3) or two or more concentric circles 395, with one or more beams, 396, and 397. In some examples, a suitable pattern may be chosen based upon the pattern of vessels or fluid flow to be imaged in a target. For example, in a retina, blood vessels are found radially around the optic nerve head in a circular pattern or substantially circular pattern. For example, for fOCT imaging of a retina, one or more concentric circles of beams, or substantially circular beams, may be used to illuminate the target retina. In some examples, fOCT may be performed with a identical or different predefined scanning trajectory. In some examples the trajectory may include a polygonal shape. In some examples, the trajectories may be applied to a target simultaneously or sequentially.

Further, the devices, methods, and systems of the disclosure may allow for various power requirements to generate fOCT scans as compared to other OCT or imaging methods. In some examples, an fOCT device is configured to illuminate a target with a light source with a range of power from 0.01 mW to 100 mW. In some examples, a fOCT device is configured to illuminate a target with a light source of about 0.8 mW. In some examples, a fOCT device is configured to illuminate a target with a light source of about 0.5 mW-0.8 mW. In some examples, a fOCT device is configured to illuminate a target with a light source of about 0.1 mW-1.2 mW. In some examples, a fOCT device is configured to illuminate a target with a light source of about 0.2 mW-1.5 mW. In some examples, a fOCT device is configured to illuminate a target with a light source with a power ranging from 0.01 mW to 1 mW. In some examples, a fOCT device is configured to illuminate a target with a light source with a power ranging from 0.02 mW to 1 mW. In some examples, a fOCT device is configured to illuminate a target with a light source with a power ranging from 0.03 mW to 1 mW. In some examples, a fOCT device is configured to illuminate a target with a light source with a power ranging from 0.04 mW to 1 mW. In some examples, a fOCT device is configured to illuminate a target with a light source with a power ranging from 0.05 mW to 1 mW. In some examples, a fOCT device is configured to illuminate a target with a light source with a power ranging from 0.06 mW to 1 mW. In some examples, a fOCT device is configured to illuminate a target with a light source with a power ranging from 0.07 mW to 1 mW. In some examples, a fOCT device is configured to illuminate a target with a light source with a power ranging from 0.08 mW to 1 mW. In some examples, a fOCT device is configured to illuminate a target with a light source with a power ranging from 0.09 mW to 1 mW. In some examples, a fOCT device is configured to illuminate a target with a light source with a power ranging from 0.1 mW to 1 mW. In some examples, a fOCT device is configured to illuminate a target with a light source with a power ranging from 0.2 mW to 1 mW. In some examples, a fOCT device is configured to illuminate a target with a light source with a power ranging from 0.3 mW to 1 mW. In some examples, a fOCT device is configured to illuminate a target with a light source with a power ranging from 0.4 mW to 1 mW. In some examples, a fOCT device is configured to illuminate a target with a light source with a power ranging from 0.5 mW to 1 mW. In some examples, a fOCT device is configured to illuminate a target with a light source with a power ranging from 0.6 mW to 1 mW. In some examples, a fOCT device is configured to illuminate a target with a light source with a power ranging from 0.7 mW to 1 mW. In some examples, a fOCT device is configured to illuminate a target with a light source with a power ranging from 0.8 mW to 1 mW. In some examples, a fOCT device is configured to illuminate a target with a light source with a power ranging from 0.9 mW to 1 mW. In some examples, a fOCT device is configured to illuminate a target with a light source with a power ranging from 1.0 mW to 100 mW. In some examples, a fOCT device is configured to illuminate a target with a light source with a power ranging from 2.0 mW to 100 mW. In some examples, a fOCT device is configured to illuminate a target with a light source with a power ranging from 3.0 mW to 100 mW. In some examples, a fOCT device is configured to illuminate a target with a light source with a power ranging from 4.0 mW to 100 mW. In some examples, a fOCT device is configured to illuminate a target with a light source with a power ranging from 5.0 mW to 100 mW. In some examples, a fOCT device is configured to illuminate a target with a light source with a power ranging from 10.0 mW to 100 mW. In some examples, a fOCT device is configured to illuminate a target with a light source with a power ranging from 20.0 mW to 100 mW. In some examples, a fOCT device is configured to illuminate a target with a light source with a power ranging from 30.0 mW to 100 mW. In some examples, a fOCT device is configured to illuminate a target with a light source with a power ranging from 50.0 mW to 100 mW. In some examples, a fOCT device is configured to illuminate a target with a light source with a power ranging from 75.0 mW to 100 mW. Those of skill in the art will appreciate that light source power may fall within any range bounded by any of these values (e.g. from about 0.01 mW to about 100 mW).

In some examples, the devices, methods, and systems of the disclosure allow for configuration of an fOCT device to acquire A-scans at a faster rate than other OCT or imaging methods. In some examples, A-scan acquisition rate may range from 1 kHz to 10,000 kHz. In some examples, A-scan acquisition rate may range from 5 kHz to 1000 kHz. In some examples, A-scan acquisition rate may range from 10 kHz to 1,000 kHz. In some examples, A-scan acquisition rate may range from 20 kHz to 1,000 kHz. In some examples, A-scan acquisition rate may range from 30 kHz to 1000 kHz. In some examples, A-scan acquisition rate may range from 40 kHz to 1,000 kHz. In some examples, A-scan acquisition rate may range from 50 kHz to 1000 kHz. In some examples, A-scan acquisition rate may range from 60 kHz to 1,000 kHz. In some examples, A-scan acquisition rate may range from 70 kHz to 1000 kHz. In some examples, A-scan acquisition rate may range from 80 kHz to 1,000 kHz. In some examples, A-scan acquisition rate may range from 90 kHz to 1000 kHz. In some examples, A-scan acquisition rate may range from 100 kHz to 1,000 kHz. In some examples, A-scan acquisition rate may range from 200 kHz to 1000 kHz. In some examples, A-scan acquisition rate may range from 300 kHz to 1,000 kHz. In some examples, A-scan acquisition rate may range from 400 kHz to 1000 kHz. In some examples, A-scan acquisition rate may range from 500 kHz to 1,000 kHz. In some examples, A-scan acquisition rate may range from 600 kHz to 1000 kHz. In some examples, A-scan acquisition rate may range from 700 kHz to 1,000 kHz. In some examples, A-scan acquisition rate may range from 800 kHz to 1000 kHz. In some examples, A-scan acquisition rate may range from 900 kHz to 1,000 kHz. In some examples, A-scan acquisition rate may range from 1000 kHz to 10000 kHz. In some examples, A-scan acquisition rate may range from about 35 kHz to about 70 kHz. In some examples, A-scan acquisition rate may range from about 20 kHz to about 100 kHz. In some examples, A-scan acquisition rate may range from about 75 kHz to about 200 kHz. In some examples, A-scan acquisition rate may range from about 100 kHz to about 500 kHz. In some examples, A-scan acquisition rate may include a frequency of 10 kHz, 15 kHz, 20 kHz, 25 kHz, 30 kHz, 35 kHz, 40 kHz, 45 kHz, 50 kHz, 60 kHz, 70 kHz, 75 kHz, 80 kHz, 85 kHz, 90 kHz, or 100 kHz. Those of skill in the art will appreciate that A-scan acquisition frequency may fall within any range bounded by any of these values (e.g. from about 1 kHz to about 10000 kHz).

Each B-scan may have a plurality of A-scans, ranging from 1 to 1000. In some examples, each B-scan may have a range of 1-10,000 A-scans. In some examples, each B-scan may have a range of 10-1000 A-scans. In some examples, each B-scan may have a range of 100-1000 A-scans. In some examples, a B-can may have 256 A-scans. In some examples, each B-scan may have a range of 200-1000 A-scans. In some examples, each B-scan may have a range of 300-1000 A-scans. In some examples, each B-scan may have a range of 400-1000 A-scans. In some examples, each B-scan may have a range of 500-1000 A-scans. In some examples, each B-scan may have a range of 600-1000 A-scans. In some examples, each B-scan may have a range of 700-1000 A-scans. In some examples, each B-scan may have a range of 800-1000 A-scans. In some examples, each B-scan may have a range of 900-1000 A-scans. In some examples, each B-scan may have a range of 1000-10000 A-scans. In some examples, each B-scan may have a range of 2000-10000 A-scans. In some examples, each B-scan may have a range of 3000-10000 A-scans. In some examples, each B-scan may have a range of 4000-10000 A-scans. In some examples, each B-scan may have a range of 5000-10000 A-scans. In some examples, each B-scan may have a range of 6000-10000 A-scans. In some examples, each B-scan may have a range of 7000-10000 A-scans. In some examples, each B-scan may have a range of 8000-10000 A-scans. In some examples, each B-scan may have a range of 9000-10000 A-scans. In some examples a B-scan may include 2410 A-scans. In some examples a B-scan may include 2500 A-scans.

In some examples, fOCT may be performed with a range of 1-100,000,000 A-scans generated for quantitatively 3D-imaging in the target. In some examples, A-scans generated may range from 100-100,000,000. In some examples, A-scans generated may range from 1000-100,000,000. In some examples, A-scans generated may range from 10000-100,000,000. In some examples, A-scans generated may range from 100000-100,000,000. In some examples, A-scans generated may range from 1000000-100,000,000. In some examples, A-scans generated may range from 10,000,000-100,000,000. In some examples, about 65,000 A-scans are generated for quantitatively 3D-imaging in the target. In some examples, about 50,000 A-scans are generated for quantitatively 3D-imaging in the target. In some examples, about 75,000 A-scans are generated for quantitatively 3D-imaging in the target. In some examples, about 25,000 A-scans are generated for quantitatively 3D-imaging in the target.

In some examples, an electrocardiogram (EKG) amplifier to collect an EKG signal may be used in addition to fOCT imaging. In some examples, an EKG signal may be useful when configuring a fOCT device for metabolic imaging of blood vessels, such as shown in FIG. 20, 2099. The EKG signal collection may be synchronized with the scanning by an analog output card, so that the collections of EKG and the OCT image are simultaneous. In some examples, a pulse oximeter may also be used with fOCT, as shown in FIG. 20, 2094. In some examples, a frame grabber is used with fOCT, as shown in FIG. 20, 2096. In some examples, a PC processor, 2095, or machine can be configured with fOCT. In some examples, a PC computer processor may include but is not limited to a personal computer, mainframe, cell phone, mobile device, wearable device, or watch.

C. fOCT Signal Processing and Quantification

The devices, methods, and systems of the disclosure provide for quantitatively 3D-imaging in the target, a flow rate of a fluid and a concentration of one or more analytes, from the optical information acquired in previous steps and as described herein. In some examples, optical information is extracted from A-scans. Unlike previously described imaging methods, data sufficient for quantitatively 3D-imaging in the target, a flow rate of a fluid and a concentration of one or more analytes may be extracted from only optical information generated by OCT. Additionally, quantitatively 3D-imaging in the target, a flow rate of a fluid and a concentration of one or more analytes may be extracted from the same optical information. In some examples, the same optical information may be the same A-scan. In some examples, information from a single or same A-scan may be used to quantitatively 3D-image in a target, a flow rate of a fluid and a concentration of one or more analytes. In some examples, both quantitatively 3D-imaging in the target, a flow rate of a fluid and a concentration of one or more analytes occurs simultaneously or substantially simultaneously. In some examples, simultaneously (or substantially simultaneously given some data transmission, storage, and/or processing latency, etc.) may refer to concurrent (or substantially concurrent given some data transmission, storage, and/or processing latency, etc.) calculations. In some examples, simultaneously may refer to both quantitatively 3D-imaging in the target, a flow rate of a fluid and a concentration of one or more analytes occurring in the same system, in the same target, with the same OCT device, or with the same algorithmic processor.

i. 3D-Imaging

Figure 14:
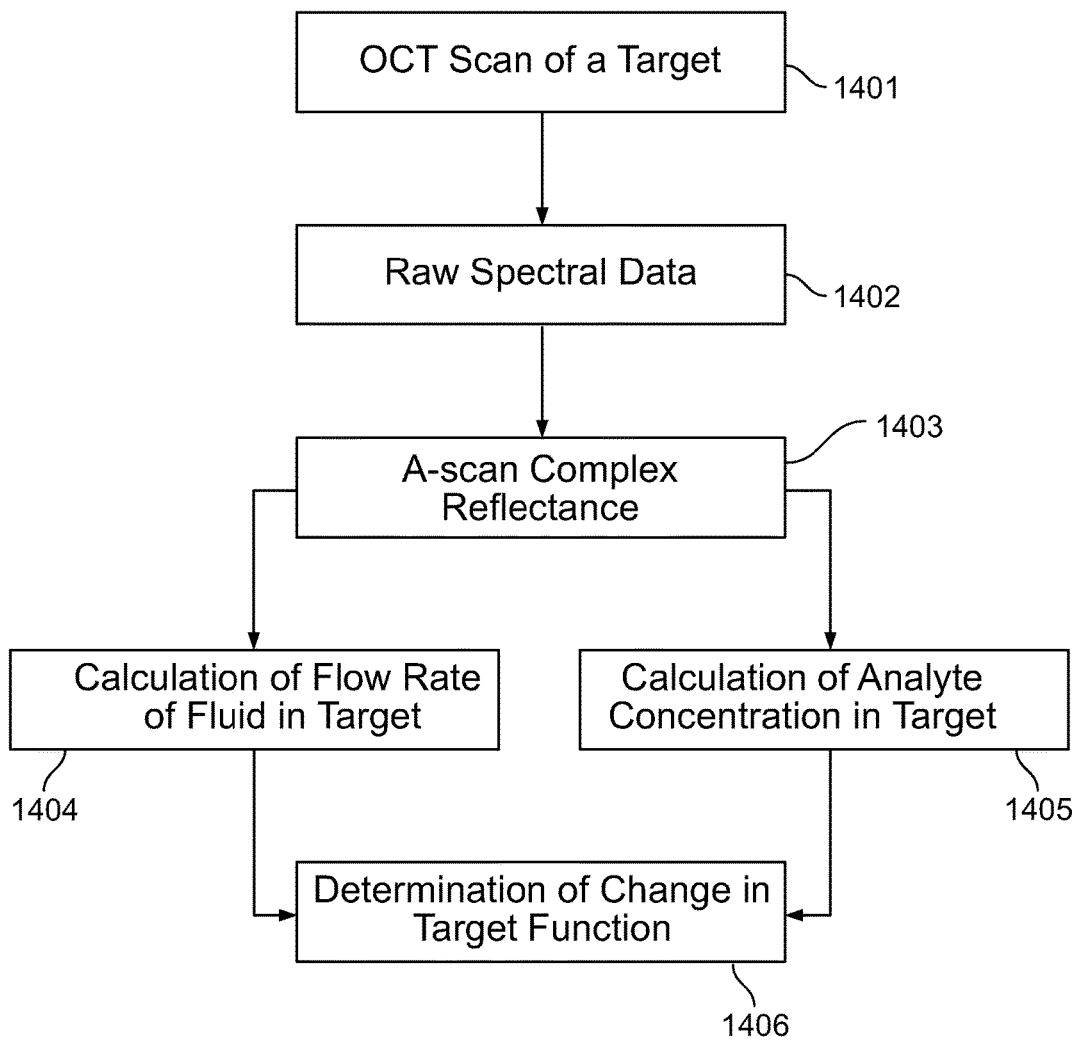
FIG. 14 is a flow schematic for an example process of quantitatively 3D-imaging in the target, a flow rate of a fluid and a concentration of one or more analytes, from optical information acquired and determining a rate of change of the one or more analyte concentrations in the target.
Figure 15A:
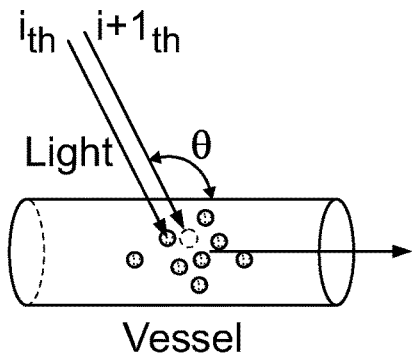
FIG. 15a is a diagram showing an example flow contrast of moving cells. The phase shift of the complex reflectance signal is proportional to the flow velocity projected to the light beam.
Figure 15B:
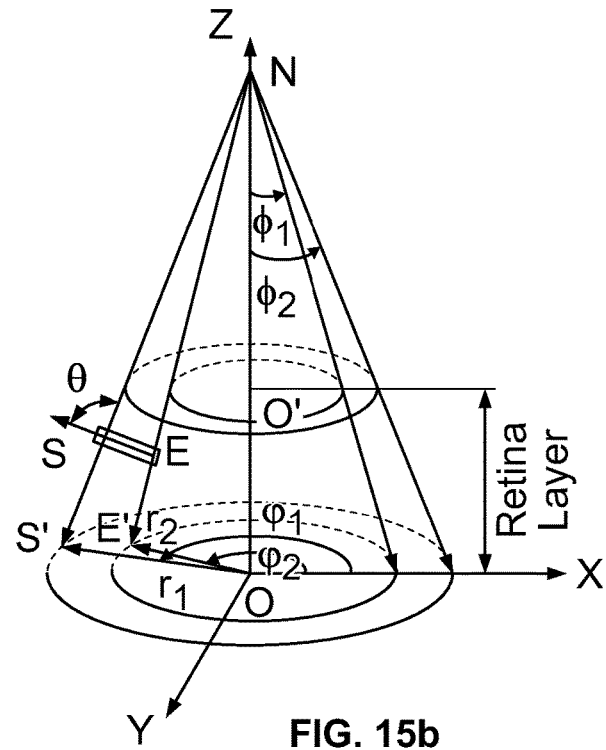
FIG. 15b is a schematic of an example geometry for calculating a Doppler angle.
Figure 15C:
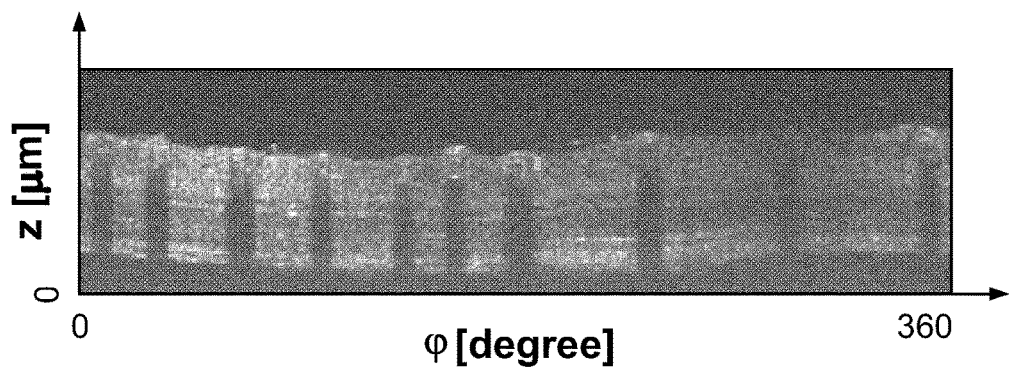
FIG. 15c is an example B-scan.
Figure 15D:
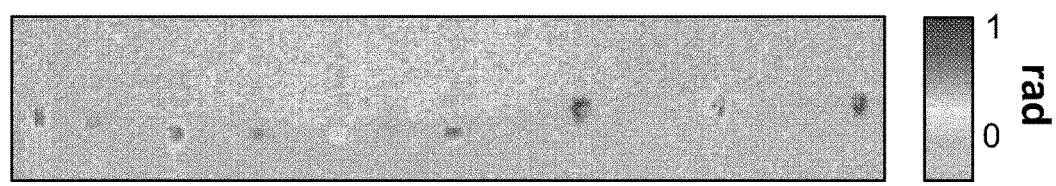
FIG. 15d is an example of a phase shift B-scan.

FIG. 14 provides an example process scheme of methods for signal processing quantification for quantitatively 3D-imaging in a target, a flow rate of a fluid and a concentration of one or more analytes. In certain examples, one or more OCT scans, 1401, are obtained. Raw spectral data is then obtained from one or more OCT scans, 1402. A-scan complex reflectance is then obtained, 1403. From the same A-scan complex reflectance, the devices, methods and systems of the disclosure provide for calculation of flow rate of fluid in target, 1404, and calculation of one or more analyte concentration in a target, 1405. A determination of change in target function, 1406, may be performed based on the calculation of flow rate of fluid in target.

Before down stream quantification process elements, in some examples, one or more exposures of a CCD camera configured with the fOCT device may record the interferometric spectrum. In some examples, a process element is performed before A-scans are obtained. In some examples, DC spectral background may be averaged from a portion or the entirety of the spectral signals. The remaining spectrum may be resampled into k-space with an equal interval. The complex reflectance signal with respect to depth ("A-line" or "A-scan") may be obtained by a fast Fourier transform (FFT) on the k-space spectrum. The process may be repeated for all or a portion of collected A-lines described herein. Fast Fourier transforms (FFT) or any suitable methods to generate 3D complex reflectance data may be used. In some examples, the amplitude of the complex reflectance may be used to obtain 3D morphological images.

ii. Quantifying Analyte Concentration

The devices, methods, and systems of the disclosure provide for signal processing that provides one or more analyte concentrations to be quantified from 3D-images generated by fOCT and as described herein. Generally, the method includes: 3D image vessel segmentation, spectral extraction, and fitting.

In some examples, vessels containing a fluid can be segmented or identified by intensity thresholding. In some examples, vessels include but are not limited to blood vessels. In some examples, an intensity histogram adjustment may be performed on each B-scan image to maximize contrast. Next, a global image threshold may be calculated using Otsu's methods and used to binarize one or more images. In some examples, the depth location of the first non-zero boundary from each A-scan may be recorded as the surface at that point. The same procedure may be repeated on all or a portion of the B-scans generated and described herein.

The transverse coordinates of the vessels may then be located. A mean intensity projection from a slab around 150 to 200 f·m deep from the surface may be taken. In some examples, a slab can range from 1 f·m to 10000 f·m. In some examples, a slab can range from 100 f·m to 400 f·m. In some examples, a slab can range from 100 f·m to 900 f·m. In some examples, a slab can range from 200 f·m to 800 f·m. In some examples, a slab can range from 300 f·m to 700 f·m. In some examples, a slab can range from 400 f·m to 600 f·m. In some examples, a slab can range from 200 f·m to 600 f·m. In some examples, a slab can range from 100 f·m to 10000 f·m. In some examples, a slab can range from 200 f·m to 10000. In some examples, a slab can range from 300 f·m to 10000. In some examples, a slab can range from 400 f·m to 10000. In some examples, a slab can range from 500 f·m to 10000. In some examples, a slab can range from 600 f·m to 10000. In some examples, a slab can range from 600 f·m to 10000. In some examples, a slab can range from 700 f·m to 10000. In some examples, a slab can range from 800 f·m to 10000. In some examples, a slab can range from 900 f·m to 10000. In some examples, a slab can range from 1000 f·m to 10000. In some examples, a slab can range from 1200 f·m to 10000. In some examples, a slab can range from 1300 f·m to 10000. In some examples, a slab can range from 1400 f·m to 10000. In some examples, a slab can range from 1500 f·m to 10000

Next, an adaptive thresholding procedure may be used to binarize the image. In order to remove the noise, image dilation and erosion processing may be performed on the binarized image with a 3 pixel-radian disk pattern. Each vessel may then be separated and selected individually. The 3D coordinates (axial and transverse) of the vessels may then be recorded to further extract the spectrum from these vessels.

After the 3D coordinates of each blood vessel may be determined, the corresponding interferometric spectra may be selected from the raw data and Short-time Fourier transform (STFT) may be performed for spectra extraction and fitting. Any suitable Gaussian window size may be applied. In some examples, $k_w=0.32$ f·m$-1$ (17 nm at 585 nm) may be used in the STFT. In some examples, relaxing the axial resolution to at least 9 f·m. or at most 9 f·m. may be used. The spectra may then be taken from the bottom of a vessel wall. Various spectral fitting models are known in the art.

Generally, an OCT signal can be modeled by different equations pertaining to an analyte. In some examples, an analyte may be oxygen, hemoglobin, deoxygenated hemoglobin or oxygenated hemoglobin. For example, to determine metabolic function in a retina, the following equation may be used to model oxygen consumption:

$$I^2 = I_0^2 R_0 r \exp[-2nd\ \mu_{HbO2}(sO_2) - 2nd\ \mu_{Hb}(1-sO_2)]$$

where $l_0$ is the incident intensity on the retina. In some examples, the optical attenuation by ocular lens and vitreous chamber can be ignored and thus $l_0$ may be considered the source spectrum; $R_0$ is the reference arm reflectance; d [mm] is the vessel diameter; r [dimensionless] is the reflectance at the vessel wall, whose scattering spectrum can be modeled as a power law under the first-order Born approximation r(A) AA where A is a constant. The optical attenuation coefficient f·1 [mm$^{-1}$] combines the absorption (f·la) and scattering coefficients (f·ls) of a fluid. In some examples, this may be for whole blood, which may be both wavelength- and oxygenation-dependent. In the example of oxygenated and deoxygenated hemoglobin, the subscripts Hb and HbO$_2$ denote the contribution from deoxygenated and oxygenated blood, respectively. A log linear regression of the data may then be used on the spectra to return the value of sO$_2$. A concentration of any suitable analyte may be quantitatively obtained through 3D-imaging in the target.

iii. Flow Quantification

Methods for quantifying a flow rate of fluid using OCT has been previously described and are known in the art. In some examples, phase sensitive Doppler OCT may be used for flow measurement. Phase is a type of high resolution position measurement of a reflection along the optical path length of the imaging system, which is cyclic of the frequency of half the wavelength of the imaging light. A depth position change of half the imaging wavelength will produce the same phase measurement. Changes in phase are proportional to the axial flow, the flow component parallel to the imaging direction designated by v(cos θ), where v is the velocity of the flow and θ is the angle between the flow direction and the imaging light.

In phase sensitive Doppler-OCT signals from two adjacent A-lines, FIG. 15, may be used to extract the velocity of a fluid, a velocity of an analyte in the fluid or fluid viscosity. In some examples, blood flow may be measured by determining the velocity of red blood cells. The blood flow velocity can be expressed as:

$$v = \frac{f_{sample} \cdot \lambda_0 \cdot \Delta\phi}{4 \cdot \pi \cdot n \cdot \cos(\theta)},$$

where $f_{sample}$ is the OCT A-line scanning frequency; $\lambda_0$ [nm] is the center wavelength of the light source; $\Delta\phi$ is the phase shift of the complex reflectance between adjacent A-scans [radians]; n is the refraction index of the sample; and e [radians] is the Doppler angle; the angle between the blood vessel and probing light. The velocity projected to the probe beam direction $v_p$ is proportional to $\Delta\phi$, $$v_p = \frac{f_{sample} \cdot \lambda_0 \cdot \Delta\phi}{4\pi n}$$

the total blood flow is equal to the product of the velocity and the vessel cross sectional:

$$F = v \times A = v \times \frac{\pi Dia^2}{4} \times \sin(\theta) = v_p \times \frac{\pi Dia^2}{4} \times \tan(\theta).$$

Thus, the post-processing for blood flow may include the following steps: calculation of the projected blood velocity $v_p$, Doppler angle θ, and vessel diameter Dia.

The devices, methods, and systems of the disclosure provide for utilizing the same optical information used to quantify one or more analyte concentrations for fluid flow calculations. The optical information, or in some examples, complex reflectance A-line signal from the Fourier transform of the interferometric spectra may be used. In some examples, the derivative of the phase term of the complex signal between the adjacent A-lines may be used in quantifying fluid flow in a vessel. In some examples, a median filter may be applied on one or more B-scan phase images to remove salt and pepper noise. $\Delta\phi$ is calculated by the integration of the phase shift within each vessel lumen.

In some examples, in order to calculate the Doppler angle, dual circle scans with radius $r_1$ and $r_2$ intersect a vessel at two different vessel center points, $S(x_1,y_1,z_1)$ and $E(x_2,y_2,z_2)$. The direction of the vessel can be expressed as a vector $\overline{ES}$:

$$\overline{ES} = x_1-x_2, y_1-y_2, z_1-z_2).$$

In the example of fOCT of a retina, the direction of probing light is NS', where N is the nodal point of the eye. If the eye diameter is h, then the coordinates of N are (0,0,h) and the coordinates of S' are $(x_1',y_1',0)$. The probing light direction is:

$$\overline{NS'} = (x_1', y_1', -h).$$

The Doppler angle θ can then be calculated given the coordinates of all the vectors:

$$\cos(\theta) = \frac{\overline{ES} \cdot \overline{NS'}}{|\overline{ES}| \cdot |\overline{NS'}|},$$

where $r_1$ and $r_2$ are the radii of the outer and inner circular scans on retina respectively, and <1 and <2 are the azimuthal angles of the circular scans. The z coordinates may be measured directly from the B-scan OCT images. Considering the retina is thin (200 f·m) compared to the eyeball diameter (h=6 mm for rats), the coordinates of E' and S' can be expressed as:

$$x_1 = r_1 \times \cos(\phi_1)$$

$$x_2 = r_2 \times \cos(\phi_2)$$

$$y_1 = r_1 \times \sin(\phi_1)$$

$$y_1 = r_2 \times \cos(\phi_2)$$

In some examples, circular B-scan images from <=0 to 360 degree horizontally may be used. The vertical axis z is the depth, where the low boundary of B-scan image was set as z=0. Vessels can be segmented from the outer and inner scanning circular B-scan images. The z coordinates as well as $r_{p1}$ and $r_{p2}$ could be measured. $r_1$ and $r_2$ can be calculated by:

$$r_1 = h \cdot \tan(\phi_1), r_2 = h \cdot \tan(\phi_2).$$

The scanning angles $\phi_1$ and $\phi_2$ may be set as 4 degree and 6 degree by the galvo mirrors, respectively. Given all the coordinates, the Doppler angle θ could be calculated according to:

$$\cos(\theta) = \frac{\overline{ES} \cdot \overline{NS'}}{|\overline{ES}| \cdot |\overline{NS'}|}.$$

In order to calculate flow, the cross sectional diameter and area may also be used. Vessel height H may be obtained axially from amplitude B-scan image. The diameter of the blood vessel Dia may then be equal to:

$$Dia = H \times \sin(\theta)$$

and Dia can be solved.

Analytes as described herein may refer to any chemical or biochemical moiety suitable for imaging. In some examples, this may include but is not limited to oxygen, hemoglobin, oxygenated hemoglobin, deoxygenated hemoglobin, glucose, sugar, blood area nitrogen, lactate, hematocrit, biomarker, molecular marker, or nucleic acid that maybe suitable to image to determine target function. The analytes may also be molecules, including but not limited to: polypeptides, proteins, antibodies, enzymes, nucleic acids, saccharides, small molecules, drugs, and the like.

In some examples, the devices, methods, and systems of the disclosure provide for "label-free" quantitatively 3D-imaging in the target, a flow rate of a fluid and a concentration of one or more analytes. In this example, analytes and flow are calculated without the use of exogenous reagents contacted with either the analytes or the targets. For example, a variety of imaging methods have been described describing quantifying analytes or flow with the use of contrast reagents or additional chemical markers or signals that may bind to one more analytes. The devices, methods, and systems of the disclosure provide an imaging system where one or more analytes imaged are label-free.

In some examples, however, one or more contrast reagents may be used in conjunction with the devices, methods, and systems of the disclosure. In this example, quantitatively 3D-imaging in the target, a flow rate of a fluid and a concentration of one analyte may be obtained without a label, while one more additional analyte concentrations may be determined by contacting one or more analytes with a exogenous reagent such as contrast reagent.

A target may include any vessel or structure that can contain a fluid to be imaged including but not limited to tissue, healthy tissue, diseased tissue, retina, tumor, cancer, growth, fibroid, lesion, skin, mucosal lining, organ, graft, blood supply and one or more blood vessels.

In some examples, a fluid may include but is not limited to whole blood, blood plasma, blood serum, urine, semen, tears, sweat, saliva, lymph fluid, pleural effusion, peritoneal fluid, meningal fluid, amniotic fluid, glandular fluid, spinal fluid, conjunctival fluid, vitreous, aqueous, vaginal fluid, bile, mucus, sputum and cerebrospinal fluid.

iv. Determining a Rate of Change of Analyte and Target Function

Generally, the devices, methods, and systems of the disclosure provide processes to determine the rate of change of concentration of analyte. Quantitatively imaging a flow rate of a fluid in the target and a concentration of one or more analytes in the fluid in the target may be performed at one time point or over a succession of time points. In some examples, a target may be monitored over a period of time of at least 1 msec, 1 sec, 1 min, 1 hr, 1 day, 1 week, 1 month, 1 year, and 10 years. In some examples, a target may be monitored over period of time of at most 1 msec, 1 sec, 1 min, 1 hr, 1 day, 1 week, 1 month, 1 year, and 10 years. In some examples, a target may be monitored for 20-60 min. In some examples, a target may be monitored over 1 to 5 years. In some examples, a target may be monitored for 1 to 60 secs. In some examples, a target may be monitored for 1 ms to 500 msec.

In some examples, target function may include but is not limited to metabolic activity, metabolic rate, oxygen consumption, tissue consumption of a biomarker or analyte, pathophysiological alterations, pathological alterations, histological change such as tissue remodeling, abnormal growth of one or more blood vessels, or abnormal tissue growth, necrosis, apoptosis, necrosis, angiogenesis, cell proliferation, neurmodulation, neural activity, wound healing, infection, burns, scarring, radiological damage, hypoxia, oxidative stress and the like.

In some examples, a change in target function may be determined by comparing information from 3D-imaging in the target, a flow rate of a fluid and a concentration of one or more analytes to a reference. In some examples a reference many include but is not limited to a healthy image, or an average of information from healthy subjects. In some examples, a reference may include information from a 3D-image generated at a different time. In some examples one or more references may be compared to other references to determine a change in rate of one or more analyte concentrations.

III. Functional OCT and Metabolic Activity

In some examples, fOCT may be used specifically for metabolic imaging of one or more tissues. In certain examples, metabolic imaging may provide diagnostic information regarding the health status of a tissue in a subject.

Using the example system 200 of FIG. 2(*a*), visible-light optical coherence tomography (vis-OCT) can quantify rMRO2 in vivo through the concurrent measurement of the blood flow and sO2 from retinal circulation. Using an OCT spectral analysis, sO2 can be measured in vivo. 3D imaging capability allows vis-OCT to recover optical spectra specifically from blood vessels and eliminate a confounding signal from other retinal layers. Metabolic rate rMRO2 may be obtained by combining the sO2 measurement with the OCT flow measurement.

In operation, for example, the three-dimensional (3D) structure of a retina may be scanned by passing a focused broadband laser across the retina to provide transverse (x,y) discrimination. A reflectance at depth (z), A-line, is reconstructed based on interference between reflected light and a reference light.

Each 3D measurement (e.g., 2.8 mm by 2.8 mm by 1 mm in x, y, z) may take only several seconds (e.g., 2.5 s) with a high frame rate (e.g., 98 fps), allowing monitoring of the rMRO2 with high temporal resolution. To quantify the rMRO2 (e.g., gas volume of oxygen consumed per unit time, mL/min), two parameters are measured from the retinal circulation: total retinal blood flow F [J·L/min] and relative sO2 [percent]. The rMRO2 can be calculated according to the following equation:

$$rMRO_2 = 1.34 \times C_{H_b} \times F \times (s_aO_2 - s_vO_2),$$

where $C_{Hb}$ is a hemoglobin concentration [g/J·L], and 1.34 is an oxygen-binding capacity of hemoglobin [mL/g]. The subscript of w and v denotes arterial and venous sO2. Blood flow is a product of cross-sectional vessel area (s) and velocity (v), where s is calculated from a tomographic image and v is measured based on the phase variation from the moving blood cells. The contrast for sO2 is from the distinct absorption spectra for oxy- and deoxyhemoglobin, for example. By fitting the blood spectra extracted from blood vessels, a percentage of oxyhemoglobin in total hemoglobin (sO2 by definition) can be calculated, for example.

Figure 3:
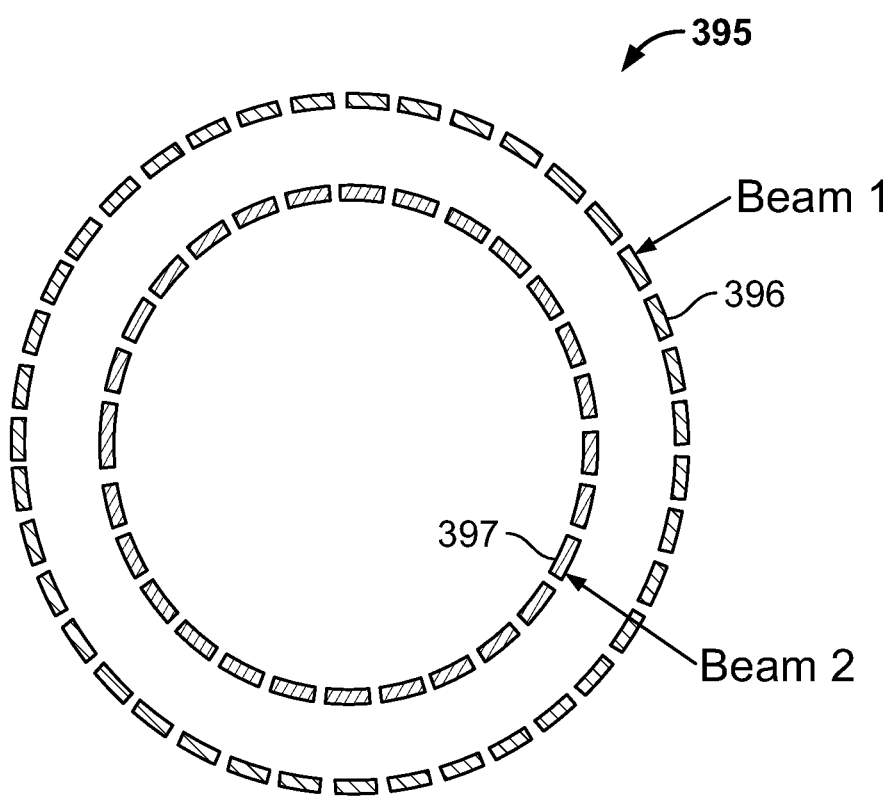
FIG. 3 is an example schematic of dual beam scanning. The target is illuminated with one or beams concurrently or sequentially.

In operation, certain examples provide a dual-beam scanning method to achieve metabolic imaging. A first beam is generated using visible-light, and a second beam is generated using NIR light. The visible-light OCT beam measures $sO_2$, and the NIR-light OCT beam measures blood flow. The dual-beam OCT system and associated scanning patterns can be designed in multiple ways. FIG. 2(*a*) provides one example system 200 able to generate and measure a variety of beam patterns and resulting illumination. For example, FIG. 3 shows a circular dual-beam scanning method 395. As shown in the example of FIG. 3, a first beam 396 is a visible light beam to measure $sO_2$ in a target pupil, and a second beam 397 is a near-infrared beam to measure blood flow in the pupil. Using the dual-beam circular scanning method, beams 396, 397 move in a circular motion around an optic nerve head (ONH). Because retinal blood vessels run radially from the ONH, each circle of the beams crossed all of the arteries and veins attached to the retina and allow capture of total retinal blood flow. The displacement of vessels between the two circular scans also provides vessel directionality for absolute flow. High-speed scanning also facilitates capture of a pulsatile profile of the blood flow, for example.

Figure 4:
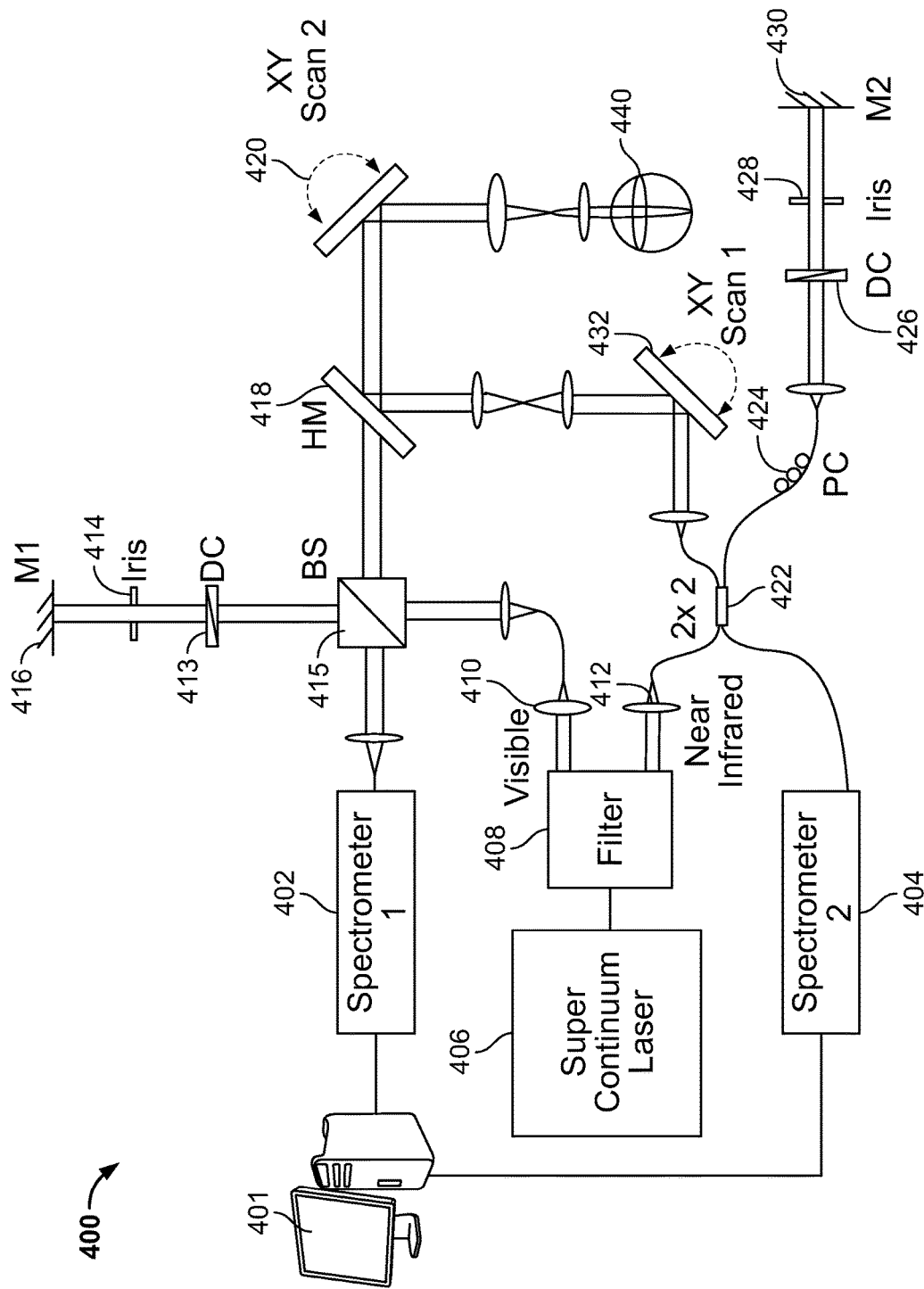
FIG. 4 is a schematic of an example fOCT device.

FIG. 4 illustrates an alternative dual-beam circular scanning system 400 designed with one OCT as an open-space based system and another OCT as a fiber-optics based system. The example system 400 includes a computer or other processor 401 controlling two spectrometers 402, 404 to analyze illumination generated by a super continuum laser 406. The laser 406 uses a filter 408, which separates the laser light into visible 410 and NIR 412 wavelengths.

Visible light beam 410 is directed through a beamsplitter 415 and regulated with a DC 413, an iris 414, and a mirror 416 to be illustrated from a hot mirror (HM) 418 to an XY scan mirror 420 and onto a target eye 440. The NIR beam 412 passes through fiber-optics 422 and is regulated using a combination of a polarization control (PC) 424, a DC 426, an iris 428, and a mirror 430. The NIR beam 412 is illustrated by an XY scan mirror 432 to the HM 418 and then onto the target eye 440 via the XY scan mirror 420.

Figure 5:
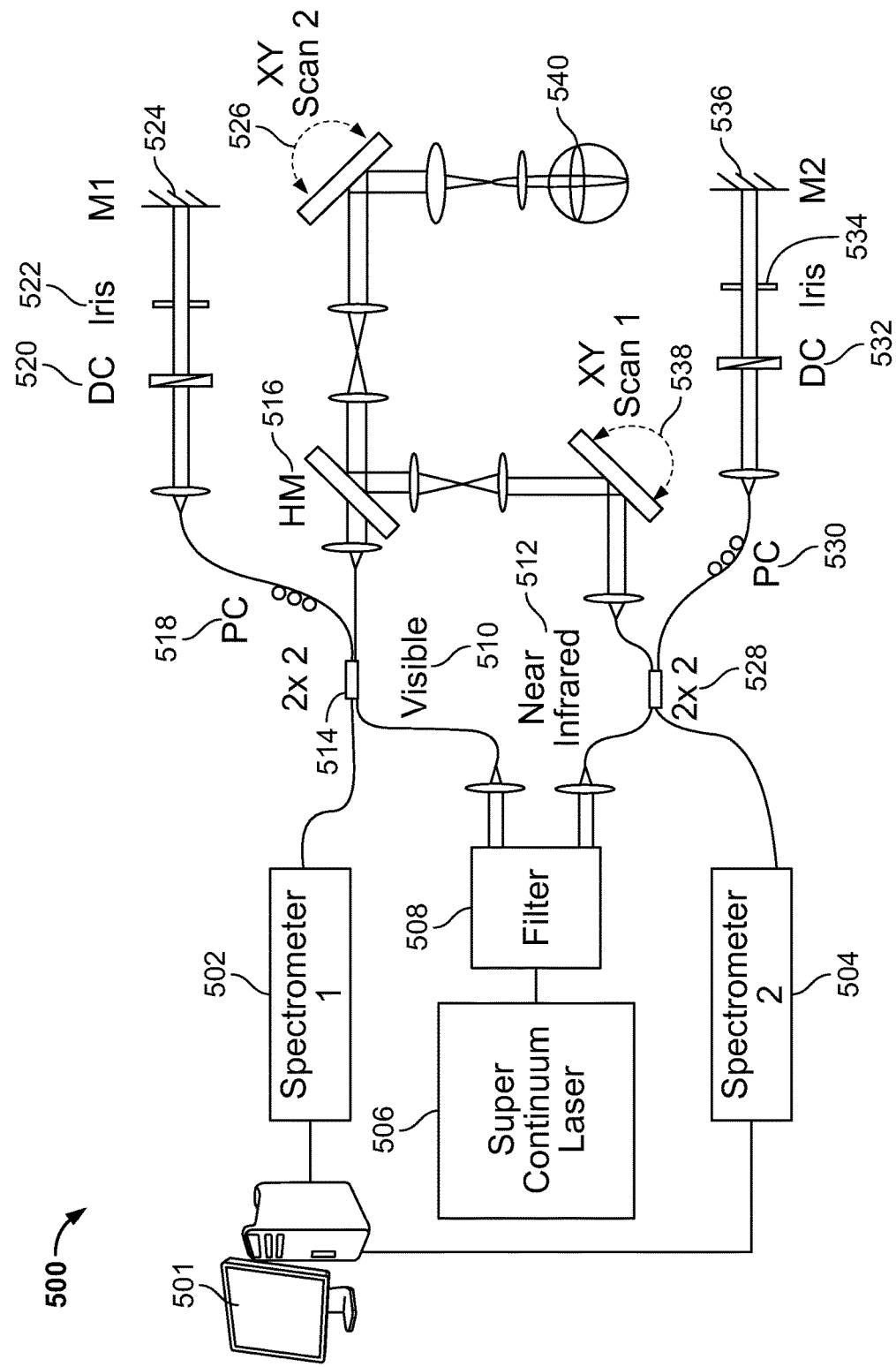
FIG. 5 is a schematic of an example fOCT device.

FIG. 5 illustrates an alternative dual-beam circular scanning system 500 designed with two OCTs optical fiber based systems. The example system 500 includes a computer or other processor 501 controlling two spectrometers 502, 504 to analyze illumination generated by a super continuum laser 506. The laser 506 uses a filter 508, which separates the laser light into visible 510 and NIR 512 wavelengths.

Visible light beam 510 is directed through fiber optics 514 to an HM 516. The visible light 510 is regulated with a PC 518, a DC 520, an iris 522, and a mirror 524. The visible light 510 is steered from the HM 516 to an XY scan mirror 526 and onto a target 540. The NIR beam 512 passes through fiber-optics 528 and is regulated using a combination of a polarization control (PC) 530, a DC 532, an iris 534, and a mirror 536. The NIR beam 512 is reflected by an XY scan mirror 538 to the HM 516 and then onto the target 540 via the XY scan mirror 526.

While example systems 500 and 600 achieve the same purpose of metabolic OCT, the systems 500, 600 achieve that result with a different vis-OCT design. The dual fiber-optic OCT based system 600 can be more compact than the system 500, but data processing is equivalent between the outputs of the two systems 500, 600. Any of systems 200, 500, 600 can be used to implement various beam patterns, although system 200 is better suited for circular beam pattern 300.

Figure 6:
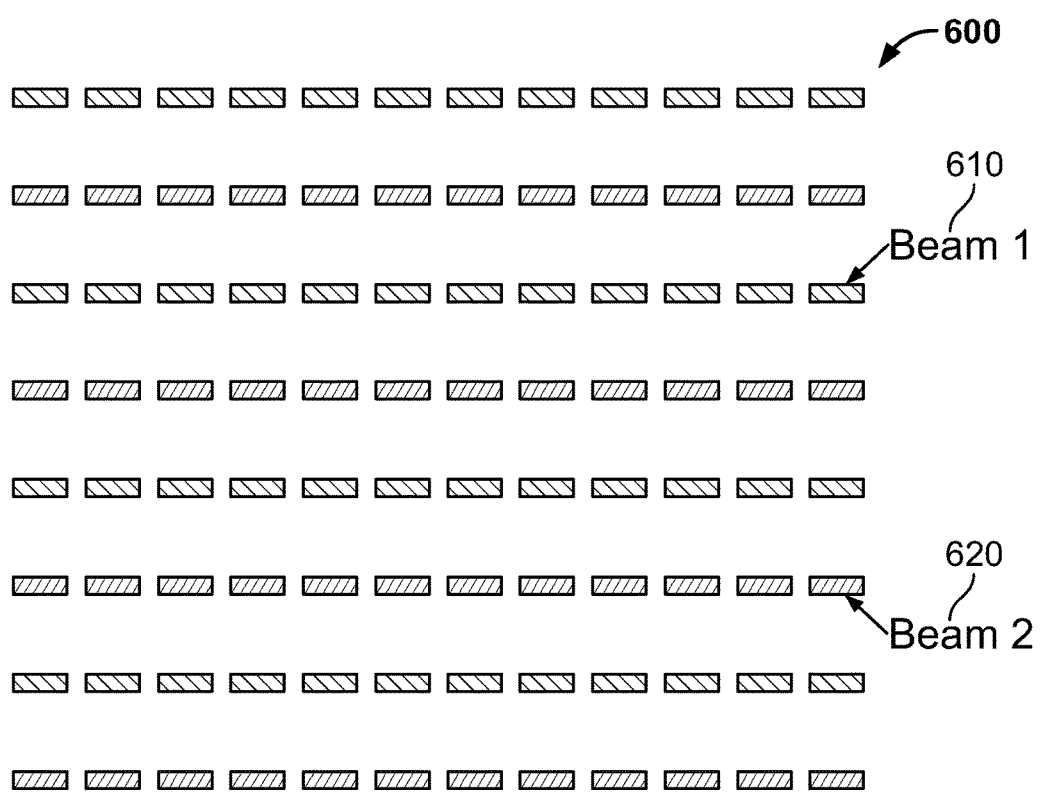
FIG. 6 is an example schematic of multi beam scanning. The target is illuminated with one or more beams concurrently or sequentially.

FIG. 6 illustrates an alternative dual-beam linear scanning method 600. As demonstrated in the example of FIG. 6, a first beam 610 is a visible light beam to measure sO2 in a target pupil, and a second beam 620 is a near-infrared beam to measure blood flow in the pupil. Each beam 610, 620 moves along a separate path to scan a portion of retinal blood vessels. Any of the example systems 200, 400, 500 can be used to execute the distinctive paths dual beam method 600.

Figure 7:
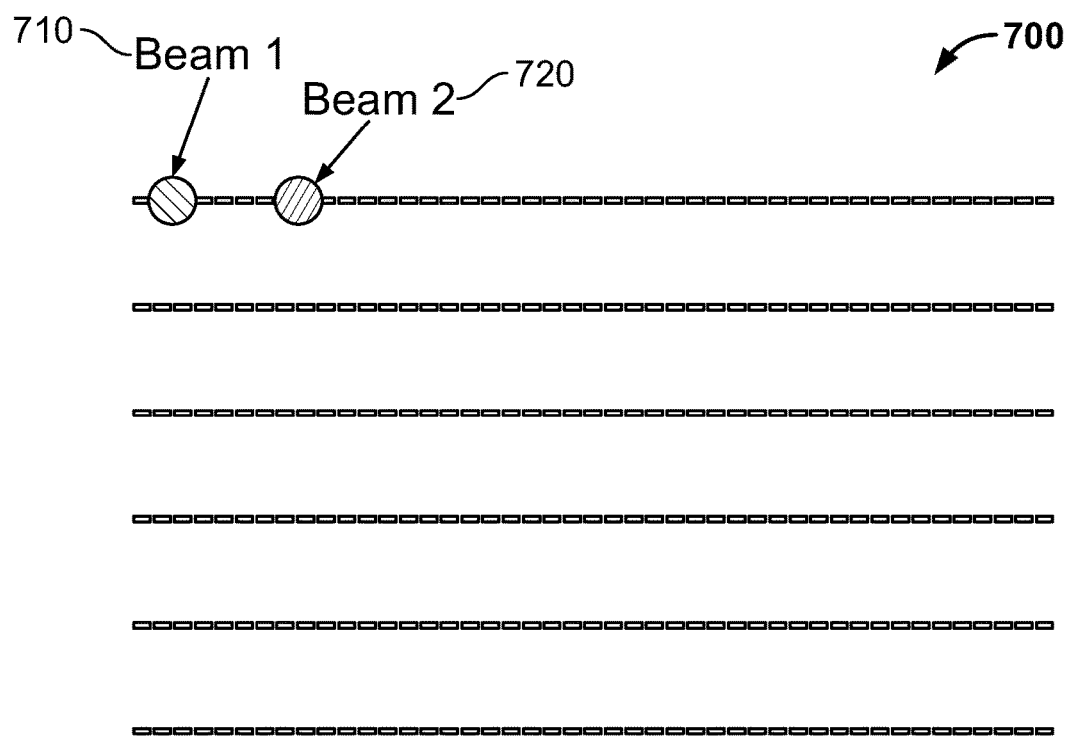
FIG. 7 is an example schematic of multi beam scanning with two or more beams. The target is illuminated with one or more beams concurrently or sequentially.

FIG. 7 illustrates an alternative dual-beam linear scanning method 700. As demonstrated in the example of FIG. 7, a first beam 710 is a visible light beam to measure sO2 in a target pupil, and a second beam 720 is a near-infrared beam to measure blood flow in the pupil. In the example method 700, beams 710 and 720 moves along a same path, separated by a determined distance, to scan a portion of retinal blood vessels. Any of the example systems 200, 400, 500 can be used to execute the spatial separation dual beam method 700.

Figure 8:
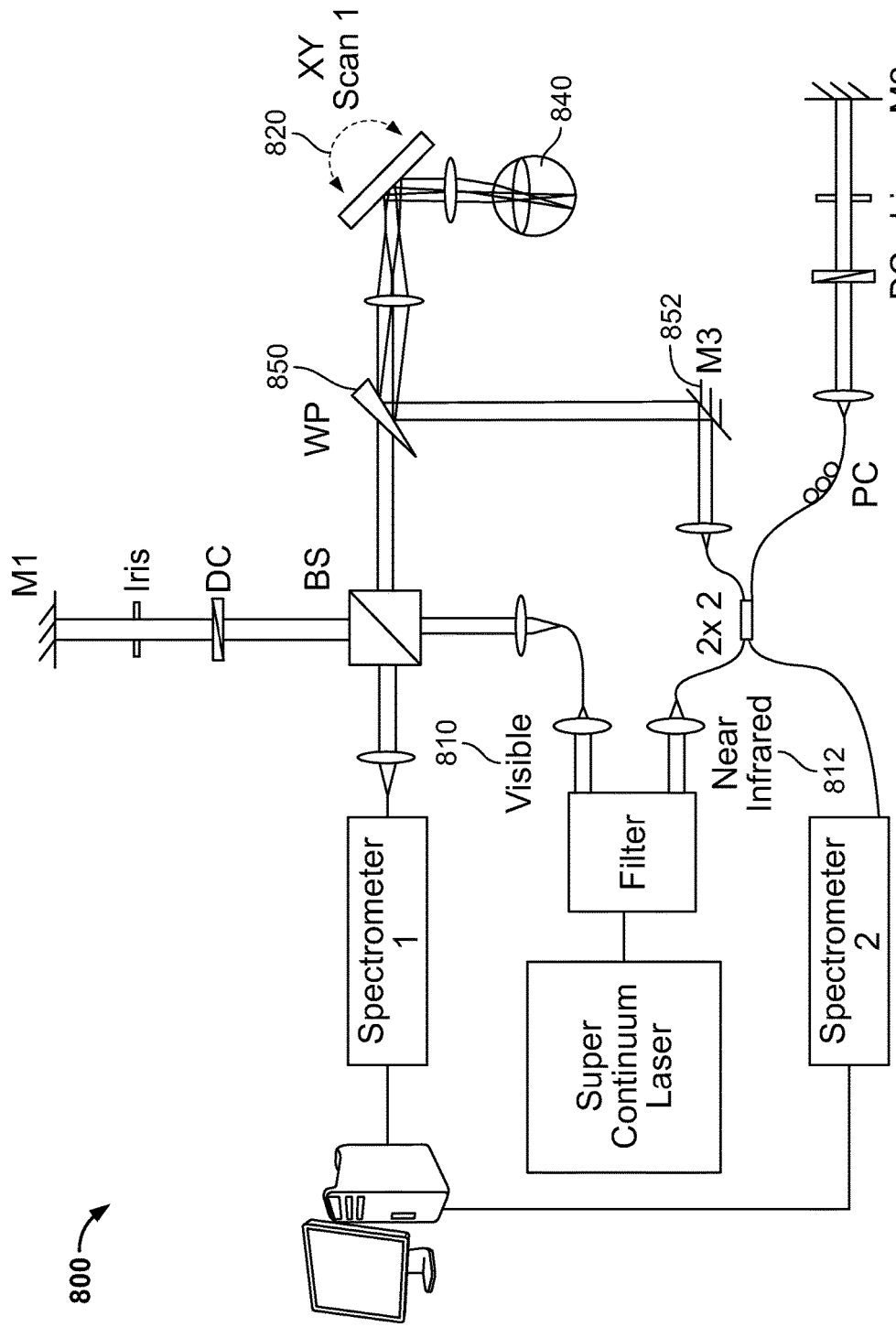
FIG. 8 is a schematic of an example fOCT device.

FIG. 8 illustrates an alternative dual-beam circular scanning system 800. The dual-beam circular scanning system 800 includes one OCT as an open-space based system and another OCT as a fiber-optics based system and represents a variation in the design of system 400. Specifically, rather than using an HM 412 and a second XY scanning unit 432, the example system 800 uses only one XY scanning unit 820 and instead uses a wedge prism 850 and a third mirror 852 to steer visible 810 and NIR beams 812 to a target 840 via the XY scan unit 820.

Figure 9:
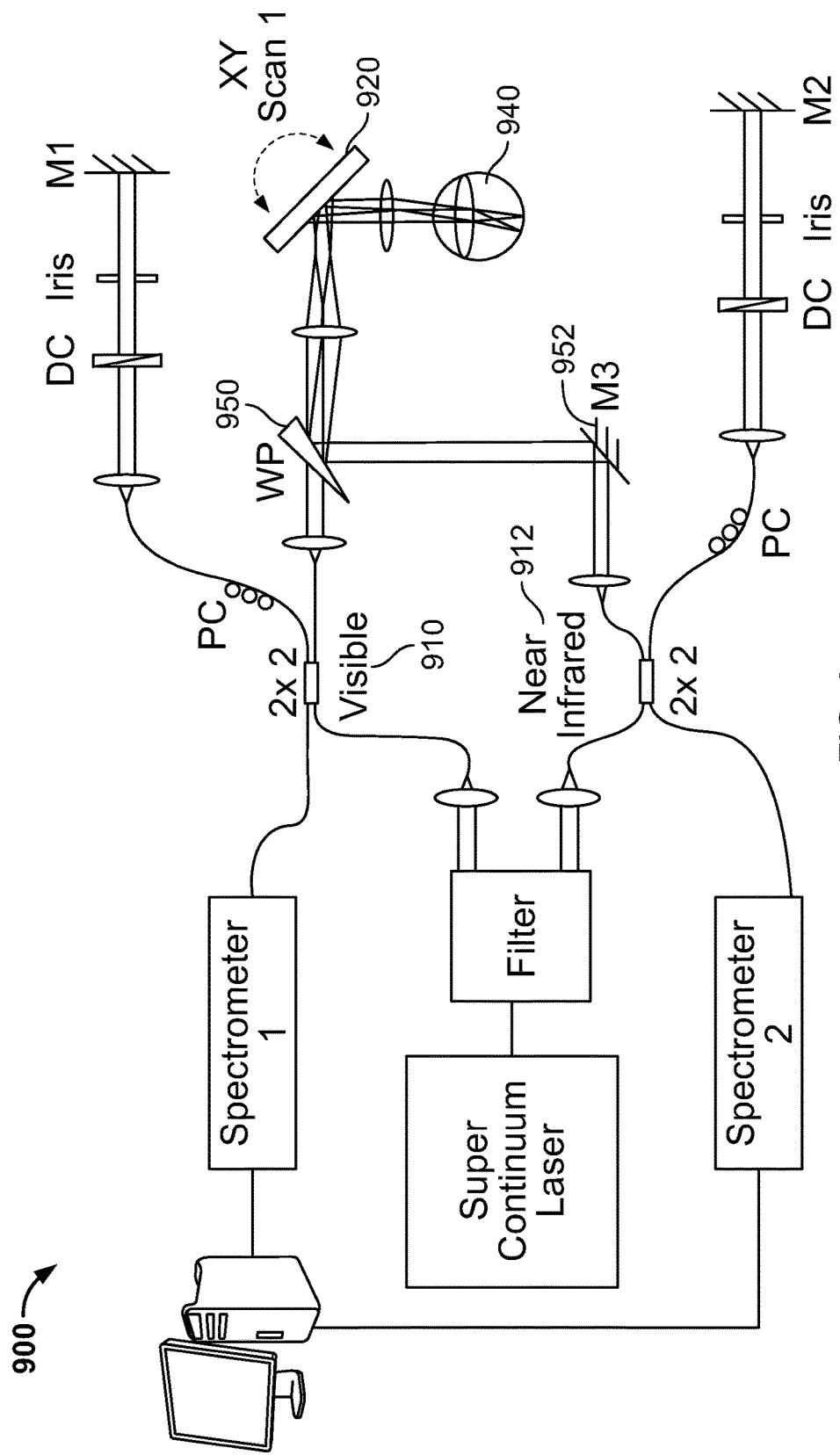
FIG. 9 is a schematic of an example fOCT device.

FIG. 9 illustrates an example dual-beam circular scanning system 900. The dual-beam circular scanning system 900 includes two optical fiber based OCTs and represents a variation in the design of system 500. Specifically, rather than using an HM 516 and a second XY scanning unit 538, the example system 800 uses only one XY scanning unit 920 and instead uses a wedge prism 950 and a third mirror 952 to steer visible 910 and NIR beams 912 to a target 940 via the XY scan unit 920.

FIGS. 10(a)-(d) show example $sO_2$ information acquired noninvasively from a subject's eye using visible-light OCT. FIG. 10(a) displays a fundus image in grayscale in inversed contrast. The bright blood vessel structure corresponds to the strong optical attenuation in blood.

For comparison, the 3D OCT volume was sectioned and used to project a mean intensity. FIG. 10(b) illustrates a resulting enhanced contrast from the microvasculature of the eye. Also, mean sO2 values in major vessels can be quantified, resulting in a sO2 pseudo-color map overlay shown in FIG. 10(b).

In the example of FIG. 10(a), a circular scanning pattern was employed around the optic disk (e.g., with 4096 A-lines) to sample all major blood vessels in the eye. FIG. 10(c) shows the circular scan of FIG. 10(a) expanded into a B-scan image, where a vessel index corresponds to a number on the circle scan in FIG. 10(a). The values of sO2 in individual vessels are shown in FIG. 10(d). In a color image, red and blue color could label arteries and veins, respectively.

Figure 11A:
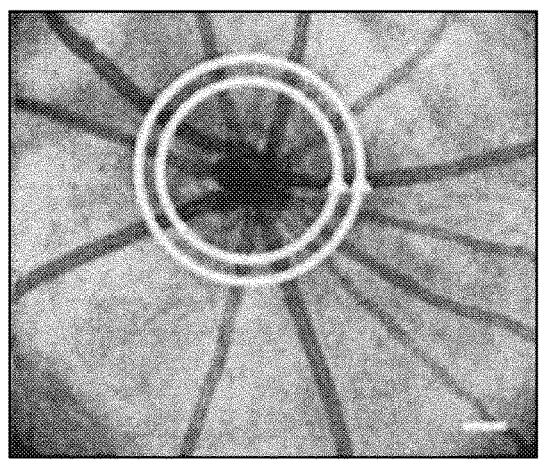
FIG. 11a is an example vis-OCT fundus image. The white circular line represents the B-scan trajectory.
Figure 11B:
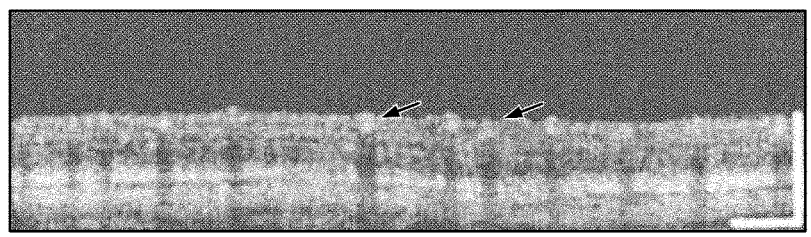
FIG. 11b is an example B-scan.
Figure 11C:
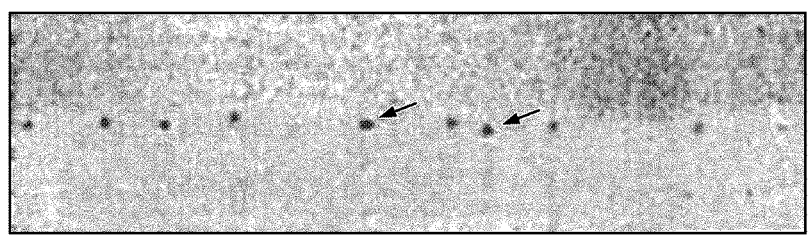
FIG. 11c is an example phase shift B-scan image.

FIGS. 11(a)-(g) show example blood velocity and flow measurement information obtained through dual-scan NIR light OCT. FIG. 11(a) shows an example retinal fundus image of spectral domain optical coherence tomography (SD-OCT). White rings indicate locations at which dual beam laser scans were performed, each pair including one big circle and one small circle scan. FIG. 11(b) shows a sample amplitude SDOCT image. FIG. 11(c) depicts a corresponding phase SD-OCT image of FIG. 11(b).

Figure 11D:
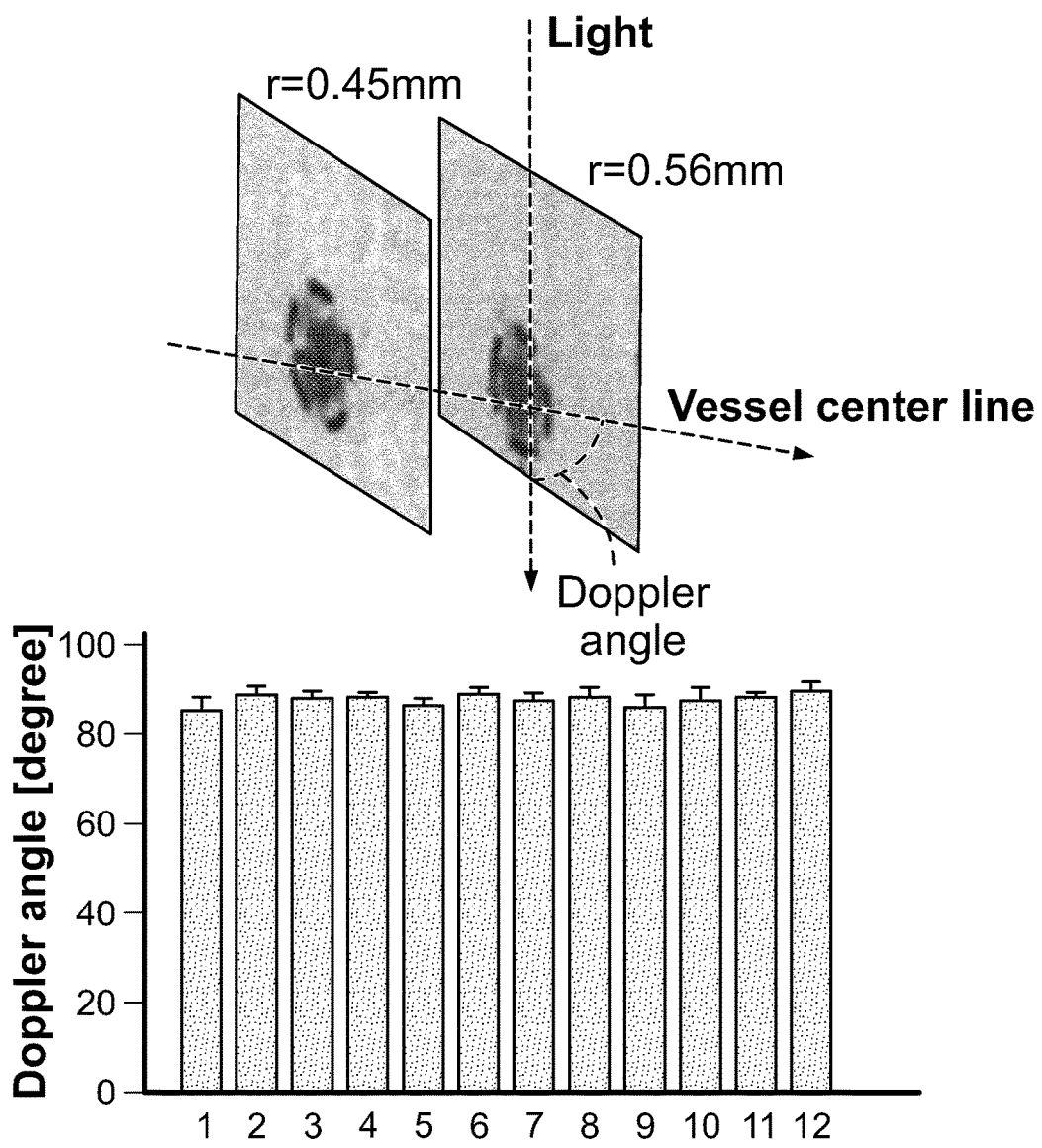
FIG. 11d is an example schematic and graph of measured Doppler angles.

FIG. 11(d) represents Doppler angles for blood vessels. The upper portion of FIG. 11(d) shows a Doppler angle of one sample vessel (indicated within a black dashed square in FIG. 11(c)). The lower portion of FIG. 11(d) provides statistic results of Doppler angles across 8 pairs of data.

Figure 11E:
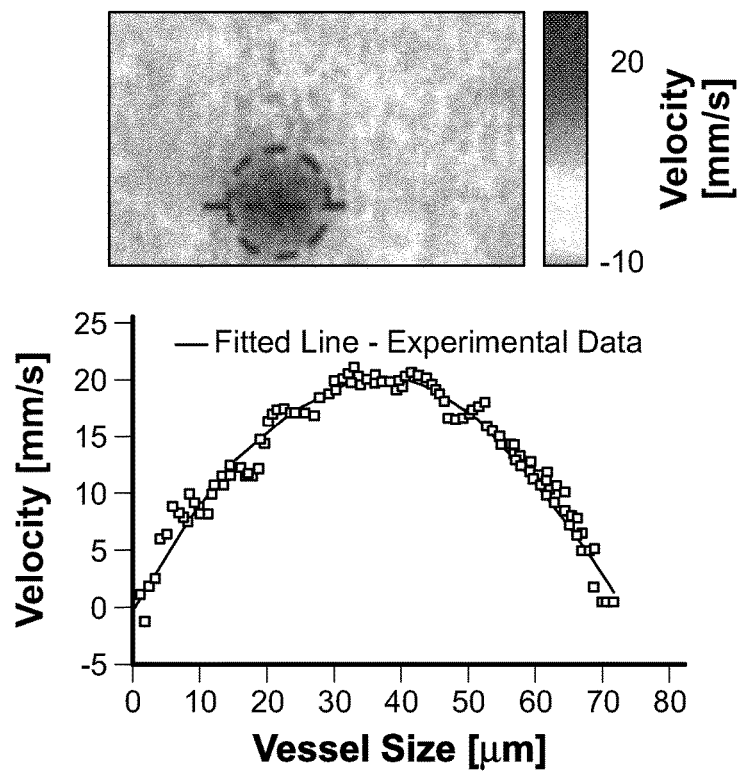
FIG. 11e is an example graph of fitted blood flow velocity data.

FIG. 11(e) provides an analysis of blood velocity within the sample vessel (e.g., within the black dashed square in FIG. 11(c). The upper portion of FIG. 11(e) shows a velocity distribution of the whole sample vessel. The lower portion of FIG. 11(e) shows a transversal velocity distribution in a direction indicated by the dashed line in FIG. 11(e). In the example of FIG. 11(e), raw data is fitted by quadratic function.

Figure 11F:
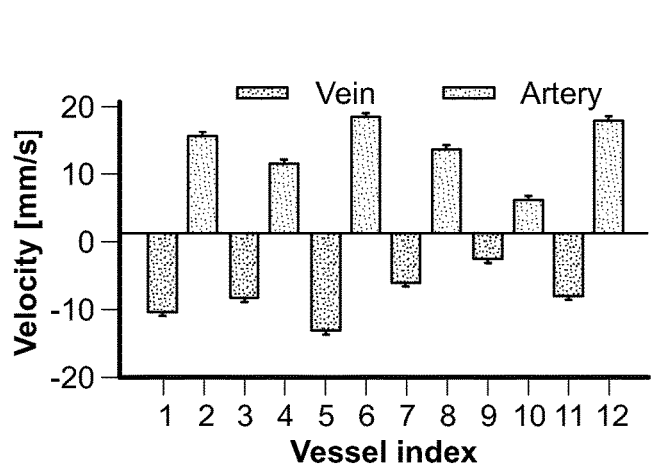
FIG. 11f is an example graph of blood flow velocity data for arteries and veins.
Figure 11G:
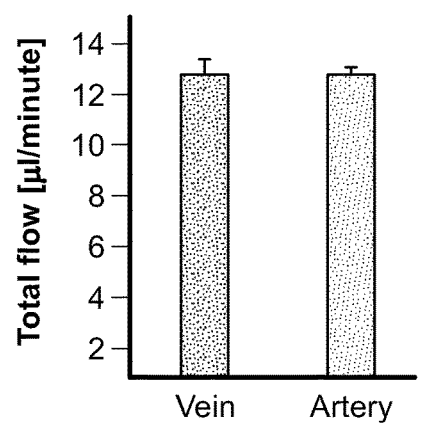
FIG. 11g is an example graph of total blood flow velocity data for arteries and veins.

FIG. 11(f) illustrates example statistical results of blood velocity for 12 retinal vessels across 8 pairs of data. FIG. 11(g) shows example statistical results for blood flow in retinal veins and arteries across 8 pairs of data. In the example of FIG. 11(g) each bar is 200 um.

Thus, certain examples provide in vivo retinal oximetry by vis-OCT based on a comprehensive analytical model describing both scattering and absorption from whole blood, as well as blood vessel scattering. Oxygen consumption is based on blood flow rate and a change in oxygen saturation rate (sO2) based on simultaneous scanning with both visible and NIR light. Retinal metabolic rate can then be derived. Certain examples provide parameter measurement, rather than estimation. Certain examples provide total blood flow and/or regional blood flow in blood vessels associated with a target retina.

Microvasculature visualization 1322 may also be determined based on the volumetric data set and the surface topography previously computed. A slab is sliced from the 3D volumetric dataset (e.g., 150 to 200!Jm deep from retinal surface), and a 2D mean intensity projection map is created from the slab. Next, morphological closing is performed with a radial disk pattern (e.g., 3 pixel) to obtain an inhomogeneous intensity background. Then, the 2D mean intensity projection map is normalized by this background to enhance the contrast from the microvasculature.

IV. Medical Applications

In various examples, one or more fOCT images may provide data from which a diagnosis and/or evaluation may be made. In some examples, such determinations may relate to biologic tissue structure, vasculature, and/or microcirculation. For example, in some examples, 3-D in vivo imaging of a biologic tissue and quantifying flow of blood through individual vessels therein may be useful in understanding mechanisms behind a number of disease developments and treatments including, for example, ischemia, degeneration, trauma, seizures, and various other neurological diseases. In still other examples, an OCT image and techniques herein disclosed may be used to identify cancer, tumors, dementia, and ophthalmologic diseases/conditions (including, e.g., glaucoma, diabetic retinopathy, age-related macular degeneration). Still further, in various examples, OCT techniques as herein disclosed may be used for endoscopic imaging or other internal medicine applications. In some examples, fOCT may be used to stratify treatment options, such as personalizing or tailoring a patient treatment specific treatment protocol. In some examples, fOCT may be used as a companion diagnostic for one or more drugs. In some examples, fOCT may also be used to assess efficacy of a drug treatment during monitoring of a disease. In some examples, fOCT may also be used to screen drug efficacy during drug development. The foregoing illustrative examples of diagnosis and/or evaluation are exemplary and thus examples of the present invention are not limited to the examples discussed.

A. fOCT and Medical Decisions

In some examples, fOCT may be used to provide a medical decision. In some examples, a medical decision may include but is not limited to a treatment step, diagnostics, monitoring, follow-up, evaluation, confirmation of a diagnosis, prognosis, selecting a drug for a patient, changing a drug treatment to another drug, stopping a drug treatment, changing a treatment or drug dosage, increasing or decreasing frequency of treatment or drug administration, or recommending further evaluation. In some examples, a medical decision may be the guidance of a surgical tool or a surgical operation. In some examples, a medical decision may be the placement of one or more medical instruments or tools, such as the placement of a stent, or the placement of a suture. In some examples, a medical decision may be the determining of surgical margins in the excision of a tumor.

B. Molecular Markers, Contrast Reagents and Bodily Fluids

In some examples fOCT may be used to detect or quantify a variety of molecular markers, which may be associated with a disease. The term molecular marker as defined herein includes, but is not limited to, a molecule or biomolecule, a whole cell or a commercially important substrate that may need to be tracked for its distribution or identification. Molecules and biomolecules include nucleic acids, peptides, proteins, oligosaccharides, lipids, antigens, and small molecules. Commercially important substrates include, but are not limited to, organic and inorganic polymers, small molecules or chemical moieties or products made therefrom. In some examples, the molecular marker may include but is not limited to oxygen, hemoglobin, oxygenated hemoglobin, deoxygenated hemoglobin, glucose, sugar, blood area nitrogen, lactate, hematocrit, biomarker and nucleic acid.

In some examples, one or more contrast reagents may be used in combination with the devices, methods and systems of the present disclosure. Generally, the disclosure provides for the quantification of a flow rate of a fluid and concentration of one or more analytes in target, where at least one of the analytes is not contacted with an exogenous reagent. In other examples, a contrast reagent or label may be included to quantify one or more analytes in addition to, or in combination with the quantification of a flow rate of a fluid and concentration of one or more analytes that have not been contacted with a contrast reagent or label.

It is known the art, that numerous types of contrast reagents and labels may be used for the detection and quantification of different analytes. In some examples, contrast reagents, exogenous reagents may be any suitable chemical, moiety or molecule that may provide a spectral signal to allow the analyte or flow rate to be scanned and quantified by OCT. In some examples, a contrast reagent or label may include a chemically linked moiety, ligand, antibody, small molecule, organic molecule, radioactive probe, nucleic acid and the like.

In some examples, the concentration of one or more molecular markers may be determined in one or more bodily fluids. Generally, any bodily fluid may be suitable for imaging with fOCT. In some examples, a bodily fluid may include but is not limited to whole blood, blood plasma, blood serum, urine, semen, tears, sweat, saliva, lymph fluid, pleural effusion, peritoneal fluid, meningal fluid, amniotic fluid, glandular fluid, spinal fluid, conjunctival fluid, vitreous, aqueous, vaginal fluid, bile, mucus, sputum and cerebrospinal fluid.

C. Stratification of Treatment Decisions

The methods of the provided disclosure can include using the status of one or more molecular markers determined in a target to stratify (rank) treatment options for a subject. In some examples, treatment may include any medical decisions as described herein. In some examples, one or more drugs may be stratified based on information determined by fOCT. The stratifying of drug treatments can be based on scientific information regarding the molecular markers. For example, the scientific information can be data from one or more studies published in one or more scientific journals (e.g., New England Journal of Medicine (NEJM), Lancet, etc.). The scientific information can be data provided in a commercial database (e.g., data stored in a database provided by Ingenuity® Systems). One or more pieces of scientific information can be used to stratify the treatments. In some examples, the data or scientific information may not be published. In some examples the data or scientific information is maintained in a private database and used for comparison across select patients or sub groups of patients.

i. Classes of Drugs

Drug treatment options can be stratified into classes based on the status of one or more molecular markers in a target. For example, a first class of drug treatment options can be those for which scientific information predicts a drug will be efficacious for a subject whose target has one or more molecular markers of a particular status. Drugs in this first class can be a recommended drug treatment option for a subject.

A second class of drug treatment options can be those for which some scientific information predicts a drug will be efficacious for a subject with one or more molecular markers of a particular status, and some scientific information does not support use of the drug for the subject, based on one or more molecular markers of a particular status in a sample from a subject. For example, a sample may contain a marker whose status indicates the drug will be efficacious in the subject and another marker (e.g., a particular metabolic profile that indicates a specific disease state or stage) or may indicate the drug would also have a toxic affect on the subject.

This second class can also include drugs for which there is indirect scientific support for drug efficacy in a subject (e.g., the drug targets a protein that is in the same molecular pathway as a molecular marker in a target). For example, a drug in this class could target a kinase that functions downstream of an overexpressed variant of VEGF, which correlates with higher metabolic rate in a target as determined by fOCT. A drug in this second class can be a recommended drug treatment option for a subject.

A third class of drugs can be those for which scientific information indicates the drug will not be efficacious in the subject based on the status of one or more molecular markers in a sample from the subject. For example, a drug that targets a cell surface receptor may not display efficacy if information provided by fOCT imaging does not correlate well if efficacy. It can be recommended that a subject not be treated with a drug in this third class.

The drug treatment options can be stratified using an algorithm-based approach. The status of one or more molecular markers in a patient sample is determined. The scientific literature or a database of curated fOCT scans of one or more similar targets of one or more subjects is analyzed for information related to the status of the molecular marker and the efficacy of one or more different drugs. If the status of a molecular marker correlates with efficacy of a drug, then a recommendation can be made to treat the subject with that drug. If the status of a molecular marker does not correlate with efficacy of a drug, then a recommendation can be made not to treat a subject with the drug. A computer and computer readable medium can be used to stratify the drug treatment options.

A list of stratified drug treatment options can be presented in the form of a report. The stratification of drug treatment options can be indicated by color coding. For example, drugs in the first class can be color coded in green, drugs in the second class can be color coded in yellow, and drugs in the third class can be color coded in red.

The recommendation of a drug treatment option for a subject can be based on the stage of the diseases, (e.g. cancer of the subject, e.g., a late stage cancer, AMD, late stage AMD). Drug treatment options can also be stratified based on other factors, e.g., the type of disease, age of the subject, status of drug metabolism genes (genes involved in absorption, distribution, metabolism, and excretion), efficacy of other drugs the patient has received, clinical information regarding the subject, and family medical history.

In some examples, particular classes of drugs may be useful for treatment. In some examples, when fOCT is used to determine metabolic rate of tissues as result of abnormal blood vessel proliferation or decrease, drugs known to affect blood vasculature may be suitable. In some examples this may include but is not limited to an angiogenesis inhibitor, e.g., a VEGF (Vascular Endothelial Growth Factor) pathway inhibitor, e.g., a VEGF pathway inhibitor described herein, e.g., a VEGF inhibitor, e.g., a small molecule inhibitor, protein, e.g., a fusion protein (e.g., aflibercept) or an antibody against VEGF, e.g., bevacizumab; or a VEGF receptor inhibitor (e.g., a VEGF receptor 1 inhibitor or a VEGF receptor 2 inhibitor), e.g., a small molecule inhibitor, e.g., sorafenib, sunitinib, pazopanib or brivanib, or an antibody against VEGF receptor.

B. Diseases fOCT may be used in medical decisions related to a variety of diseases. These may include neurological diseases, which may include but is not limited to dementia, concussion, Alzheimer's disease, Parkinson's disease, peripheral neuropathy, epilepsy and multiple sclerosis. In some examples, these may include vascular diseases, including but not limited to diabetes, peripheral vascular diseases, stroke, cardiovascular diseases, myocardial infarction, and aneurysm.

In some examples, fOCT may be used to provide medical decision for ocular diseases which may include but is not limited to autosomal retinitis pigmentosa, autosomal dominant retinitis punctual albescens, butterfly-shaped pigment dystrophy of the fovea, adult vitelliform macular dystrophy, Norrie's disease, blue cone monochromasy, choroideremia, gyrate atrophy, age-related macular degeneration, retinoblastoma, anterior and posterior uveitis, retinovascular diseases, cataracts, corneal dystrophies, retinal detachment, degeneration and atrophy of the iris, and diabetic retinopathy, herpes simplex virus infection, cytomegalovirus, allergic conjunctivitis, dry eye, lysosomal storage diseases, glycogen storage diseases, disorders of collagen, disorders of glycosaminoglycans and proteoglycans, sphinogolipodoses, mucolipidoses, disorders of amino acid metabolism, dysthyroid eye diseases, anterior and posterior corneal dystrophies, retinal photoreceptor disorders, corneal ulceration, and ocular wounds.

In some examples fOCT may be used for medical decisions related to cancer, for example, acute myeloid leukemia; bladder cancer, including upper tract tumors and urothelial carcinoma of the prostate; bone cancer, including chondrosarcoma, Ewing's sarcoma, and osteosarcoma; breast cancer, including noninvasive, invasive, phyllodes tumor, Paget's disease, and breast cancer during pregnancy; central nervous system cancers, adult low-grade infiltrative supratentorial astrocytoma/oligodendroglioma, adult intracranial ependymoma, anaplastic astrocytoma/anaplastic oligodendroglioma/glioblastoma multiforme, limited (1-3) metastatic lesions, multiple (>3) metastatic lesions, carcinomatous lymphomatous meningitis, nonimmunosuppressed primary CNS lymphoma, and metastatic spine tumors; cervical cancer; chronic myelogenous leukemia (CML); colon cancer, rectal cancer, anal carcinoma; esophageal cancer; gastric (stomach) cancer; head and neck cancers, including ethmoid sinus tumors, maxillary sinus tumors, salivary gland tumors, cancer of the lip, cancer of the oral cavity, cancer of the oropharynx, cancer of the hypopharynx, occult primary, cancer of the glottic larynx, cancer of the supraglottic larynx, cancer of the nasopharynx, and advanced head and neck cancer; hepatobiliary cancers, including hepatocellular carcinoma, gallbladder cancer, intrahepatic cholangiocarcinoma, and extrahepatic cholangiocarcinoma; Hodgkin disease/lymphoma; kidney cancer; melanoma; multiple myeloma, systemic light chain amyloidosis, Waldenstrom's macroglobulinemia; myelodysplastic syndromes; neuroendocrine tumors, including multiple endocrine neoplasia, type 1, multiple endocrine neoplasia, type 2, carcinoid tumors, islet cell tumors, pheochromocytoma, poorly differentiated/small cell/atypical lung carcinoids; Non-Hodgkin's Lymphomas, including chronic lymphocytic leukemia/small lymphocytic lymphoma, follicular lymphoma, marginal zone lymphoma, mantle cell lymphoma, diffuse large B-Cell lymphoma, Burkitt's lymphoma, lymphoblastic lymphoma, AIDS-Related B-Cell lymphoma, peripheral T-Cell lymphoma, and mycosis fungoides/Sezary Syndrome; non-melanoma skin cancers, including basal and squamous cell skin cancers, dermatofibrosarcoma protuberans, Merkel cell carcinoma; non-small cell lung cancer (NSCLC), including thymic malignancies; occult primary; ovarian cancer, including epithelial ovarian cancer, borderline epithelial ovarian cancer (Low Malignant Potential), and less common ovarian histologies; pancreatic adenocarcinoma; prostate cancer; small cell lung cancer and lung neuroendocrine tumors; soft tissue sarcoma, including soft-tissue extremity, retroperitoneal, intra-abdominal sarcoma, and desmoid; testicular cancer; thymic malignancies, including thyroid carcinoma, nodule evaluation, papillary carcinoma, follicular carcinoma, Hürthle cell neoplasm, medullary carcinoma, and anaplastic carcinoma; uterine neoplasms, including endometrial cancer and uterine sarcoma.

Methods for Drug Screening and Development

The devices, methods, and systems of the disclosure provided can also include means for investigating the efficacy of drugs on sample or test subject. Generally, devices and methods of fOCT may be used for platform screening of drugs, which may include either biologics or small molecule. In some examples, fOCT may be useful in determining the efficacy of a potential drug target which may be designed to increase or decrease a particular molecular maker or analyte in a target. For example, if a VEGF inhibitor is screened for use in the retina, fOCT may be used to assess candidate molecules for potential efficacy, toxicity and dosing.

In some examples, a sample may include an in vitro cultured tissue graft, a harvested graft (e.g. from a cadaver, or an artificially grown tissue. In some examples, a test subject may include an animal, or genetically modified organism. In some examples, the genetically modified organism may be exhibit one or more disease states or symptoms for which drug efficacy is tested. The provided method can also include high-throughput screening of FDA approved off-label drugs, experimental drugs, treatment protocols or pharmaceutical reagents.

V. Software and Computer Systems for fOCT

In various examples, certain methods and systems may further include software programs on computer systems and use thereof. Accordingly, computerized control for the synchronization of system functions such as laser system operation, fluid control function, and/or data acquisition steps are within the bounds of the invention. The computer systems may be programmed to control the timing and coordination of delivery of sample to a detection system, and to control mechanisms for diverting selected samples into a different flow path. In some examples of the invention, the computer may also be programmed to store the data received from a detection system and/or process the data for subsequent analysis and display.

Figure 25:
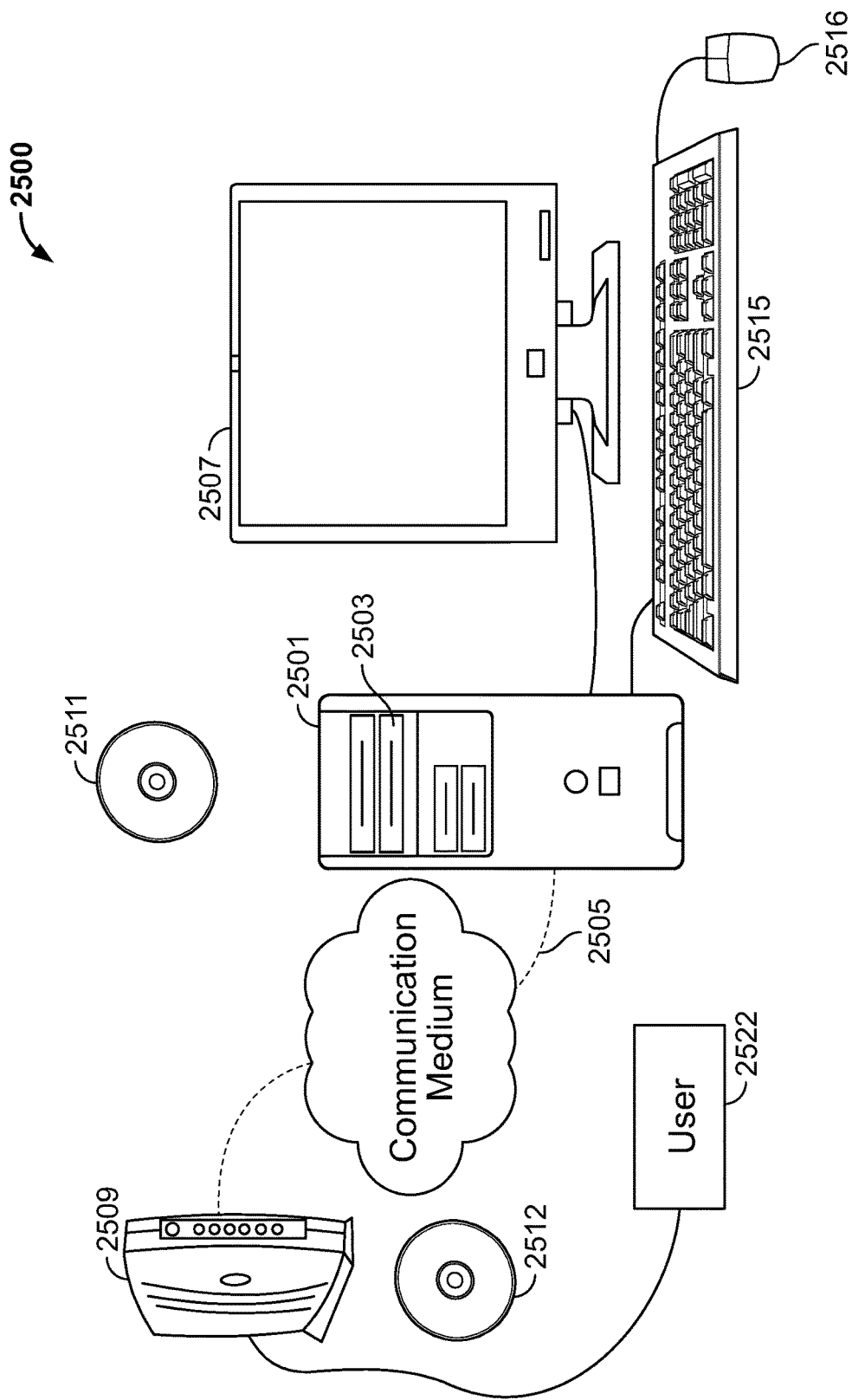
FIG. 25 illustrates a schematic of an example logical apparatus that can read instructions from media, connect to a network and store data generated by a fOCT device.

The computer system 2500 illustrated in FIG. 25 may be understood as a logical apparatus that can read instructions from media 2511 and/or a network port 2505, which can optionally be connected to server 2509 having fixed media 2512. The system, such as shown in FIG. 25 can include a CPU 2501, disk drives 2503, optional input devices such as keyboard 2515 and/or mouse 2516 and optional monitor 2507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 2522 as illustrated in FIG. 25.

Figure 29:
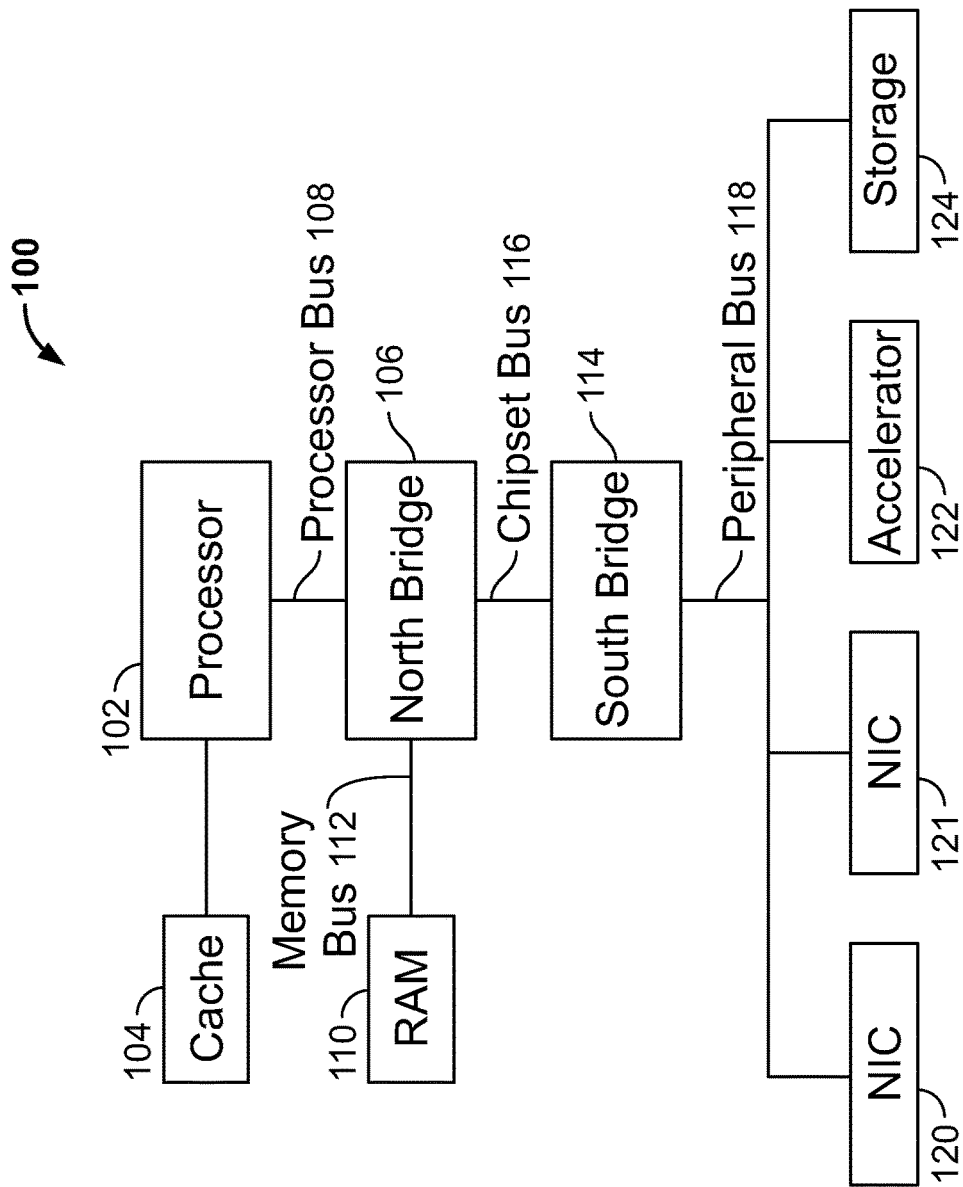
FIG. 29 is a block diagram illustrating a first example architecture of a computer system that can be used in connection with a fOCT device.

FIG. 29 is a block diagram illustrating a first example architecture of a computer system 100 that can be used in connection with example examples of the present invention. As depicted in FIG. 29, the example computer system can include a processor 102 for processing instructions. Non-limiting examples of processors include: Intel Xeon™ processor, AMD Opteron™ processor, Samsung 32-bit RISC ARM 1176JZ(F)-S v1 .O™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some examples, multiple processors or processors with multiple cores can also be used, whether in a single computer system, in a cluster, or distributed across systems over a network comprising a plurality of computers, cell phones, and/or personal data assistant devices.

As illustrated in FIG. 29, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some examples, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RANI 2910 and/or cache 104 for use by the processor. The system 100 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example examples of the presently disclosed technology.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 30:
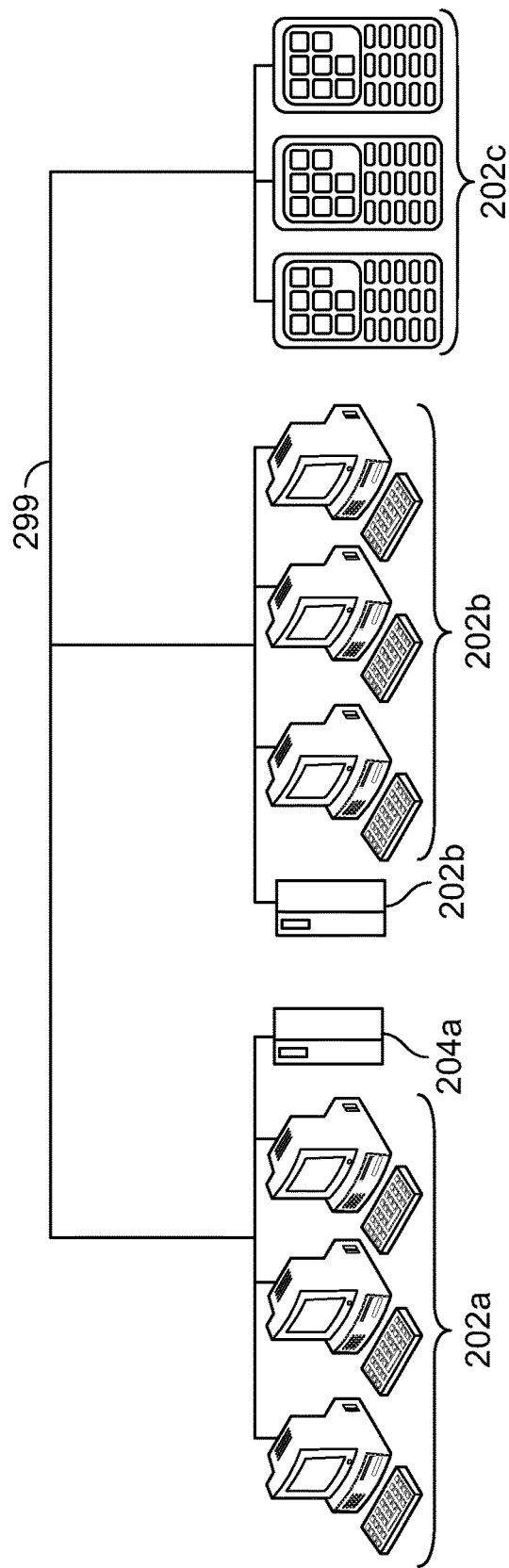
FIG. 30 is a diagram showing an example network with a plurality of computer systems, and a plurality of cell phones and personal data assistants configured with a fOCT device.

FIG. 30 is a diagram showing a network 3000 with a plurality of computer systems 3002a, and 3002b, a plurality of cell phones and personal data assistants 3002c, and Network Attached Storage (NAS) 3004a, and 3004b. In example examples, systems 3002a, 3002b, and 3002c can manage data storage and optimize data access for data stored in Network Attached Storage (NAS) 3004a and 3004b. A mathematical model can be used for the data and be evaluated using distributed parallel processing across computer systems 3002a, and 3002b, and cell phone and personal data assistant systems 3002c. Computer systems 3002a, and 3002b, and cell phone and personal data assistant systems 3002c can also provide parallel processing for adaptive data restructuring of the data stored in Network Attached Storage (NAS) 3004a and 3004b. FIG. 30 illustrates an example only, and a wide variety of other computer architectures and systems can be used in conjunction with the various examples of the presently disclosed technology. For example, a blade server can be used to provide parallel processing. Processor blades can be connected through a back plane to provide parallel processing. Storage can also be connected to the back plane or as Network Attached Storage (NAS) through a separate network interface.

In some example examples, processors can maintain separate memory spaces and transmit data through network interfaces, back plane or other connectors for parallel processing by other processors. In other examples, some or all of the processors can use a shared virtual address memory space.

Figure 31:
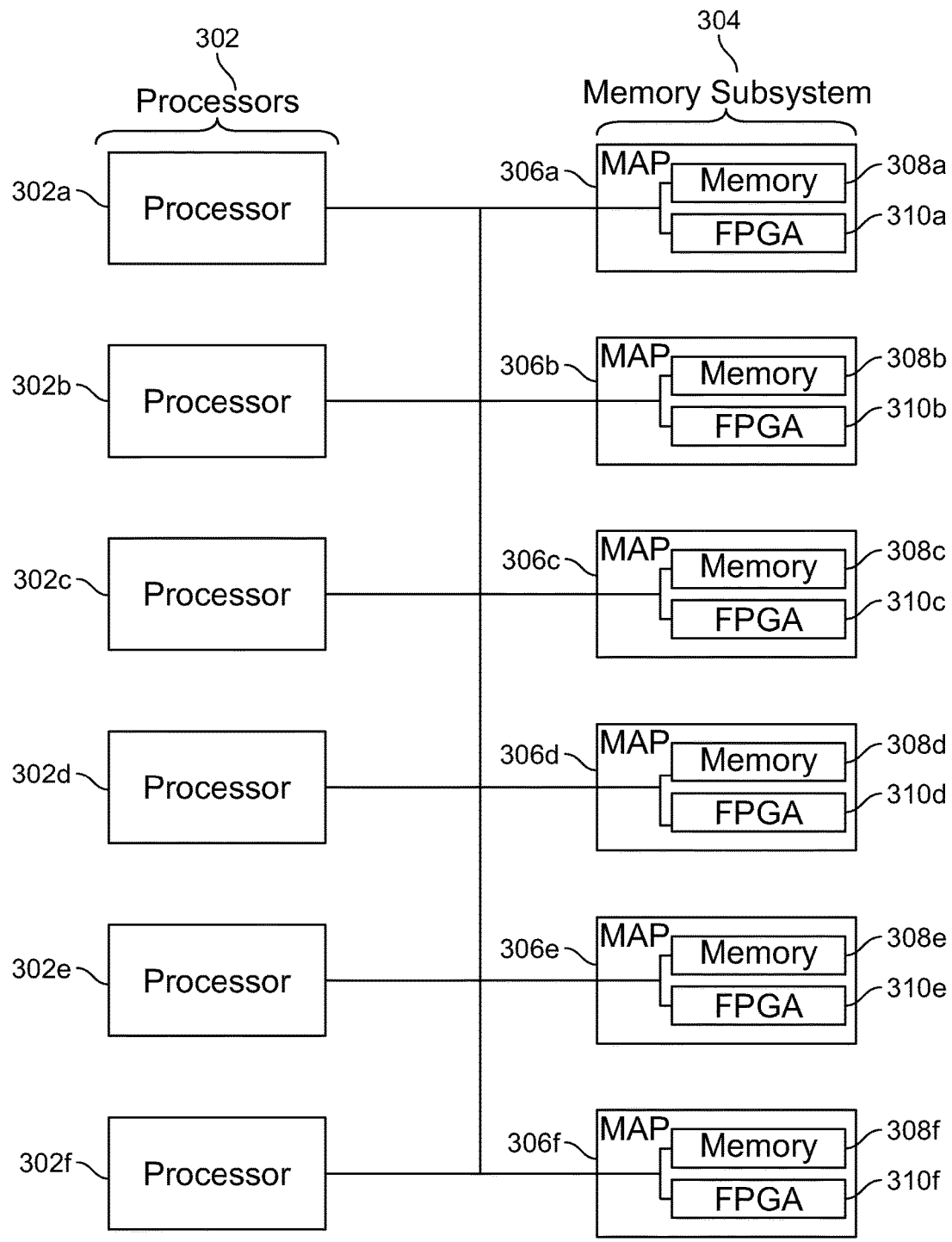
FIG. 31 is a block diagram of an example multiprocessor computer system configured with a fOCT device.

FIG. 31 is a block diagram of a multiprocessor computer system 302 using a shared virtual address memory space in accordance with an example fOCT device. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example examples. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example examples, including systems using any combination of general processors, co-processors, FPGAs and other programmable logic devices, system on chips (SOCs), application specific integrated circuits (ASICs), and other processing and logic elements. In some examples, all or part of the computer system can be implemented in software or hardware. Any variety of data storage media can be used in connection with example examples, including random access memory, hard drives, flash memory, tape drives, disk arrays, Network Attached Storage (NAS) and other local or distributed data storage devices and systems.

In example examples, the computer system can be implemented using software modules executing on any of the above or other computer architectures and systems. In other examples, the functions of the system can be implemented partially or completely in firmware, programmable logic devices such as field programmable gate arrays (FPGAs) as referenced in FIG. 31, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 29.

VI. Terminology

The terminology used therein is for the purpose of describing particular examples only and is not intended to be limiting of a device of this disclosure. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Several aspects of a device of this disclosure are described above with reference to example applications for illustration. It should be understood that numerous specific details, relationships, and methods are set forth to provide a full understanding of a device. One having ordinary skill in the relevant art, however, will readily recognize that a device can be practiced without one or more of the specific details or with other methods. This disclosure is not limited by the illustrated ordering of acts or events, as some acts may occur in different orders and/or concurrently with other acts or events. Furthermore, not all illustrated acts or events are required to implement a methodology in accordance with this disclosure.

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another example. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

EXAMPLES

Example 1

This example describes a method to measure and analyze OCT signals to estimate optical absorption properties of whole blood. In vivo retinal oximetry by vis-OCT (fOCT comprising visible light) was performed, using a comprehensive analytical model describing both the scattering and absorption from whole blood, as well as blood vessel scattering. The packing factor due to multiple optical scattering by blood cells was also included in this model.

Figure 12:
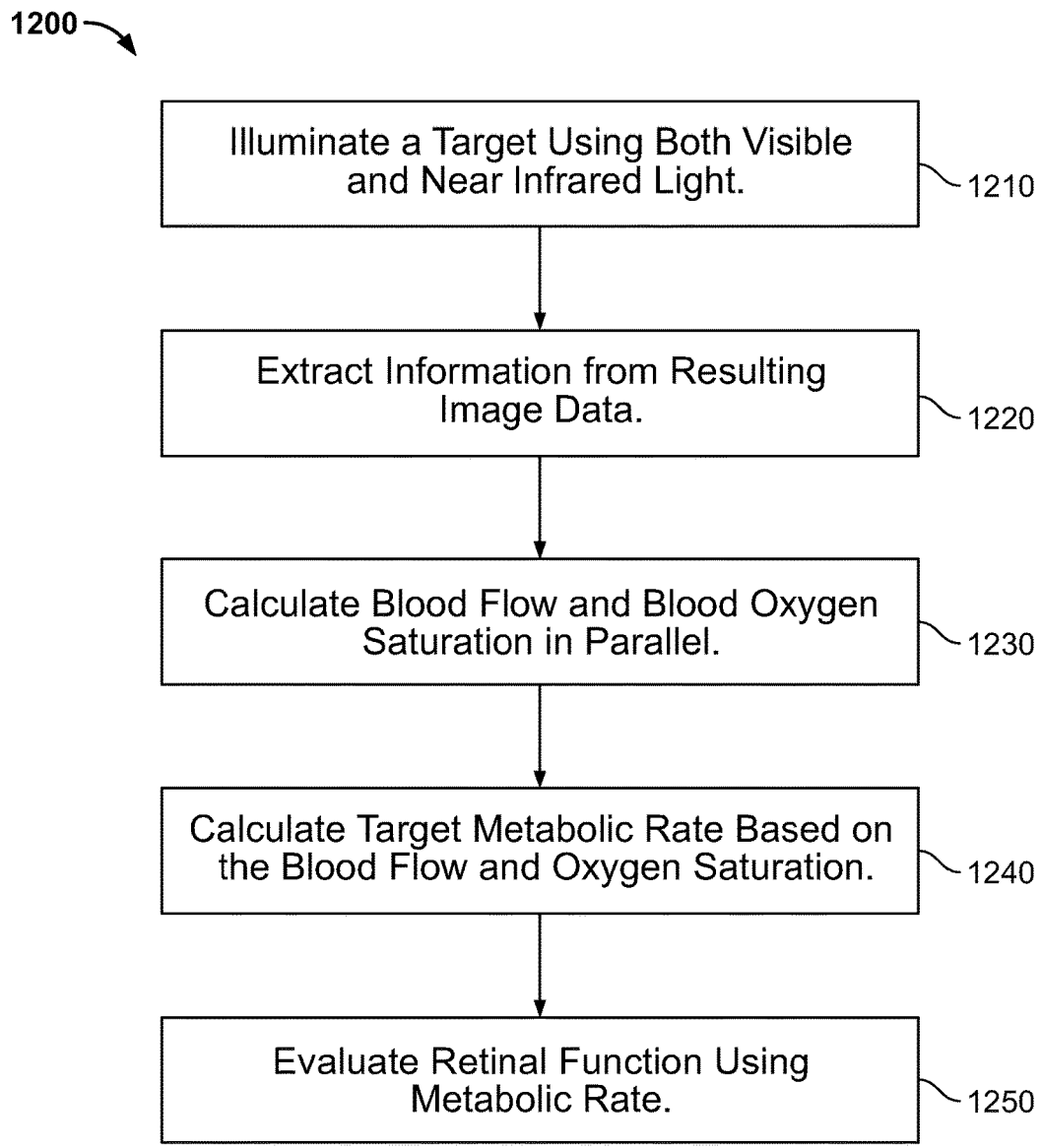
FIG. 12 is a flow diagram of an example method for metabolic functional OCT.

The principle of vis-OCT oximetry is illustrated in FIG. 12. The incident light reflected from the bottom vessel wall double-passed the vessel lumen. The spectrum of reflected light was extracted by a series of short-time Fourier transforms (STFT), which was formulated as:

$$I^2 = I_0^2 R_0 r \exp[-2nd\,\mu_{HbO2}(sO_2) - 2nd\,\mu_{Hb}(1-sO_2)]$$

where $I_0$ is the incident intensity on the retina. The optical attenuation by ocular lens and vitreous chamber were ignored and thus the source spectrum was taken as $I_0$; $R_0$ is the reference arm reflectance; n is the mean refractive index of the blood (~1.35); d [mm] is the vessel diameter; r [dimensionless] is the reflectance at the vessel wall, whose scattering spectrum can be modeled as a power law under the first-order Born approximation $r(\lambda) = A\lambda^{-a}$ where A is a constant. The optical attenuation coefficient $\mu$ [mm$^{-1}$] combines the absorption ($\mu_a$) and scattering coefficients ($\mu_s$) of whole blood, which are both wavelength- and oxygenation-dependent. The subscripts Hb and HbO$_2$ denote the contribution from deoxygenated and oxygenated blood, respectively. By taking the natural log and plugging in the above expressions, Eq. 1 becomes $$\ln\left(\frac{I(\lambda)}{I_0(\lambda)}\right) = -nd[sO_2 \cdot \mu_{HbO2}(\lambda) + (1-sO_2)\cdot \mu_{Hb}(\lambda)] - \frac{1}{2}a\ln(\lambda) + \frac{1}{2}\ln(AR_0).$$

A least-squares (LS) fit can then be performed to fit the spectrum and obtain sO$_2$, a, and ln(AR$_0$). The spectra of 11 is equal to $\mu = \mu_a + W\mu_s$, where W is blood cell packing factor that weights the scattering spectrum.

In this example, the setup consisted of a free-space spectral-domain OCT system FIG. 1, implemented with a supercontinuum source (SuperK, NKT photonics). The spectral range was centered at 585 nm with an 85-nm FWHM bandwidth. The theoretical axial resolution was 1.5 μm in air and was measured to be 1.7 μm. A 2 k pixel line scan CCD (Aviiva, SM2, e2v) was used in a home-made spectrometer. The A-line rate was 24 kHz. To acquire a 3D image consisting 256×256 A-lines, the acquisition time was 2.7 s. Pigmented rats were imaged (Long Evans rat, 500 g, Harlan Laboratories) for in vivo experiments.

vis-OCT data was performed with the following steps. The raw spectra were first normalized by the source spectrum and the DC components were subtracted. After 3D images were acquired, the fundus image was obtained by mean intensity projection and the center line of each blood vessel was digitally identified. Finally, OCT spectra were extracted from the bottom vessel wall along the center lines by STFT with a Gaussian window size $k_w=0.32$ μm$^{-1}$ (17 nm at 585 nm), relaxing the axial resolution (in air) to ~8.9 μm. The spectra was averaged from each vessel for a robust estimation, and applied LS from 540 to 610 nm to retrieve sO$_2$.

Figure 16B:
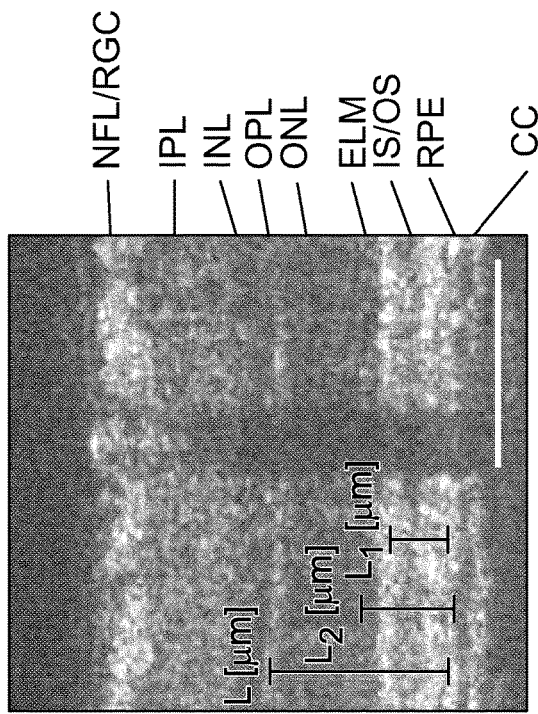
FIG. 16b is an example B-scan indicating various histological layers of the retina.
Figure 16A:
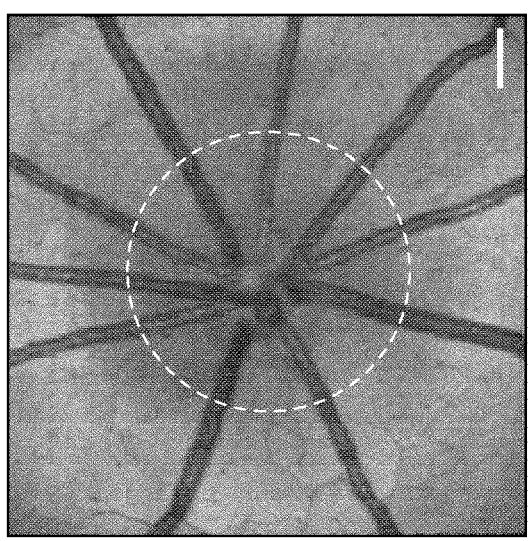
FIG. 16a is an example fundus image with vis-OCT and the circular white line represents a B-scan trajectory.
Figure 16C:
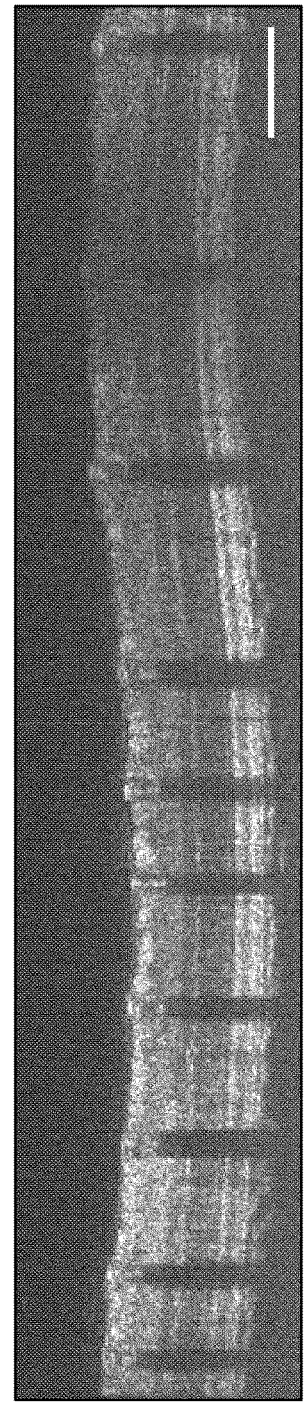
FIG. 16c is an example B-scan showing individual vessels.
Figure 17:
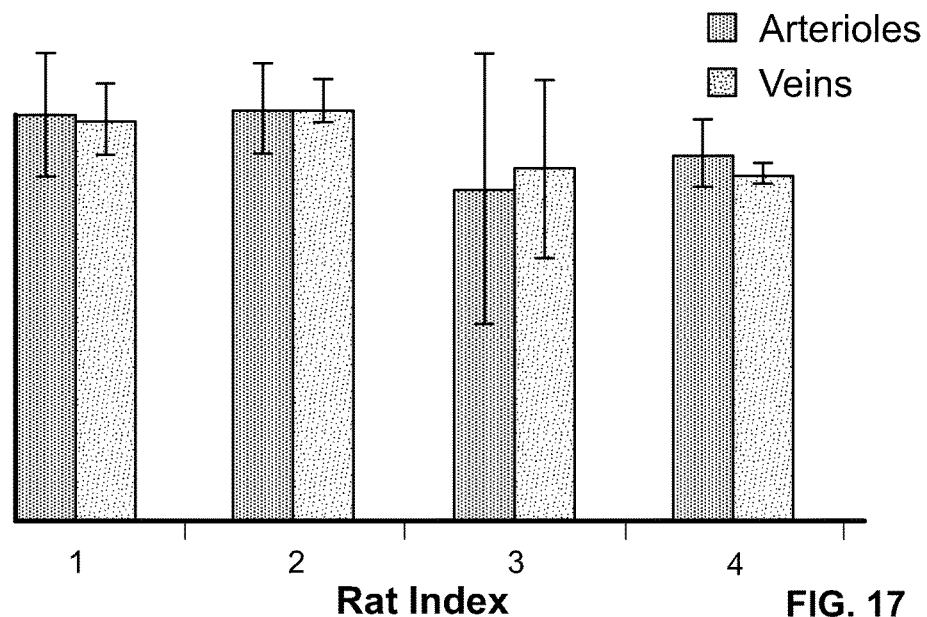
FIG. 17 is graph showing example differences in retinal flow measurements between major arterioles and veins in rats.
Figure 18A:
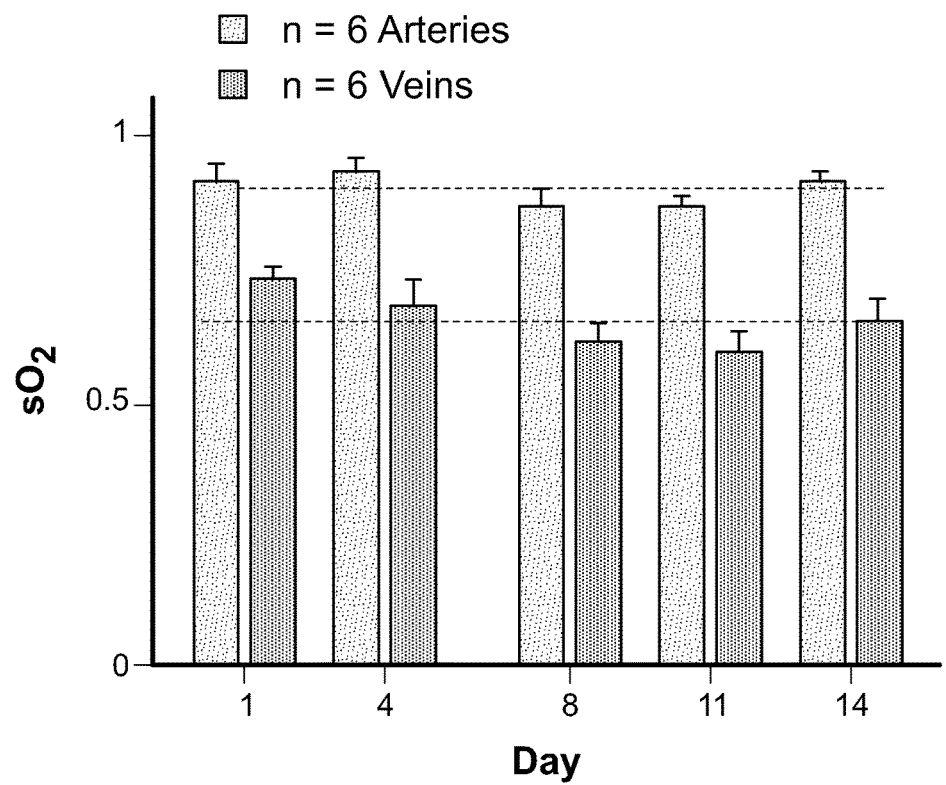
FIG. 18a is an example longitudinal stability study on $sO_2$.
Figure 18B:
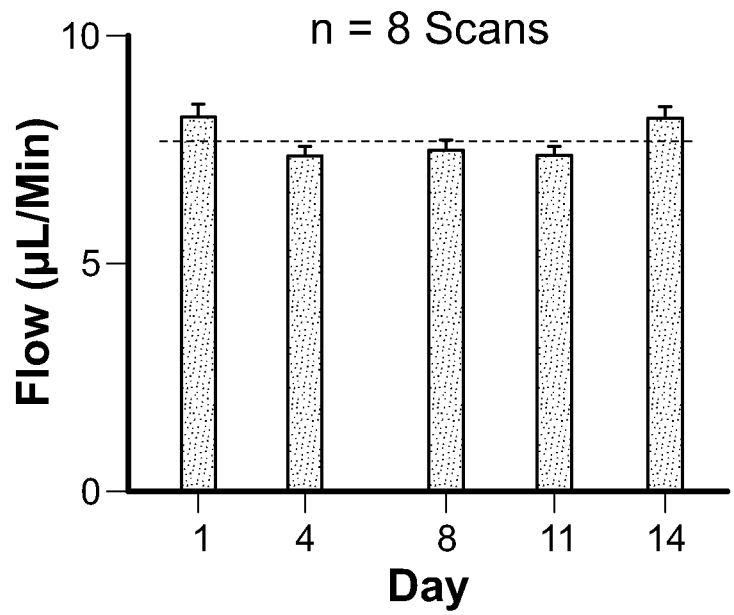
FIG. 18b is an example longitudinal stability study on blood flow.
Figure 18C:
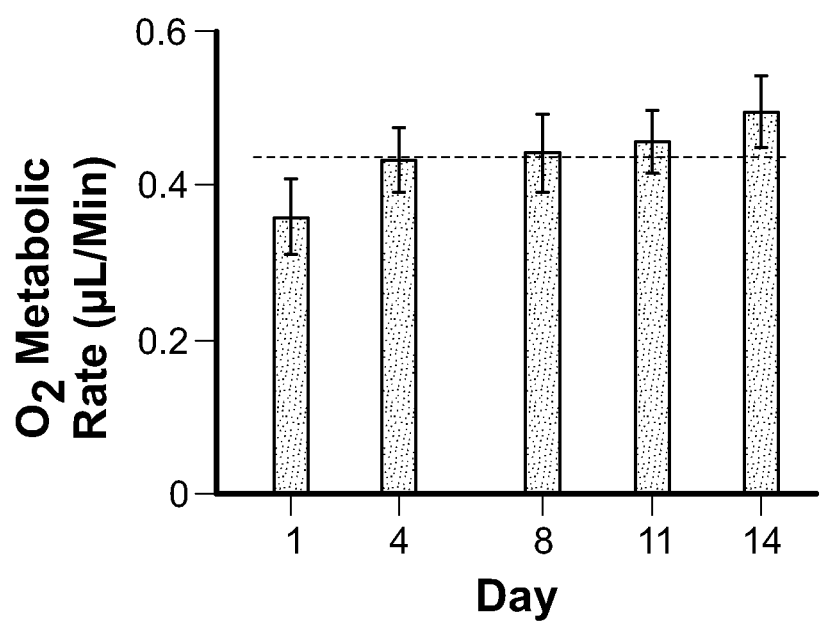
FIG. 18c is an example longitudinal stability study on $rMRO_2$.

How blood optical scattering and blood cell packing factor affect the spectrum of μ was observed. According to the Kramers-Kronig relationship, the absorption of hemoglobin affects blood optical scattering, and thus causes an oxygenation-dependent optical scattering spectrum. The spectra of $\mu_a$ and $\mu_s$ was calculated from oxygenated and deoxygenated blood as previously described, with plasma refractive index set at 1.35. Furthermore, due to multiple scattering effects of densely packed blood cells, the scattering coefficient in whole blood was weighted by a packing factor W ($0 \le W \le 1$). The expression of is corrected as $\mu = \mu_a + W\mu_s$, where W depends on the volume fraction of the red blood cells in whole blood (hematocrit) H. Thus, the spectrum of μ is a function of W. With increasing packing factor, the spectrum of μ red-shifted and the entire spectral shape altered as well. The value of W was varied from 0 to 1 and LS fit was performed, while the mean value and standard deviation of sO$_2$ from the major arteries and veins were plotted. The mean spectral residuals from LS fit for every vessel were also calculated. All the mean residuals for arteries and veins were averaged (FIG. 10). When W=0.2, the variation of calculated oxygenation (error bar) from both arteries and veins reached their minima as well as the fitting residuals. The fitting resulted from an artery and vein (No. 3 and No. 6 in FIG. 11) and were sampled. When W=0.2, the hematocrit was calculated as 35% in the cylindrical particle model, 30% in the spherical particle model. FIG. 11 showed in vivo results of vis-OCT oximetry. An OCT fundus image is displayed in grayscale (FIG. 11) in inversed contrast. The bright blood vessel structure corresponds to the strong optical attenuation in blood. As a comparison, we sectioned the 3D OCT volume from depth range 160-250 μm (correspond to the IS/OS junction to the RPE layer) and projected the mean intensity. As a result, the contrast from the microvasculature was enhanced (FIG. 16). Also, mean sO$_2$ values in major vessels were quantified and the pseudo-color map of sO$_2$ was overlaid in FIG. 16. A circular scanning pattern around the optic disk was used (the circle in FIG. 16) with 4096 A-lines, so that all the major vessels could be sampled. We expanded the circular scan into a B-scan image where the vessel index corresponds to the numbers in FIG. 18. The values of sO$_2$ in individual vessels are given with red and blue color labeling arteries and vein (FIG. 17). On average, sO$_2$ from arteries and veins were 95±3% and 72±7%, respectively. The standard deviation from the veins was higher than for arteries, which was mostly caused by the flatter spectrum of μ. The alternating artery and vein pattern can be confirmed by the size of the vessels (i.e. arteries have smaller diameter than veins due to their contractility).

The algorithm and model proposed herein were based on the fact that the bottom blood vessel wall can be imaged with a high signal to noise ratio (SNR). In the current example, sufficient SNR for sO$_2$ was achieved with calculation in vessels with diameters between 30 μm to 130 μm.

Example 2

This example demonstrated that visible-light optical coherence tomography (vis-OCT) can quantify rMRO$_2$ in vivo through the concurrent measurement of the blood flow and sO$_2$ from retinal circulation. The 3D imaging capability allowed vis-OCT to recover optical spectra specifically from blood vessels and eliminate the confounding signal from other retinal layers. The rMRO$_2$ was obtained by combining the sO$_2$ measurement with the OCT flow measurement. The blood flow and sO$_2$ measurements were validated both in vitro and in vivo. As proof of principle, we investigated the metabolic response to progressive hypoxia challenges and changes in the balance between the retinal and choroidal circulations during hypoxia. The experimental results were cross-validated by an oxygen-diffusion model derived from direct measurements of the oxygen tension profile in rat outer retina using microelectrodes.

Figure 22D:
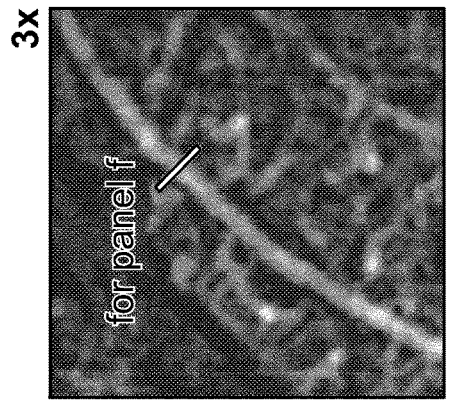
Figure 22E:
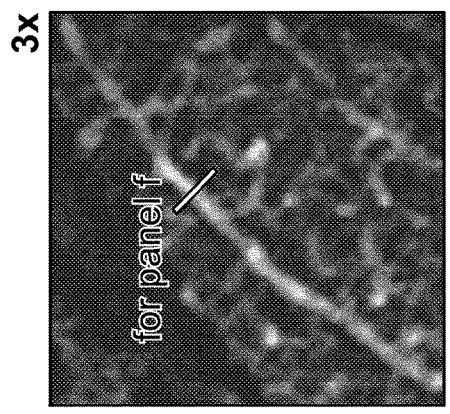
FIG. 22e illustrates an example magnified view of the insert in FIG. 22b.
Figure 22F:
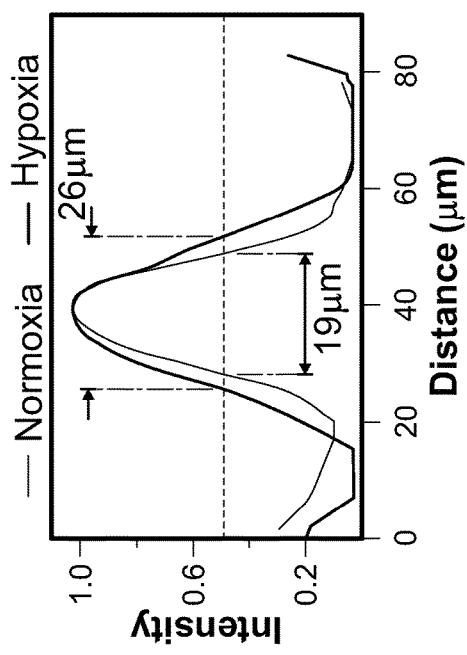
FIG. 22f illustrates an example comparison of the arteriole diameter under normoxia and hypoxia.
Figure 23A:
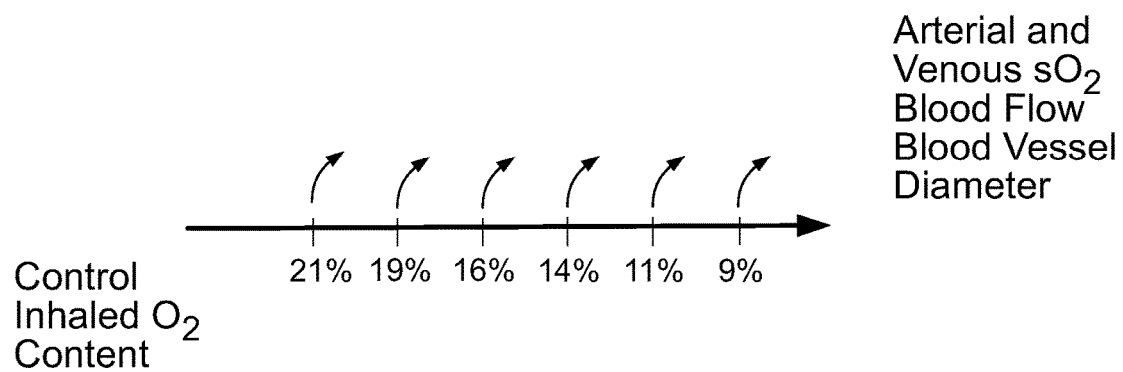
FIG. 23a reflects example retinal oxygen consumption derived from retinal circulation and responds to systemic oxygen tension.
Figure 23B:
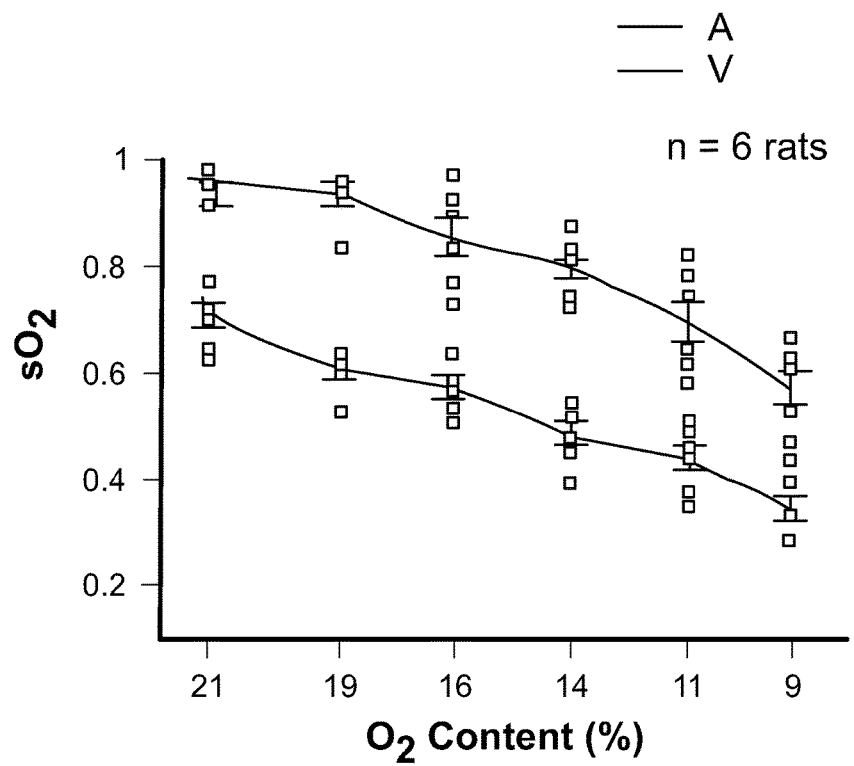
FIG. 23b illustrates example $sO_2$ changes under reduce oxygen content.
Figure 23C:
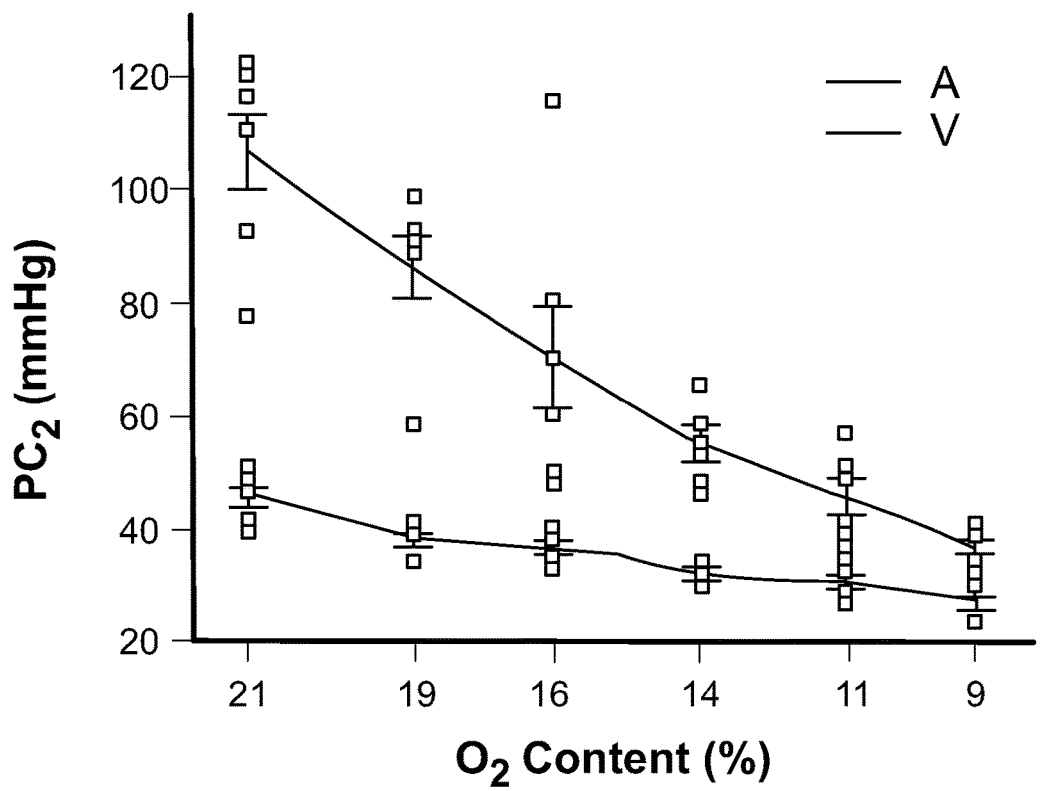
FIG. 23c illustrates example $PO_2$ changes under reduce oxygen content.
Figure 23D:
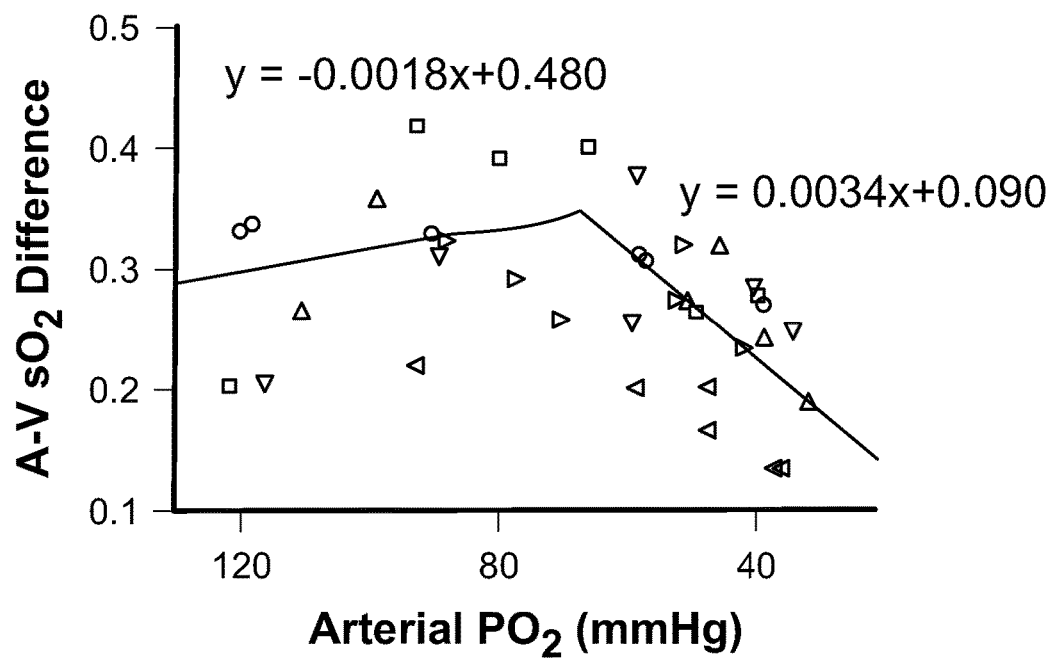
FIG. 23d illustrates an example corresponding progression of arteriovenous oxygenation difference.
Figure 23E:
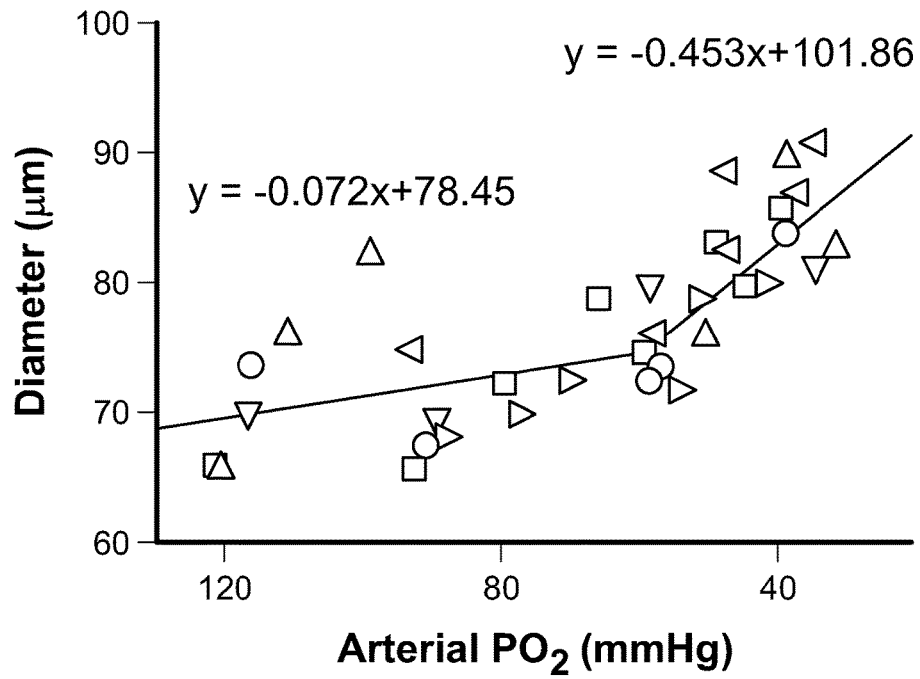
FIG. 23e illustrates an example average diameter of major retinal blood vessels.
Figure 23F:
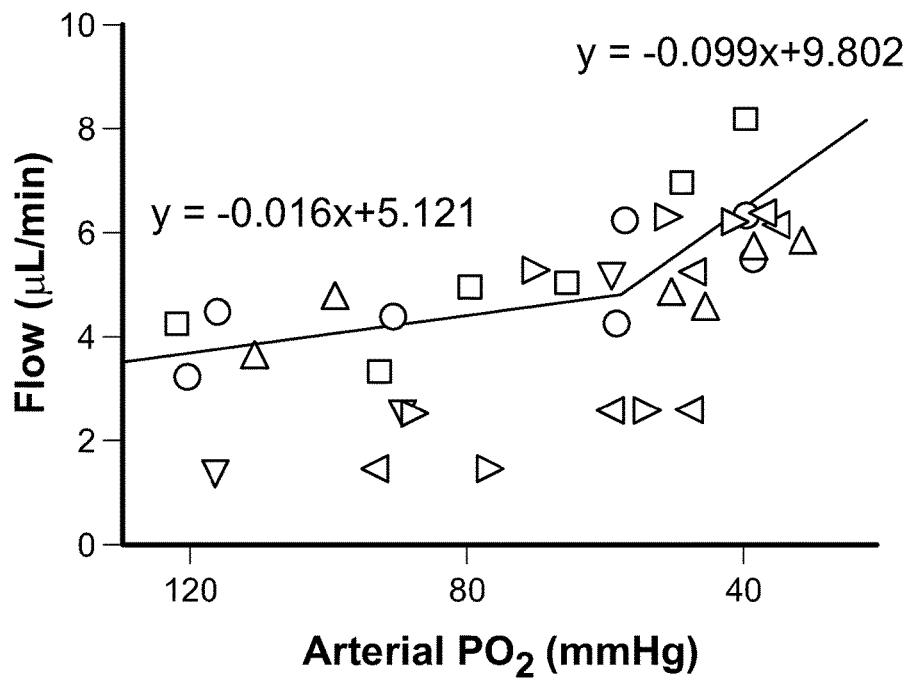
FIG. 23f illustrates an example retinal blood flow.
Figure 23G:
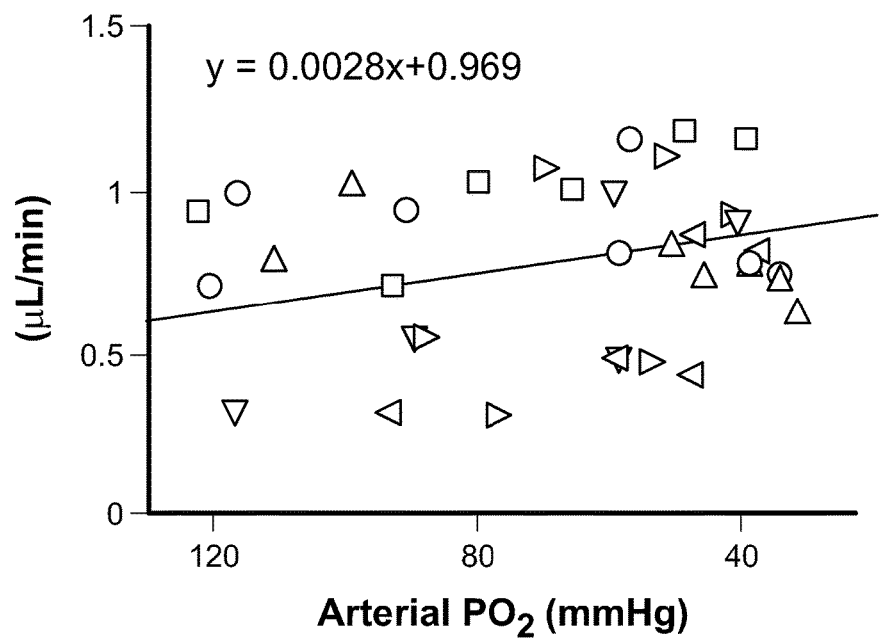
FIG. 23g illustrates an example of oxygen delivery from arterial vessels.
Figure 23H:
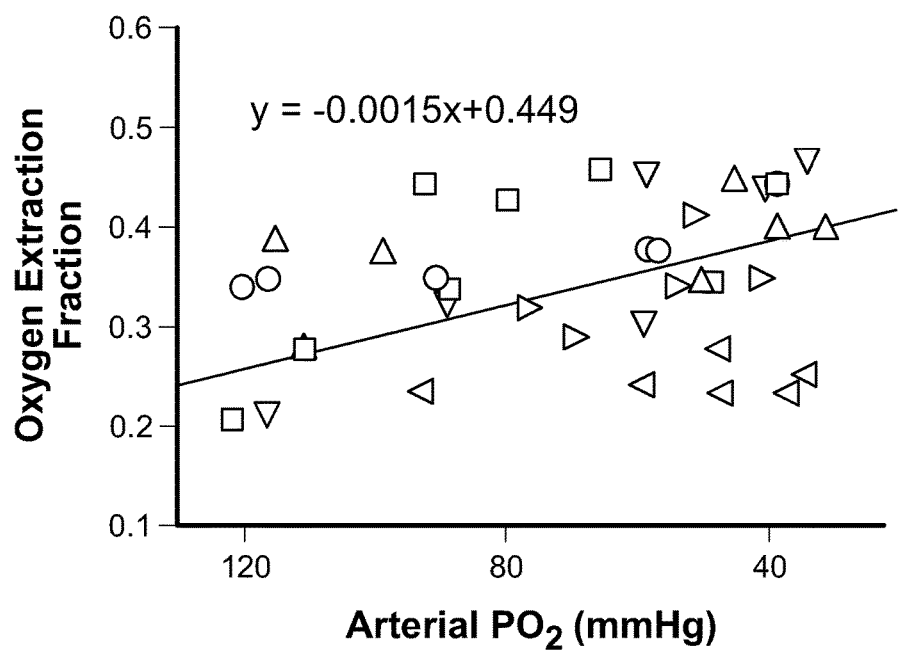
FIG. 23h illustrates an example oxygen extraction fraction.
Figure 23I:
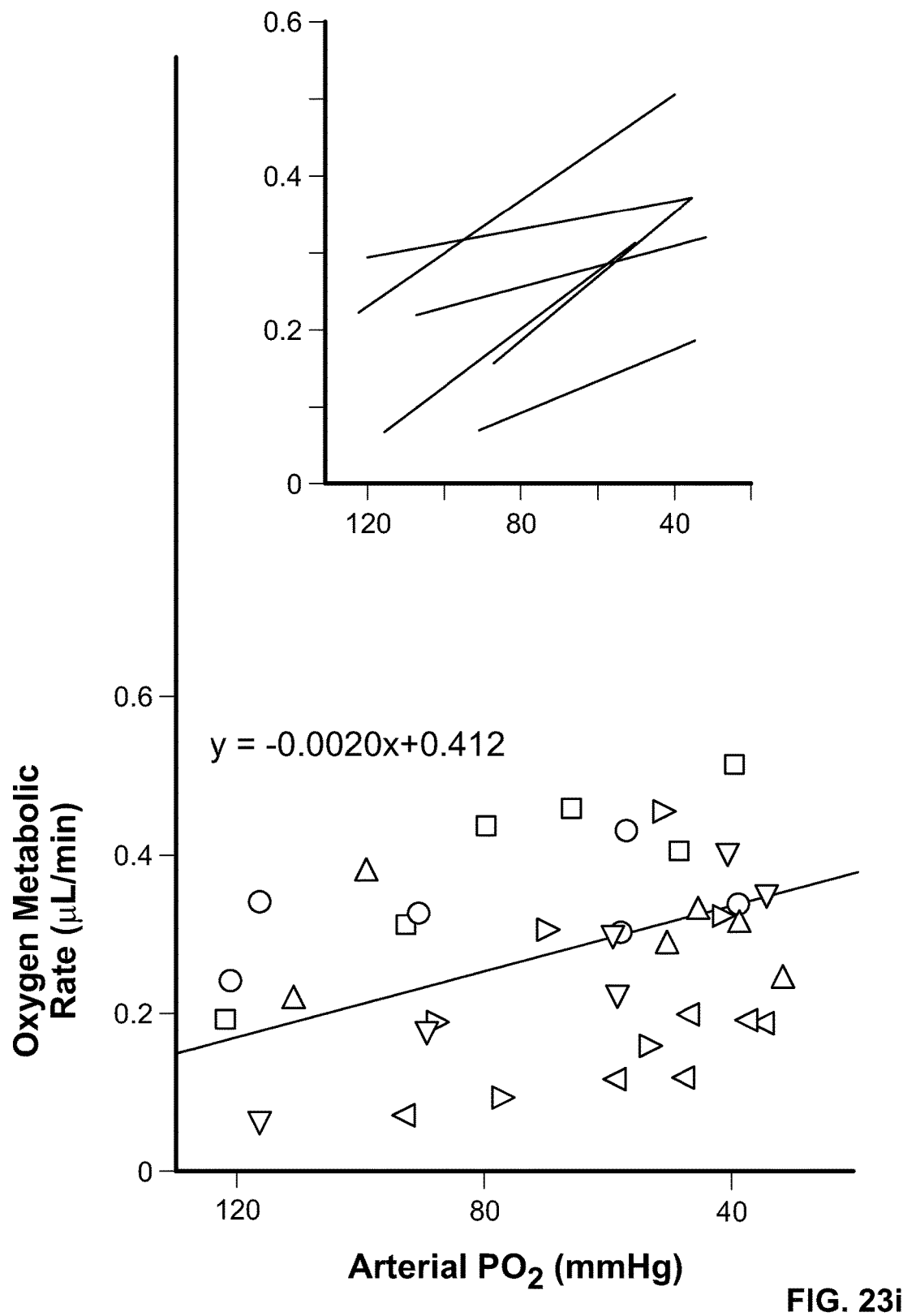
FIG. 23i illustrates an example of retinal oxygen metabolism from retinal circulation.
Figure 24A:
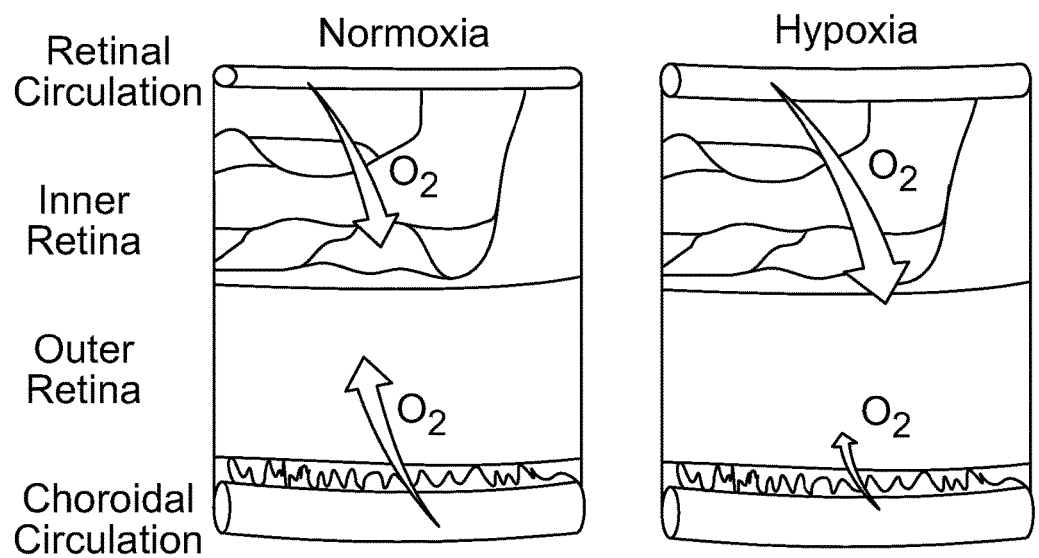
FIG. 24a shows an example schematic of oxygen supply balance changes between retinal and choroidal circulation under hypoxia. Under systemic hypoxia, the retinal circulation provides more oxygen to the outer retina to compensate the deficit from choroidal circulation.
Figure 24B:
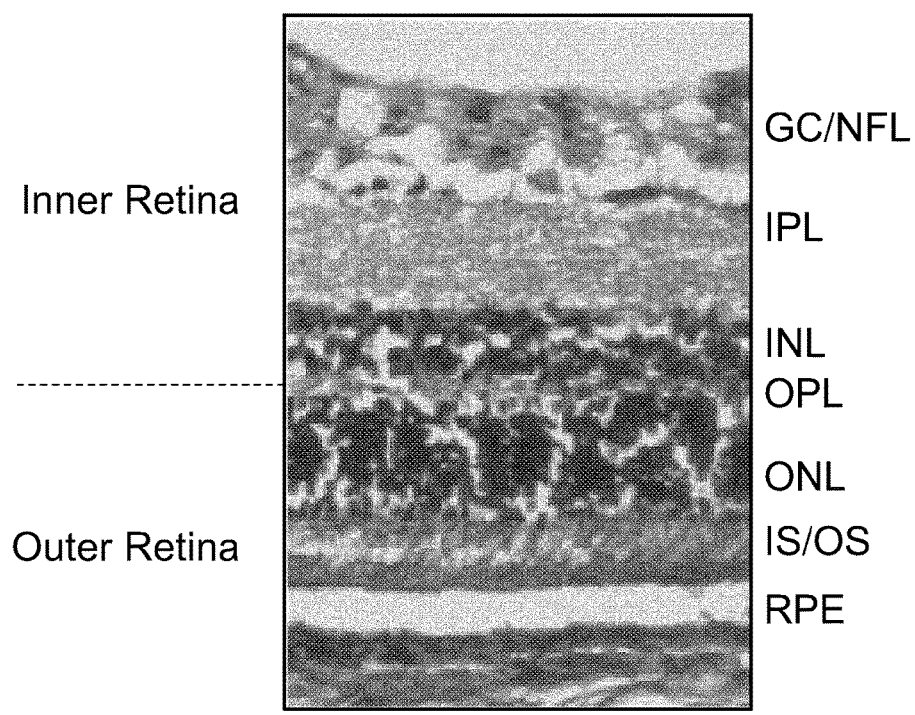
FIG. 24b shows an example anatomical structure of a rat retina.
Figure 24C:
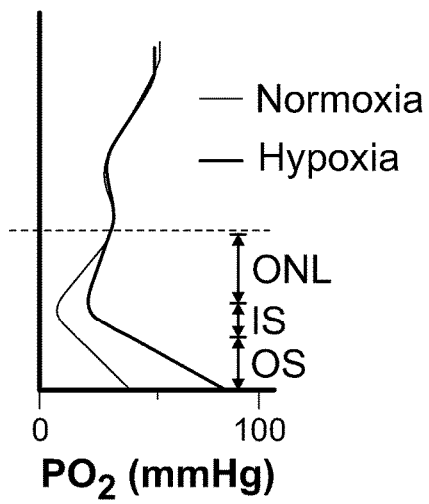
FIG. 24c shows an example simulated $PO_2$ profile across the retina.
Figure 24D:
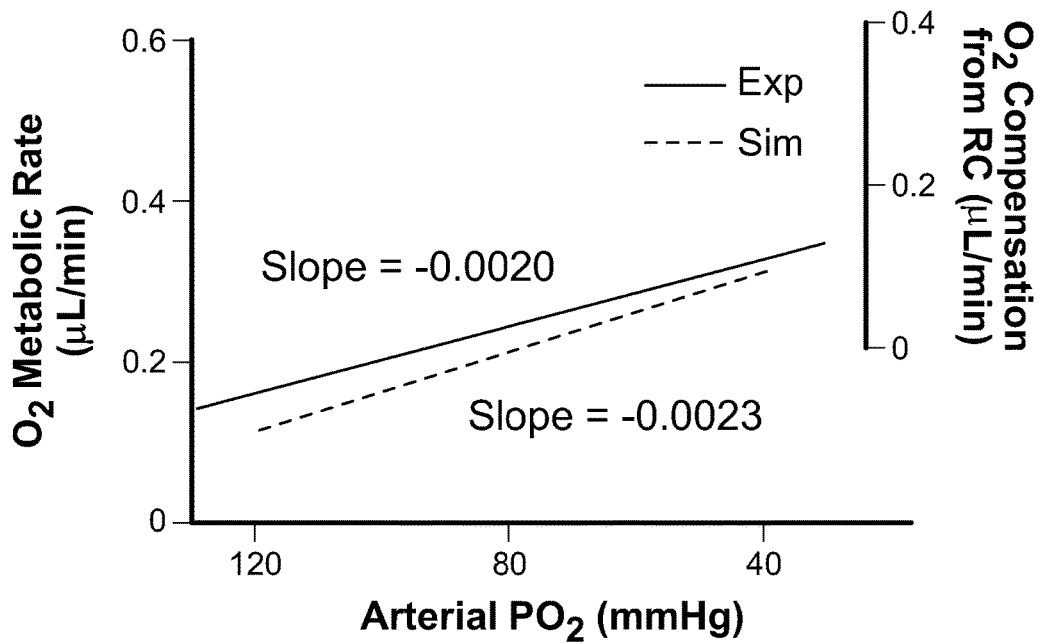
FIG. 24d shows an example graph of arterial PO2 versus O2 metabolic rate.

The 3D structure of the rat retina was imaged and rMRO$_2$ quantified using vis-OCT (FIG. 22). A focused broadband laser was scanned across the retina to provide transverse (x,y) discrimination. The reflectance at depth (z), A-line, was reconstructed by the interference between the illustrated light and the reference light. Each 3D measurement (2.8 mm by 2.8 mm by 1 mm in x, y, z) took only several seconds (typically 2.5 s) with 98 fps frame rate, allowing monitoring of $rMRO_2$ with high temporal resolution. To quantify the $rMRO_2$ (gas volume of oxygen consumed per unit time, mL/min), two parameters were measured from the retinal circulation: total retinal blood flow F [JIL/min] and relative $sO_2$ [percent]. The $rMRO_2$ was calculated according to the following equation:

$$rMRO_2 = 1.34 \times C_{Hb} \times F \times C(s_aO_2 - s_vO_2),$$

where $C_{Hb}$ is the hemoglobin concentration [g/JIL], and 1.34 is the oxygen-binding capacity of hemoglobin [mL/g]. The subscript of a and v denotes arterial and venous $sO_2$. Blood flow is the product of the cross-sectional vessel area (s) and velocity (v), where s was calculated from the tomographic image and v was measured based on the phase variation from the moving blood cells as described herein. The contrast for $sO_2$ is from the distinct absorption spectra from oxy- and deoxyhemoglobin. By fitting the blood spectra extracted from blood vessels, the percentage of oxyhemoglobin in total hemoglobin ($sO_2$ by definition) was calculated.

Because of the strong attenuation of blood in the visible-light range, a shadow was cast underneath the vessels when the light passed by. An en face slice was used in deep retina as a screen to capture this "shadow effect" and create a 2D "print" of the microvasculature. The large retinal vessels were visualized clearly as well as the details of the capillary network. This method does not require a high-density scanning protocol as reported previously, and yet it provides robust label-free microangiography.

To Test the accuracy of $sO_2$ and blood flow measurements, flow calibration in vitro was performed, where a turbid aqueous solution (1% intralipid) was pumped through a capillary tube by syringe pump, and then the vis-OCT flow measurement was calibrated against the pump flow settings. For $sO_2$, bovine whole blood with controlled $sO_2$ flowed through the capillary tube and we compared the vis-OCT $sO_2$ quantification with the results derived from blood analyzer readings. The accuracy was within 0.25 f·l/min and 4% for velocity and $sO_2$ measurements, respectively.

To accomplish the flow measurement in vivo, a dual-circle scanning pattern was adopted around the optic nerve head (ONH). Because retinal blood vessels run radially from the ONH, each circle crossed all of the arteries and veins and allowed capture of total retinal blood flow (FIG. 21). The displacement of vessels between the two circular scans provided the vessel directionality for absolute flow. Eight dual-circle scans were performed with an A-line rate of 70 kHz. The high-speed scanning allowed capture of the pulsatile profile of the blood flow (FIG. 21). A simultaneous EKG recording was referenced to provide the timing of the cardiac cycle. The pulsatile flow pattern from an artery coincided well with the EKG profile, with a slight delay (~0.1 s) between the peaks of the flow and the QRS complex. This delay was caused by the time taken by the sequence of atrioventricular node discharge, ventricular contraction, and the pressure propagation from heart to head. A Fourier transform of the pulsatile profile was taken and the distinct peaks from all the arterial flows were consistent, indicating that the heart rate was 4.36 $s^{-1}$. The flow readings over the eight dual-circle scans for each vessel were averaged and summed total arterial and venous flows. The total blood flows from the arterial and venous vessels were within measurement precision (±0.38 f·L/min averaged from five rats)

To verify the consistency of the inward and outward blood flow, the value of total averaged blood flow was calculated at 6-8 JIL/min (n=5 rats), which agreed well with the reported data using the same anesthesia protocol.

Two experimental protocols were used to examine the accuracy of our in vivo $sO_2$ measurement. In the first protocol, oxygen content was gradually changed in the inhaled air from 21% to 10% in several steps. After each adjustment, the animals were allowed to adapt to the changed air and re-stabilize for ~2 mins. The systemic peripheral arterial oxygenation ($spO_2$) was monitored by a pulse oximeter attached to the rat rear leg. At each inhalation condition, arterial $sO_2$ was measured by vis-OCT and compared TO the averaged values with the pulse oximeter $spO_2$ readings (FIG. 23). The linear correlation ($R2=0.839$) established the responsiveness of our $sO_2$ measurements to the blood oxygenation changes. In the second protocol, the inhaled oxygen was changed from 21% to 100%, and then from 21% to 10% (FIG. 23). Arterial $sO_2$ was roughly unchanged from 21% to 100%, but dropped significantly at 10% oxygen (0.95±0.02 at 21% oxygen, 0.95±0.01 at 100% oxygen, 0.96±0.01 at recovery 21%, and 0.59±0.03 at 10% oxygen); on the other hand, the venous $sO_2$ changed with the changing oxygen content (0.75±0.03 at 21% oxygen, 0.86±0.01 at 100% oxygen, 0.74±0.02 at recovery 21%, and 0.48±0.01 at 10% oxygen).

A critical factor for any longitudinal study is the stability of measurements repeated over time. In order to test the repeatability, a time course experiment was performed in which five measurements were taken for the same subject over the span of two weeks. The standard deviations of various parameters for the five measurements were all within 11% of the mean values (7.4% for arterial $sO_2$, 6.4% for venous $sO_2$, 9% for blood flow, and 11% for $rMRO_2$).

Having characterized the accuracy of blood flow and $sO_2$ measurement, systemic oxygen tension and how it affects $rMRO_2$ during hypoxia was studied. Although previous studies have shown hemodynamic (increased retinal blood flow) and vascular changes (increased vessel diameter) under low oxygen supply, the comprehensive observation of how inner retinal oxygen consumption reacts to limited oxygen supply has never been reported. In addition, the retinal circulation provides very little oxygen to the outer retina under light-adapted conditions, but how this changes during hypoxia had not known.

The retinal vascular changes under hypoxia were observed (FIG. 22) The major arteries and veins dilated during hypoxia. The average vessel diameter increased by ~35% for arteries (59.7±1.5 f·m during normoxia, 80.8±2.0 f·m during hypoxia), and ~16% for veins (77.4±2.0 f·m during normoxia, 90.2±2.3 f·m during hypoxia). In normoxia, the arteries were curved due to a constrictive vascular tone; under hypoxia, straighter arteries indicated relaxation of vascular smooth muscle. In addition, the dilation could also be observed in smaller arterioles (FIG. 22), which allows more blood flow into the deep retinal capillary network in the outer plexiform layer (OPL).

In order to progressively track the auto-regulatory response, a "step-down" hypoxia challenge protocol was performed, in which the inhaled oxygen content was reduced from 21% (normoxia) to 9% (hypoxia) in six steps (21%, 19%, 16%, 14%, 11% and 9%) (FIG. 23). The measurements were taken at each step and the progressing trends of sO$_2$, blood flow, vessel diameter, and rMR O$_2$ were quantified (n=6 rats). The entire experimental protocol took less than 30 min.

Figure 19:
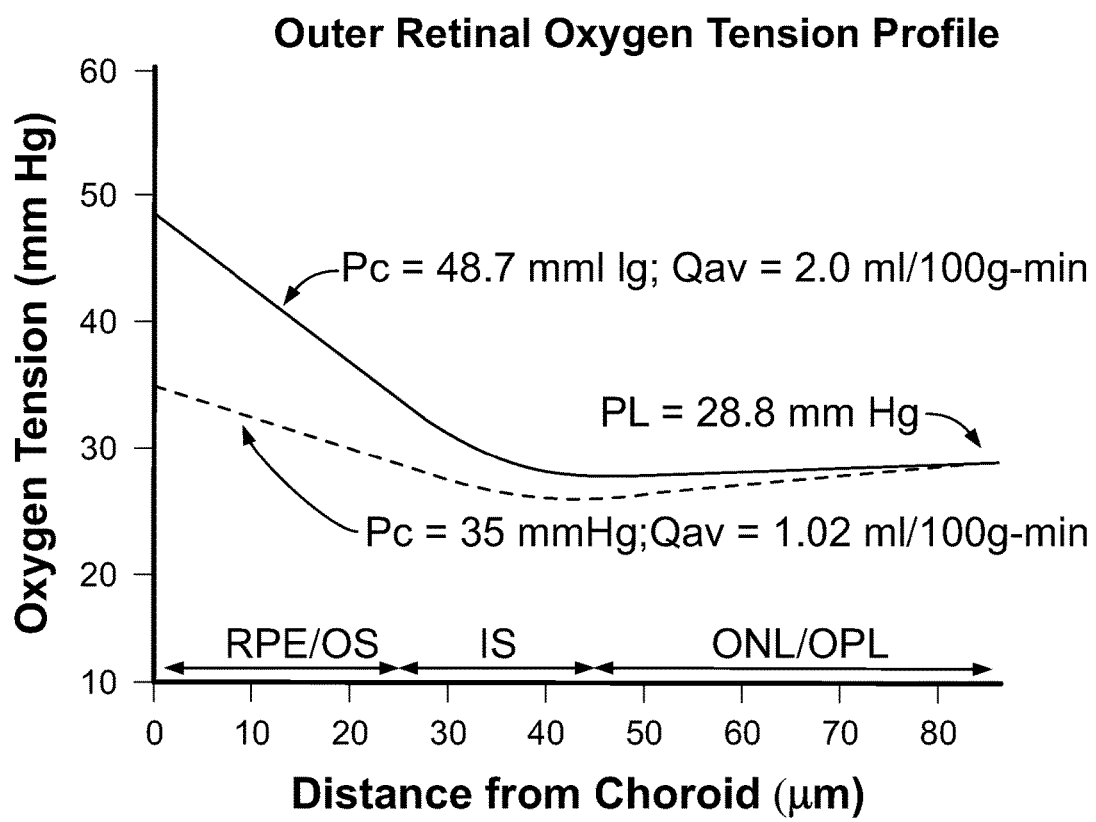
FIG. 19 is a graph of example simulated oxygen tension $PO_2$ profiles as function of retinal depth. Retinal pigmented epithelium (RPE)/outer segment of photoreceptor (OS) layer (Layer 1), and the outer nuclear layer (ONL)/outer plexiform layer (OPL) (Layer 3) has the linear profile of $PO_2$; while inner segment of photoreceptor (OS) (Layer 2) has a quadratic $PO_2$ profile. Solid line is the $PO2$ profile under normal air breathing, and the dashed line is under systemic hypoxia at $PaO_2=72$ mmHg. The choroidal oxygen tension (Pc) is proportional to the systemic $PaO_2$. The oxygen tension at the interface between outer and inner retina (PL) is considered to be the same due to the autoregulation of the retinal circulation.

As expected, both arterial and venous sO$_2$ decreased with the reduced oxygen (FIG. 19). The venous sO$_2$ decreased almost linearly, while the arterial sO$_2$ decreased more quickly when the oxygen content was below 14%. Because the oxygen partial pressure (PO$_2$) may be the direct stimulus to autoregulation and has more biological meaning, sO$_2$ readings were translated to PO$_2$ based on the hemoglobin dissociation curve, defined by Hill's equation with n=2.8 and P50=32.9. For arteries and veins, the average PO$_2$ was 106.5±6.6 and 45.5±1.8 mmHg, respectively, and dropped almost linearly to 36.8±1.5 and 26.3±0.9 mmHg with 9% inhaled O$_2$. The arteriovenous sO$_2$ difference exhibited a two-segment pattern that increased slightly when the arterial PO$_2$ was higher than 65 mmHg and decreased quickly thereafter. When examined, the progressive trend of vessel diameter with arterial PO$_2$, also had a similar two-segment pattern where the dilation became more dramatic during severe hypoxia. A consequence of vessel dilation was the reduction in vascular resistance, which allowed more blood flow (FIG. 23). The increased blood flow compensated for the deficiency in saO$_2$, and the total oxygen delivery (defined by 1.34×F$_{artery}$×saO$_2$) by arterial vessels was maintained (slope=−0.0028). The oxygen extraction fraction (defined by the ratio of arteriovenous sO$_2$ difference over arterial sO$_2$) increased, indicating that the retina extracted oxygen more efficiently under hypoxia. Finally, the oxygen consumption by the retina from the retinal circulation also increased with the decreased arterial PO$_2$ (FIG. 23). The slopes in FIG. 23 are significantly different from zero (P=0.033, 0.001 and <0.001, respectively), with the scatter contributed largely by the vertical offset of the data for individual animals, each of which exhibited the same trend in slope (illustrated in the inset to FIG. 23i).

vis-OCT was used to accurately measure rMRO$_2$ and visualize the microvasculature. This method allowed monitoring of retinal function via its oxygen consumption with high temporal resolution. The response of rMRO$_2$ to the systemic PO$_2$ changes and observed increased oxygen consumption from the retinal circulation under hypoxia were measured with high accuracy.

The increased extraction of oxygen during hypoxia may be a result of the increased oxygen supply to the outer retina from retinal circulation when the oxygen supply from the choroidal circulation falls. This balance between the retinal and choroidal circulations may not have an active compensation during hypoxia; rather, it may result from the different ways in which the two circulations behave in response to oxygen deficiency. The choroidal circulation has a small arteriovenous sO$_2$ difference and very little autoregulatory response, while the retinal circulation has a large arteriovenous sO$_2$ difference and is well regulated. When the systemic PO$_2$ decreases, the oxygen supply from the chorioicapillaris falls, reducing the PO$_2$ around photoreceptors and increasing the gradient to drive oxygen toward the photoreceptors from the retinal capillaries in the OPL (FIGS. 24a-d). To determine whether this balancing mechanism could quantitatively account for the increased oxygen extraction from the retinal circulation, we conducted a simulation.

The outer retina is avascular and its oxygen supply solely depends on diffusion. Anatomically, the outer retina can be divided further into three layers (FIGS. 24a-d). From the choroidal side, they are photoreceptor outer segments (OS, Layer 1), photoreceptor inner segments (IS, Layer 2), and the outer nuclear layer (ONL, Layer 3). The retinal oxygen profile across the outer retina has been characterized by microelectrode measurements in various mammalian species, including rat (FIG. 19). The PO$_2$ is maximal at the choroid and falls with a steep gradient towards the inner segment of the photoreceptors, where oxygen is consumed. In the outer nuclear layer, PO$_2$ also exhibited a gradient toward the inner segment of the photoreceptors. This oxygen profile can be modeled by a one-dimensional three-layer diffusion model based on Fick's second law, $$Q = Dk\frac{d^2P}{d^2x},$$

where Q is oxygen consumption normalized by the tissue weight [ml·min$^{-1}$·100 g$^{-1}$], D is diffusivity of oxygen [1.97e-5 cm$^2$/s], k is solubility of oxygen [2.4 ml O$_2$/(ml retina·mmHg)], P is PO$_2$ [mmHg], and x is the distance from the choroid. By fitting the diffusion model to the measured PO$_2$ curves, the average oxygen consumption in outer retina Q$_{av}$ under light adaption has been characterized. In addition, the fraction of Q$_{av}$ provided from the retinal circulation also can be calculated given the thickness of the three layers in the outer retina, PO$_2$ values at boundaries of the outer retina, and Q$_{av}$. Using parameter values measured from rat retina, and assuming that choroidal PO$_2$ decreased, hypoxic profiles were simulated across the outer retina. This allowed us to estimate the additional oxygen that would be provided to the outer retina by the retinal circulation and compare it with our experimental data. The changes in retinal oxygen extraction with decreased arterial PO$_2$ were almost identical (slope=−0.0020 and −0.0023) in the simulation and the experiment, respectively.

Example 3

The ability to quantify rMRO$_2$ with fOCT and vis-OCT can provide valuable insight into the pathogenesis of various retinal diseases, particularly DR and glaucoma. A key element is understanding the causal relationship between retinal cell degeneration and hemodynamic dysregulation. For example in DR, it is known that endothelial and pericyte disruption occurs in early-stage DR, but the hemodynamic changes that occur are unclear. Some studies showed increased retinal blood flow and suggested that the higher blood flow and high glucose level causes hyperperfusion, which further damages the endothelivam and pericytes; however, contradicting data exist that show decreased blood flow is one of the earliest changes in the diabetic retina. The hypothesis is that the loss of pericytes in the early phase of the disease reduces oxygen consumption, which may paradoxically lead to increased oxygenation of the retina. This might create a relative hyperoxia, resulting in vasoconstriction and reduced blood flow. Similarly, in glaucoma, there is degeneration of retinal ganglion cells and their axons. Although altered blood flow and vasculature were observed in glaucoma, their causal relationship to ganglion cell death remains unknown. A fOCT device configured for retinal scanning is setup to diagnose, monitor an treat patients for a variety of ophthalmic diseases. By measuring rMRO$_2$, metabolic function and blood flow is measured and related to a number of diseases where the retina experience a change in oxygen consumption as a result of disease or susceptibility to disease. The connection between hemodynamic dysregulation and retinal cell degeneration. With improved understanding of retinal metabolic function, improved approaches to early disease detection and therapeutic strategies can be designed.

Example 4

In this example, a probe configured with vis-OCT measurements was configured to image endocervical mucus and potential interaction with infectious disease such as HIV. Despite the current methods using exogenous substances to prevent AIDS infection (e.g., vaginal barrier devices and antibiotics), there are more and more investigations focus on the intrinsic AIDS defending systems. Among them, endocervical mucus serves as an important barrier. Consisting of various glycoprotein and antibodies, the normal mucus is very effective at trapping and neutralizing invading infectious microbes.

One critical parameter indicating the integrity of the endocervical barrier is the mucus thickness, which is still challenging to monitor to date, partially because its gel-like appearance prevents direct measurement by visual inspection. In this study visible light optical coherence tomography (vis-OCT) was to dynamically measure the mucus thickness in vivo with lateral resolution and micrometer-scale depth resolution. The mucus contained intrinsic contrast originating from the cell debris and undissolvable substance, whose characteristic back-scattering pattern differentiates it from underlying tissue, allowing quantitative measurement of its thickness. Vis-OCT was capable of visualizing and performing endocervical mucus thickness measurements ex vivo. Also the vis-OCT probe achieved real-time dynamic monitoring of mucus secreting and hydrolysis. The vis-OCT system was successfully miniaturize for an endoscopic probe that can was easily inserted into macaque FRT.

Figure 26A:
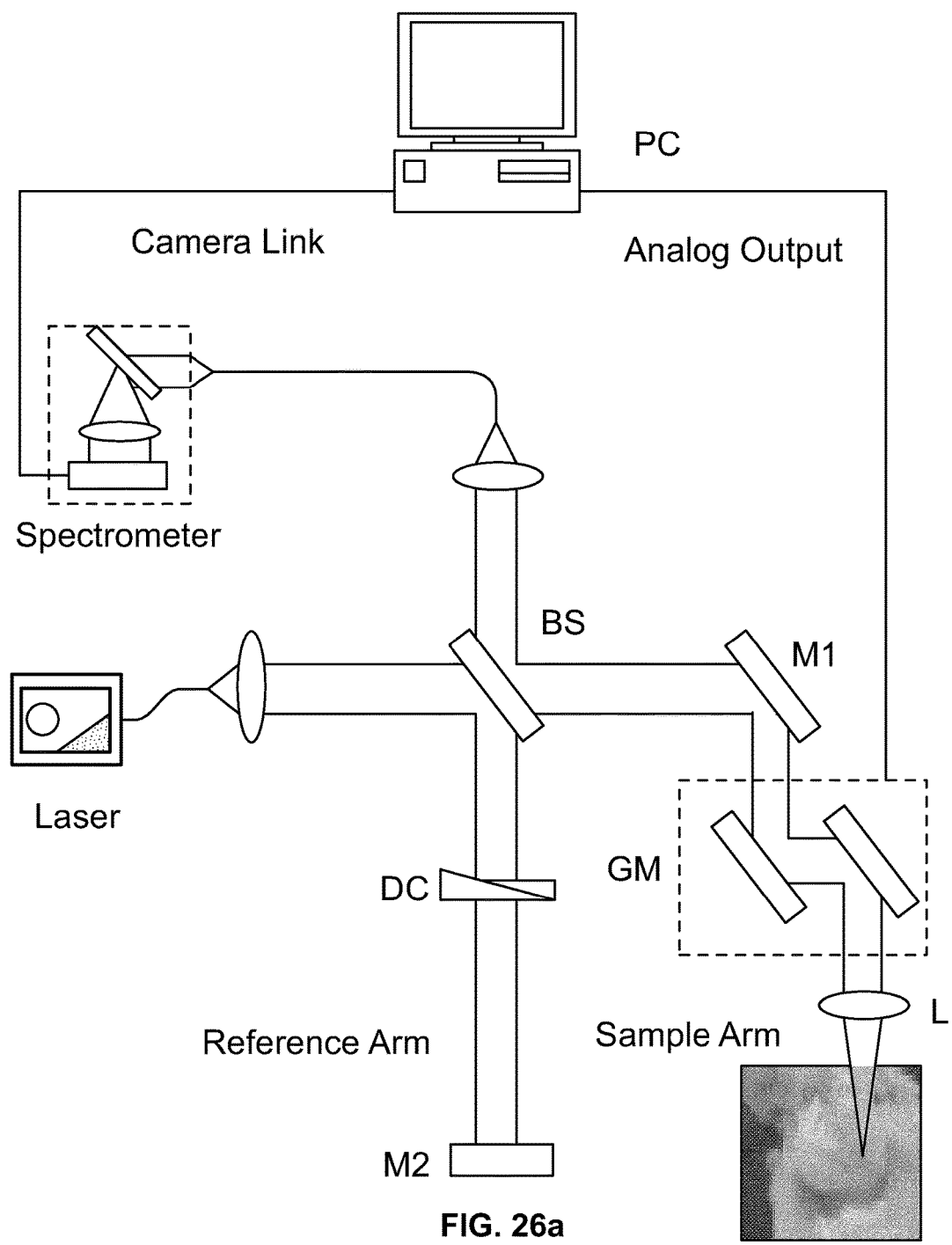
FIG. 26a illustrates example dynamic monitoring of mucus thickness using OCT.
Figure 26B:
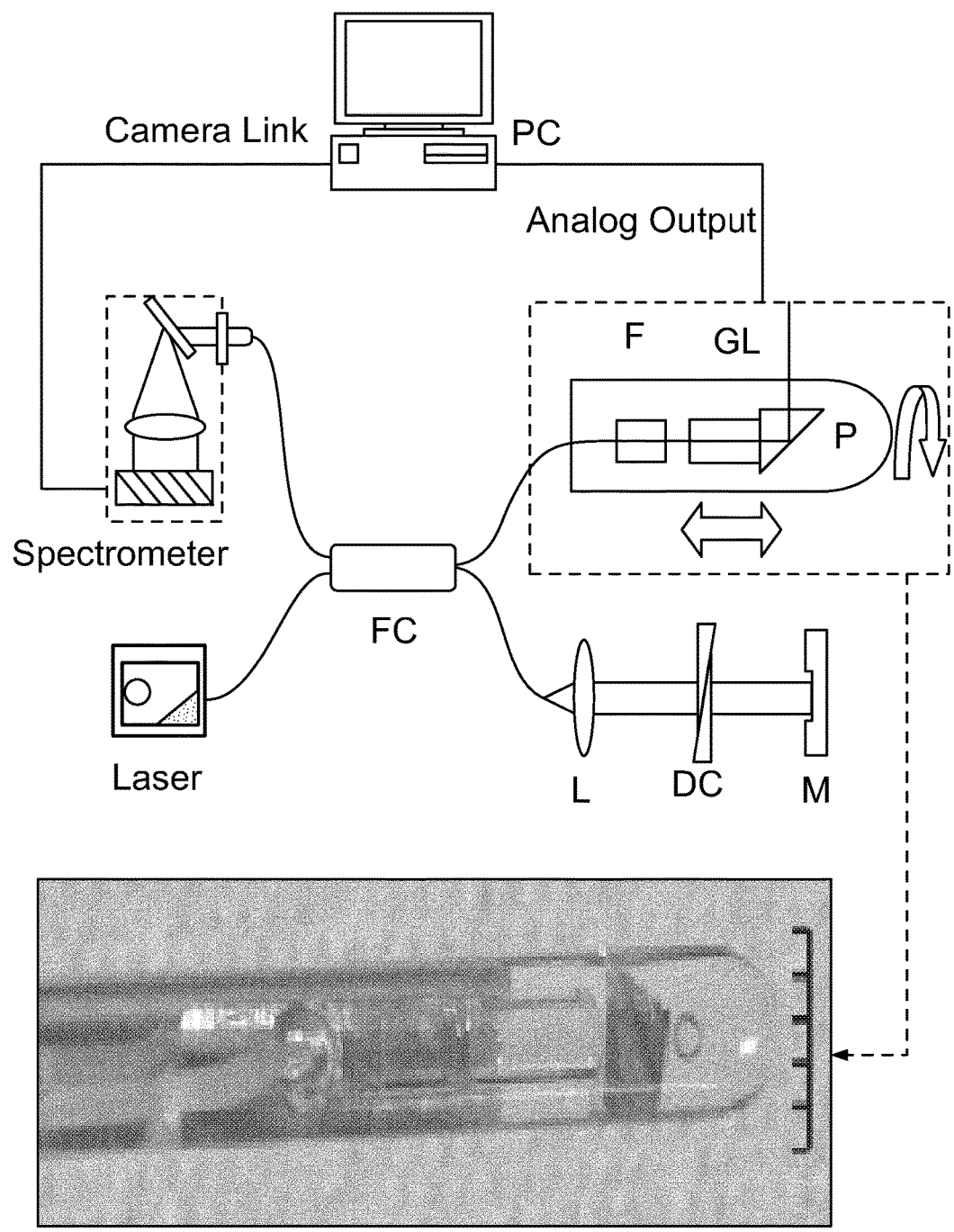
FIG. 26b illustrates an example schematic diagram and photograph of an example endoscopic NIR-OCT probe.

A prototype endoscopic OCT probe was constructed that can perform linear and circular scans. To achieve higher penetration depth for in situ measurement, near infrared (NIR) light source was also used. The endoscopic probe was a fiber-based, miniature sized lens-prism complex. The schematic diagram of the OCT probe was shown in FIG. 26. A gradient-index (GRIN) lens was used to obtain light focusing. A right-angle prism is attached on the GRIN lens to achieve desired side-view imaging. The lens-prism complex is mounted on a rotating shaft, which was driven by a step motor to control the circular scan. A motorized linear translation stage was used to move the probe from the proximal to distal position, allowing a 3-dimensional cylindrical scanning pattern to be performed. The photo in FIG. 26 shows the dimension of a finished prototype endoscopic OCT probe. The outer diameter of the probe was roughly 4.5 mm, which can be easily inserted into the macaque FRT.

FIG. 27 shows a cross sectional B-scan frame using the bench top OCT system. Endocervical tissue structures including epithelium and lamina propria (LP) were visualized in OCT images. Mucus was recognized by a strong reflection from mucus surface and scattered cell debris within mucus.

The relative mucus thickness change when cultured with PBS was plotted in FIG. 27. During the imaging sequence, a nearly linear increase of mucus thickness within the first 30 minutes of the procedure was observed with up to threefold thickness. The change in the thickness was statistically significant for these time points (P<0.01). The mucus thickness reached a plateau thereafter.

Figure 28A:
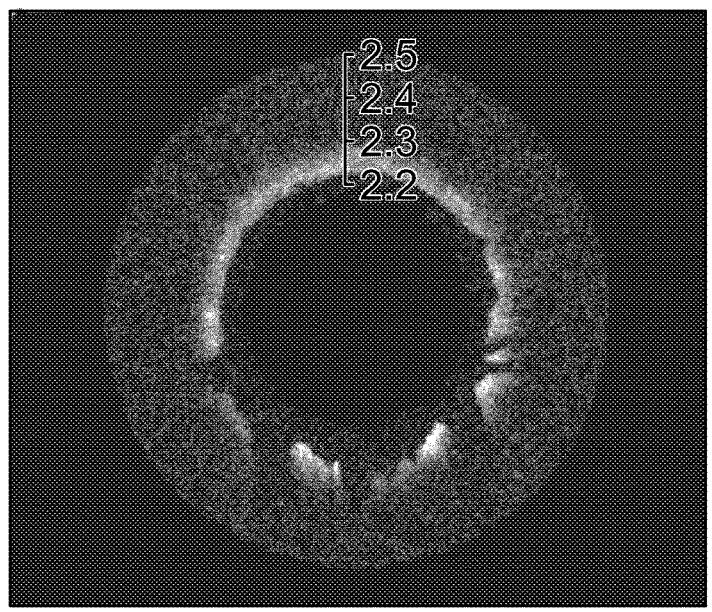
FIG. 28a shows an example endoscopic NIR-OCT imaging of intact macaque vagina ex vivo. (A) A 360° circular B-scan image of the vagina duct (Resealed. A scale bar indicates radius to the scanning axis, unit mm).
Figure 28B:
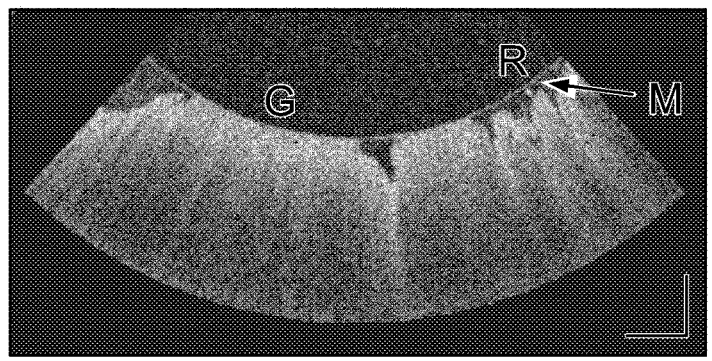
FIG. 28b shows an example high density angular scan covering 45° showing details of the vagina surface structure. As shown in the example of FIG. 28b, a scale bar indicates 100 μm.
Figure 28C:
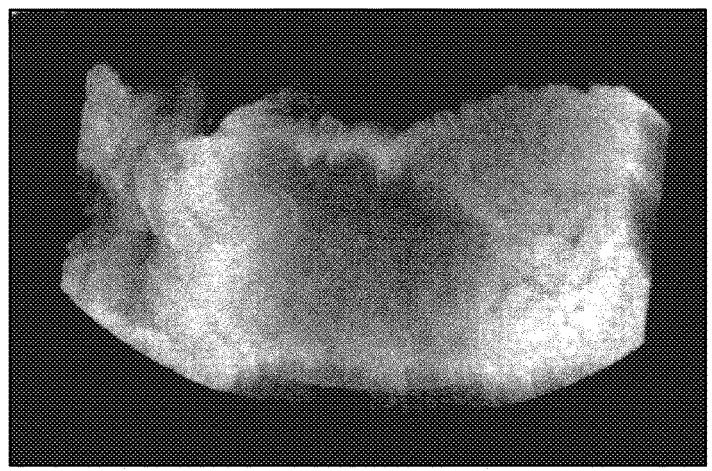
FIG. 28c shows an example 3-dimensional rendering of the same 45° circular scan with 0.8 mm longitudinal displacement, showing the rough structure of the vagina epithelium. R, vaginal rugae; G, glass surface of protective shell; M, granular pattern indicates mucus, NIR, near infrared; OCT, optical coherence tomography.

A 360° cylindrical scan was performed of the intact macaque vagina duct ex vivo. FIG. 28 shows one of the rotational B-scan images of the entire 3-dimensional volumetric dataset. The image was rescaled to enlarge the tissue layers for better visualization, showing the rough surface of the vaginal mucosa. We also conducted a high-resolution volumetric scan covering a scanning angle of 45° (corresponds to 1.2 mm circumference) and 0.8 mm longitudinal displacement. FIG. 28 shows one of the B-scan of the volumetric data. Besides some of the flattened surface caused by the pressure asserted by the protective glass shell, anatomical structures such as vagina rugae were visualized. In addition, the lightened granular pattern in the recess of epithelium indicated the presence of vaginal mucus. The probe was used to show dynamic properties of mucal flow and tissue integrity which could be used for down stream diagnostic and disease monitoring purposes, such as for HIV infection.

Example 5

In one example, a colonoscopy probe or endoscope is adapted for fOCT to evaluate the intestinal wall polyps for cancer. Currently, various other imaging techniques are used in conjunction with endoscopic imaging; however, the approach provides poor sensitivity and specificity. Yet, all cancers are known in the art to be highly vascular due to angiogenesis. Angiogenesis is a process of new blood vessel growth from preexisting blood vessels. Angiogenesis is a fundamental step of tumors from a dormant state to a malignant state, with new blood vessels penetrating into cancerous growths and supplying nutrients and oxygen. Since blood vessels carry hemoglobin, a fOCT enabled probe is able to provide a highly accurate measurements of oxygen consumption as function of blood flow rate and hemoglobin oxygen saturation. Metabolic rate of one or more polyps is calculated as provided by the methods herein. Additionally, the fOCT probe is able to image with high resolution, various aspects of the vasculature underneath or around a polyp to help determine if the polyp may be pre-cancerous or cancerous at an earlier stage. It is generally known in the art that cancers have enhanced metabolic properties compared to normal tissues, so then cancerous cells have higher oxygen content from hemoglobin and a greater concentration of deoxygenated hemoglobin compared to normal tissues. Alternatively, when imaging potential colon cancer polyp with fOCT, comparing the fOCT images and metabolic rate calculations to what a fOCT of normal tissue looks like; diagnosis is possible if increase blood vessel formation appears in the fOCT image. Abnormal blood vessel formation could also be indicative of diseased tissue. For example, abnormal vascular patterns could be indicative of angiogenesis and putative colon cancer. Abnormal vascular patterns would be any vascular patterns outside the normal vasculature anatomy of the health colon tissue.

Example 6

Another example of cancer diagnosis would include breast cancer. A fOCT probe is configured for in a needle and for a surgical tool for use in the removal of the breast cancer tumor. With the needle fOCT probe, the needle is to be placed at sites around the suspected area of the tumor to examine the morphology of the tissue and the tumor's vasculature. 3D fOCT images combined with metabolic rate information of one or more areas of the breast help the surgeon determine optimal surgical margins for excision of the breast cancer tumor. Oxygenated hemoglobin molecules which have increased due to angiogenesis may be indicated to the surgeon by higher metabolic rate as determined and calculated by fOCT methods. The cancerous cells in the breast with the higher oxygen content from hemoglobin and a greater concentration of deoxygenated hemoglobin could be imagined and diagnosed accordingly, when compared to normal breast tissue. Alternatively, when imaging the breast with fOCT, comparing the ultrasound image to what a fOCT image of normal tissue, diagnosis is possible if increased or abnormal blood vessel formation appears.

Example 7

Another example of fOCT, includes configuring methods and devices for diagnostic techniques for diseased tissue with increased blood vessel formation, which could be detectable by with fOCT. Angiogenesis is known to occur during coronary artery disease, peripheral artery disease, and stroke when there's insufficient blood supply. For example, the blood vessels that surround large arteries or perfuse large arterial walls, such as vaso vasorum. These vessels surround the artery around the heart. If there is a plaque in these blood vessels, then the blood supply grows as the plaque size increases, and more cells from these additional blood vessels move into the plaque, making it unstable and more likely to rupture causing heart attacks and strokes. It has been shown that the endothelium of the vaso vasorum is disturbed in hypercholesterolemic conditions. This induces constriction of the vaso vasorun with subsequent lack of oxygen supply. Subsequently VEGF expression will increase with rapid vaso vasorum vessel formation as a consequence. Such increased blood vessel formation could be detectable by described systems herein, as to diagnose susceptible myocardial infarction or ischemic conditions.

Example 8

In this example, fOCT is configured for a probe to be inserted into a catheter, which is directed to the site of an aneurysm. The fOCT probe is able to take successive measurements of the metabolic rate and provide 3D structural images of vessels in and around the aneurysm, informing the surgeon where to operate in an optimally safe place. The fOCT probe is used to guide one or more surgical instruments to the aneurysm site in need of treatment.

Example 9

In this example, fOCT is configured for an intraoperative tool for use to analyze blood vasculature in the brain to help surgeons identify foci of abnormal neural activity. In the treatment of epilepsy, neuromodulation of one or more epileptic foci may be necessary to control epileptic symptoms. In order to identify foci, surgeons use the fOCT probe to identify regions in the brain with abnormal vasculature and increased metabolism, which may correlate with abnormal neural activity associated with epilepsy. Using fOCT data, surgeons identify epileptic foci and apply treatment.

Example 10

In this example, fOCT is used to monitor the treatment and prognosis of a patient with AMD. A patient presents symptoms of early stage AMD including the presence of drusen and sporadic blurriness and black patches in vision. A doctor administers Lucentis®, an FDA approved drug and anti-VEGF drug. The patient's retina is monitored with fOCT before and after administration. After 3 weeks, little to no effect is observed with Lucentis®. The doctor switches treatment and administers another anti-VEGF drug, Eyelea® to the patient. The patient's retina is monitored before and after administration of the drug.

What is claimed is:

1. A method for imaging a target, the method comprising:
  a. performing optical coherence tomography (OCT) scanning on a target with one or more beams of low coherence light, wherein the one or more beams of low coherence light comprise one or more wavelengths and the one or more beams of light are used to perform a single measurement;
  b. acquiring optical information from reflected signals generated by the performed OCT scanning in the single measurement;
  c. quantitatively three dimensional (3D) imaging the target in the single measurement using at least one of visible light or invisible light;
  d. concurrently determining a flow rate of a fluid in the target and a concentration of one or more analytes in the fluid from the acquired optical information and the quantitative 3D imaging in the single measurement;
  e. determining a rate of change of the one or more analyte concentrations in the target based on the determining of flow rate of a fluid and a concentration of one or more analytes, wherein a medical decision is made by determining the rate of change of the one or more analyte concentrations in the target.

2. The method of claim 1, wherein the OCT scanning on the target is performed with identical or different pre-defined scanning trajectories.

3. The method of claim 1, wherein the target is selected from the group consisting of tissue, healthy tissue, diseased tissue, retina, tumor, cancer, growth, fibroid, lesion, skin, mucosal lining, organ, graft, blood supply and one or more blood vessels.

4. The method of claim 1, wherein the fluid is selected from the group consisting of whole blood, blood plasma, blood serum, urine, semen, tears, sweat, saliva, lymph fluid, pleural effusion, peritoneal fluid, meningal fluid, amniotic fluid, glandular fluid, spinal fluid, conjunctival fluid, vitreous, aqueous, vaginal fluid, bile, mucus, sputum and cerebrospinal fluid.

5. The method of claim 1, wherein the analyte is selected from the group consisting of oxygen, hemoglobin, oxygenated hemoglobin, deoxygenated hemoglobin, glucose, sugar, blood area nitrogen, lactate, hematocrit, biomarker and nucleic acid.

6. The method of claim 1, wherein determining the rate of change of one or more analytes is performed by comparing or using a reference.

7. The method of claim 6, wherein the reference is healthy tissue.

8. The method of claim 6, wherein the reference is the target in which the flow rate of a fluid and the concentration of one or more analytes have been previously been quantified.

9. The method of claim 1, wherein one or more images of the target are generated, wherein the one or more images and the change in rate of analyte concentration are used to calculate a function of the target or a change in the function of the target, and wherein the function of the target is a pathological alteration in a tissue.

10. The method of claim 1, wherein an exogenous agent is contacted with the target.

11. The method of claim 10, wherein the exogenous agent is a contrast reagent.

12. The method of claim 1, wherein the method is configured for a device selected from the group consisting of probe, handheld device, wearable device, endoscope, catheter probe, laparoscopic tool, surgical tool, and needle.

13. The method of claim 1, wherein the method is configured to screen or optimize one or more drugs, treatment protocols or pharmaceutical reagents.

14. A non-transitory computer readable medium comprising instructions, which, when executed by a processor, implement method for imaging a target, the method comprising:
- a. performing optical coherence tomography (OCT) scanning on a target with one or more beams of low coherence light, wherein the one or more beams of low coherence light comprise one or more wavelengths and the one or more beams of light are used to perform a single measurement;
- b. acquiring optical information from reflected signals generated by the performed OCT scanning in the single measurement;
- c. quantitatively three dimensional (3D) imaging the target in the single measurement using at least one of visible light or invisible light;
- d. concurrently determining a flow rate of a fluid in the target and a concentration of one or more analytes in the fluid from the acquired optical information and the quantitative 3D imaging in the single measurement;
- e. determining a rate of change of the one or more analyte concentrations in the target based on the determining of flow rate of a fluid and a concentration of one or more analytes, wherein a medical decision is made by determining the rate of change of the one or more analyte concentrations in the target.

15. The non-transitory computer readable medium of claim 14, wherein the OCT scanning on the target is performed with identical or different pre-defined scanning trajectories.

16. The non-transitory computer readable medium of claim 14, wherein determining the rate of change of one or more analytes is performed by comparing or using a reference.

17. The non-transitory computer readable medium of claim 16, wherein the reference is the target in which the flow rate of a fluid and the concentration of one or more analytes have been previously been quantified.

18. The non-transitory computer readable medium of claim 16, wherein one or more images of the target are generated, wherein the one or more images and the change in rate of analyte concentration are used to calculate a function of the target or a change in the function of the target, and wherein the function of the target is a pathological alteration in a tissue.

19. The non-transitory computer readable medium of claim 14, wherein an exogenous agent is contacted with the target.

20. The non-transitory computer readable medium of claim 19, wherein the exogenous agent is a contrast reagent.

* * * * *